US012702294B2

(12) United States Patent
Kalina, Jr. et al.

(10) Patent No.: US 12,702,294 B2
(45) Date of Patent: Aug. 11, 2026

(54) GONIOSCOPES

(71) Applicant: GLAUKOS CORPORATION, Aliso Viejo, CA (US)

(72) Inventors: Charles Raymond Kalina, Jr., Irvine, CA (US); Huong Khac Huynh, Mission Viejo, CA (US); Douglas Daniel Crimaldi, San Marcos, CA (US); Todd N. Fjield, Irvine, CA (US)

(73) Assignee: Glaukos Corporation, Aliso Viejo, CA (US)

( * ) Notice: Subject to any disclaimer, the term of this patent is extended or adjusted under 35 U.S.C. 154(b) by 317 days.

(21) Appl. No.: 18/356,124

(22) Filed: Jul. 20, 2023

(65) Prior Publication Data

US 2024/0090762 A1 Mar. 21, 2024

Related U.S. Application Data

(60) Continuation of application No. 16/894,066, filed on Jun. 5, 2020, now Pat. No. 11,744,458, which is a (Continued)

(51) Int. Cl.
*A61B 17/02* (2006.01)
*A61B 3/117* (2006.01)
*A61B 90/00* (2016.01)

(52) U.S. Cl.
CPC .......... *A61B 3/117* (2013.01); *A61B 17/0231* (2013.01); *A61B 2090/067* (2016.02)

(58) Field of Classification Search
CPC ................ A61B 3/117; A61B 17/0231; A61B 2090/067
See application file for complete search history.

(56) References Cited

U.S. PATENT DOCUMENTS 2,430,851 A 11/1947 Allen
D166,597 S 4/1952 Filsinger
(Continued)

FOREIGN PATENT DOCUMENTS

EP 2755549 7/2014
EP 2967326 1/2016
(Continued)

OTHER PUBLICATIONS

Bahler et al., "Trabecular Bypass Stents Decrease Intraocular Pressure in Cultured Human Anterior Segments", American Journal of Ophthalmology, Dec. 2004, vol. 138, pp. 988-994.
(Continued)

*Primary Examiner* — Mustak Choudhury
(74) *Attorney, Agent, or Firm* — Knobbe, Martens, Olson & Bear, LLP

(57) ABSTRACT

Gonioscope devices are disclosed herein that are configured to enable a medical professional to view structure inside the eye that is ordinarily hidden from normal view. The gonioscope can be an integrally molded single piece that includes both a handle and a gonioscopic optical element. The proximal surface can have a viewing area and a light diffusing area. A recess can provide access to a wound site on the eye while the gonioscope is used for viewing. The handle can be configured to encourage proper alignment of the gonioscope with the eye. The gonioscope can provide an optical fixation point for the subject to focus on to facilitate proper alignment of the eye. The gonioscope can have one or more retention elements configured to engage the tissue of the eye around the contact surface to stabilize the gonioscope. The gonioscope can couple to a lid speculum.

33 Claims, 43 Drawing Sheets

Related U.S. Application Data division of application No. 15/902,904, filed on Feb. 22, 2018, now Pat. No. 10,674,906.

(60) Provisional application No. 62/463,523, filed on Feb. 24, 2017.

(56) References Cited

U.S. PATENT DOCUMENTS

D166,842 S 5/1952 Armbruster
D175,322 S 8/1955 Stegeman
D196,610 S 10/1963 Kolbeck et al.
3,112,570 A 12/1963 Vasconcellos
D205,094 S 6/1966 Pulos et al.
D207,371 S 4/1967 Pulos
3,469,903 A 9/1969 Grichnik et al.
D217,515 S 5/1970 Wells et al.
D217,516 S 5/1970 Wells et al.
3,589,800 A * 6/1971 Cardona ................ A61B 3/117 351/219
3,753,611 A 8/1973 Ebbesen
3,820,879 A 6/1974 Frisen
4,007,980 A 2/1977 Bracher et al.
4,033,679 A 7/1977 Sussman
4,067,646 A 1/1978 Nohda
4,134,647 A 1/1979 Ramos-Caldera
4,134,667 A 1/1979 Schnall et al.
4,205,747 A 6/1980 Gilliam et al.
4,269,307 A 5/1981 LaHaye
4,307,944 A 12/1981 Schirmer
4,439,026 A 3/1984 Wilms
4,469,413 A 9/1984 Shirayanagi
4,568,157 A 2/1986 Kurwa
4,598,984 A 7/1986 Rol
4,627,694 A 12/1986 Volk
4,664,490 A 5/1987 Rol
4,682,866 A 7/1987 Volk
4,721,378 A 1/1988 Volk
4,728,183 A 3/1988 Heacock et al.
4,736,836 A 4/1988 Alongi et al.
4,738,521 A 4/1988 Volk
4,799,784 A 1/1989 Safir
4,907,872 A 3/1990 Schirmer et al.
5,007,729 A 4/1991 Erickson
5,024,518 A * 6/1991 Richards ................ A61B 3/125 351/219
5,046,836 A 9/1991 Volk
5,200,773 A 4/1993 Volk
5,216,456 A 6/1993 Volk
5,260,578 A 11/1993 Bliton et al.
5,281,227 A 1/1994 Sussman
D345,213 S 3/1994 Shalon et al.
5,309,187 A 5/1994 Crossman et al.
5,359,372 A 10/1994 Kida et al.
5,412,441 A 5/1995 Tibbling et al.
5,424,789 A 6/1995 Volk
5,472,440 A 12/1995 Beckman
5,479,222 A 12/1995 Volk
5,501,217 A 3/1996 Ishiguro et al.
5,535,060 A 7/1996 Grinblat
5,537,164 A 7/1996 Smith
5,548,352 A 8/1996 Dewey
5,601,549 A 2/1997 Miyagi
D379,514 S 5/1997 Laun et al.
D394,704 S 5/1998 Koepnick
5,784,147 A 7/1998 Volk
5,805,269 A 9/1998 Volk
5,822,036 A 10/1998 Massie et al.
5,830,139 A 11/1998 Abrue
5,886,822 A 3/1999 Spitzer
5,903,333 A 5/1999 Siminou et al.
5,963,301 A 10/1999 Volk
6,059,772 A 5/2000 Hsia et al.
6,164,779 A 12/2000 Volk
6,183,085 B1 2/2001 Roggy et al.
6,196,686 B1 3/2001 Reiner
D444,236 S 6/2001 Koop et al.
6,266,182 B1 7/2001 Morita
6,450,984 B1 9/2002 Lynch et al.
6,464,724 B1 10/2002 Lynch et al.
6,524,275 B1 2/2003 Lynch et al.
6,569,199 B1 5/2003 Dotan et al.
6,596,026 B1 7/2003 Gross et al.
6,626,858 B2 9/2003 Lynch et al.
6,638,239 B1 10/2003 Bergheim et al.
6,666,841 B2 12/2003 Gharib et al.
6,698,886 B2 3/2004 Pollack et al.
D489,130 S 4/2004 Sinding
D490,152 S 5/2004 Myall et al.
6,730,056 B1 5/2004 Ghaem et al.
6,736,791 B1 5/2004 Tu et al.
6,767,098 B2 7/2004 Erickson et al.
D493,887 S 8/2004 Roberts et al.
6,780,164 B2 8/2004 Bergheim et al.
6,783,544 B2 8/2004 Lynch et al.
6,827,699 B2 12/2004 Lynch et al.
6,827,700 B2 12/2004 Lynch et al.
6,939,298 B2 9/2005 Brown et al.
6,942,343 B2 9/2005 Farberov
6,955,656 B2 10/2005 Bergheim et al.
6,976,758 B2 12/2005 Khaw et al.
6,981,958 B1 1/2006 Gharib et al.
D523,881 S 6/2006 Edwards et al.
7,072,104 B2 7/2006 Okamura et al.
7,094,225 B2 8/2006 Tu et al.
7,125,119 B2 10/2006 Farberov
7,135,009 B2 11/2006 Tu et al.
D534,194 S 12/2006 Hines et al.
7,144,111 B1 12/2006 Ross, III et al.
7,148,970 B2 12/2006 de Boer
7,163,543 B2 1/2007 Smedley et al.
7,186,232 B1 3/2007 Smedley et al.
7,192,412 B1 3/2007 Zhou et al.
7,220,238 B2 5/2007 Lynch et al.
D547,450 S 7/2007 Hurlstone et al.
7,244,024 B2 7/2007 Biscardi
D549,326 S 8/2007 Aparici et al.
7,261,687 B2 8/2007 Yang
7,273,475 B2 9/2007 Tu et al.
7,297,130 B2 11/2007 Bergheim et al.
7,357,504 B2 4/2008 Fischer
7,393,104 B2 7/2008 Hara et al.
D574,867 S 8/2008 Lewis
7,419,262 B2 9/2008 Whalen
7,431,710 B2 10/2008 Tu et al.
7,438,413 B2 10/2008 Kashiwagi et al.
7,447,408 B2 11/2008 Bouma et al.
7,448,752 B2 11/2008 Levine
7,480,058 B2 1/2009 Zhao et al.
7,488,303 B1 2/2009 Haffner et al.
7,494,220 B2 2/2009 Copland
7,501,645 B2 3/2009 Shaver
7,503,605 B2 3/2009 Mears
7,512,436 B2 3/2009 Petty et al.
7,520,611 B2 4/2009 Franz et al.
7,524,064 B2 4/2009 Wyatt
7,549,744 B2 6/2009 Bradley
7,563,241 B2 7/2009 Tu et al.
7,575,321 B2 8/2009 Newman et al.
7,614,747 B2 11/2009 Foster
7,618,372 B2 11/2009 dela Houssaye
7,678,065 B2 3/2010 Haffner et al.
D613,402 S 4/2010 Roberts et al.
7,708,403 B2 5/2010 Newman
7,708,711 B2 5/2010 Tu et al.
7,748,846 B2 7/2010 Todd
7,758,190 B2 7/2010 Korb et al.
7,766,480 B1 8/2010 Graham et al.
7,850,637 B2 12/2010 Lynch et al.
7,857,782 B2 12/2010 Tu et al.
7,867,186 B2 1/2011 Haffner et al.
7,867,205 B2 1/2011 Bergheim et al.
7,879,001 B2 2/2011 Haffner et al.
7,879,079 B2 2/2011 Tu et al.

(56) References Cited

U.S. PATENT DOCUMENTS

| | | | |
|---|---|---|---|
| 7,884,945 | B2 | 2/2011 | Srinivasan et al. |
| D635,257 | S | 3/2011 | Ellman |
| 7,925,133 | B2 | 4/2011 | Bouma et al. |
| 7,951,155 | B2 | 5/2011 | Smedley et al. |
| 7,954,947 | B2 | 6/2011 | Sugita et al. |
| 7,963,654 | B2 | 6/2011 | Aggarwala |
| 7,971,998 | B2 | 7/2011 | Lesk et al. |
| 8,007,459 | B2 | 8/2011 | Haffner et al. |
| D645,489 | S | 9/2011 | Gille et al. |
| D645,490 | S | 9/2011 | Gille et al. |
| 8,011,504 | B1 | 9/2011 | Farberov |
| 8,062,244 | B2 | 11/2011 | Tu et al. |
| 8,070,289 | B2 | 12/2011 | Peyman |
| 8,070,290 | B2 | 12/2011 | Gille et al. |
| 8,075,511 | B2 | 12/2011 | Tu et al. |
| 8,118,768 | B2 | 2/2012 | Tu et al. |
| 8,142,364 | B2 | 3/2012 | Haffner et al. |
| 8,152,752 | B2 | 4/2012 | Lynch et al. |
| 8,226,236 | B2 | 7/2012 | Williams et al. |
| 8,273,050 | B2 | 9/2012 | Bergheim et al. |
| 8,333,742 | B2 | 12/2012 | Bergheim et al. |
| 8,337,445 | B2 | 12/2012 | Tu et al. |
| 8,348,877 | B2 | 1/2013 | Tu et al. |
| 8,369,669 | B2 | 2/2013 | Bouma et al. |
| 8,388,568 | B2 | 3/2013 | Lynch et al. |
| 8,506,515 | B2 | 8/2013 | Burns et al. |
| 8,579,846 | B2 | 11/2013 | Tu et al. |
| 8,617,094 | B2 | 12/2013 | Smedley et al. |
| 8,771,217 | B2 | 7/2014 | Lynch et al. |
| 8,801,648 | B2 | 8/2014 | Bergheim et al. |
| 8,808,219 | B2 | 8/2014 | Bergheim et al. |
| 8,814,820 | B2 | 8/2014 | Bergheim et al. |
| 8,851,676 | B2 | 10/2014 | John et al. |
| 8,882,781 | B2 | 11/2014 | Smedley et al. |
| 9,066,782 | B2 | 6/2015 | Tu et al. |
| D737,450 | S | 8/2015 | Abelson |
| 9,155,654 | B2 | 10/2015 | Tu et al. |
| 9,173,775 | B2 | 11/2015 | Haffner et al. |
| 9,220,632 | B2 | 12/2015 | Smedley et al. |
| 9,301,875 | B2 | 4/2016 | Tu et al. |
| 9,492,320 | B2 | 11/2016 | Lynch et al. |
| 9,554,940 | B2 | 1/2017 | Haffner et al. |
| 9,561,131 | B2 | 2/2017 | Tu et al. |
| 9,572,963 | B2 | 2/2017 | Tu et al. |
| 9,592,151 | B2 | 3/2017 | Rangel-Friedman et al. |
| 9,597,230 | B2 | 3/2017 | Haffner et al. |
| 9,603,738 | B2 | 3/2017 | Haffner et al. |
| 9,636,255 | B2 | 5/2017 | Haffner et al. |
| 9,668,915 | B2 | 6/2017 | Haffner et al. |
| 9,730,638 | B2 | 8/2017 | Haffner et al. |
| 9,789,001 | B2 | 10/2017 | Tu et al. |
| 9,827,143 | B2 | 11/2017 | Lynch et al. |
| 9,962,290 | B2 | 5/2018 | Burns et al. |
| 9,987,472 | B2 | 6/2018 | Tu et al. |
| 9,993,368 | B2 | 6/2018 | Bergheim et al. |
| D833,008 | S | 11/2018 | Kalina, Jr. et al. |
| 10,188,551 | B2 | 1/2019 | Rangel-Friedman et al. |
| 10,206,813 | B2 | 2/2019 | Haffner et al. |
| D846,738 | S | 4/2019 | Kalina, Jr. et al. |
| 10,245,178 | B1 | 4/2019 | Heitzmann et al. |
| 10,271,989 | B2 | 4/2019 | Haffner et al. |
| 10,285,853 | B2 | 5/2019 | Rangel-Friedman et al. |
| 10,285,856 | B2 | 5/2019 | Tu et al. |
| 10,406,029 | B2 | 9/2019 | Tu et al. |
| 10,413,178 | B2 | 9/2019 | Graham et al. |
| 10,485,701 | B2 | 11/2019 | Haffner et al. |
| 10,485,702 | B2 | 11/2019 | Bergheim et al. |
| 10,492,950 | B2 | 12/2019 | Lynch et al. |
| 10,499,809 | B2 | 12/2019 | Kalina, Jr. et al. |
| 10,517,759 | B2 | 12/2019 | Crimaldi et al. |
| 10,568,762 | B2 | 2/2020 | Lynch et al. |
| D886,997 | S | 6/2020 | Kalina, Jr. et al. |
| 10,674,906 | B2 | 6/2020 | Kalina, Jr. et al. |
| 10,813,789 | B2 | 10/2020 | Haffner et al. |
| D901,683 | S | 11/2020 | Kalina, Jr. et al. |
| 10,828,195 | B2 | 11/2020 | Burns et al. |
| 10,828,473 | B2 | 11/2020 | Haffner et al. |
| 10,959,941 | B2 | 3/2021 | Haffner |
| 11,019,996 | B2 | 6/2021 | Kalina, Jr. et al. |
| 11,019,997 | B2 | 6/2021 | Kalina, Jr. et al. |
| 11,039,746 | B1 | 6/2021 | Benner et al. |
| 11,116,625 | B2 | 9/2021 | Kalina, Jr. |
| D938,585 | S | 12/2021 | Kalina, Jr. et al. |
| 11,197,780 | B2 | 12/2021 | Haffner et al. |
| 11,253,394 | B2 | 2/2022 | Haffner et al. |
| 11,298,262 | B2 | 4/2022 | Kahook et al. |
| 11,318,043 | B2 | 5/2022 | Heitzmann et al. |
| 11,376,040 | B2 | 7/2022 | Kalina, Jr. et al. |
| 11,426,306 | B2 | 8/2022 | Haffner et al. |
| 11,523,938 | B2 | 12/2022 | Rangel-Friedman et al. |
| 11,559,430 | B2 | 1/2023 | Crimaldi et al. |
| 11,564,833 | B2 | 1/2023 | Burns et al. |
| 11,744,458 | B2 | 9/2023 | Kalina, Jr. et al. |
| 11,826,104 | B2 | 11/2023 | Kalina, Jr. et al. |
| 11,925,578 | B2 | 3/2024 | Heitzmann et al. |
| 11,944,573 | B2 | 4/2024 | Haffner et al. |
| 11,992,551 | B2 | 5/2024 | Haffner |
| 12,186,237 | B2 | 1/2025 | Burns et al. |
| 12,201,555 | B2 | 1/2025 | Haffner et al. |
| 12,201,557 | B2 | 1/2025 | Haffner et al. |
| 12,208,034 | B2 | 1/2025 | Haffner et al. |
| 12,226,308 | B2 | 2/2025 | Kalina, Jr. |
| 12,279,822 | B2 | 4/2025 | Kalina, Jr. et al. |
| 12,343,288 | B2 | 7/2025 | Haffner et al. |
| 12,376,989 | B2 | 8/2025 | Haffner et al. |
| 12,414,798 | B2 | 9/2025 | Kalina, Jr. et al. |
| 12,419,783 | B2 | 9/2025 | Haffner et al. |
| 12,427,057 | B2 | 9/2025 | Haffner et al. |
| 12,478,503 | B2 | 11/2025 | Haffner et al. |
| 12,478,504 | B2 | 11/2025 | Haffner et al. |
| 2002/0133168 | A1 | 9/2002 | Smedley et al. |
| 2002/0143284 | A1 | 10/2002 | Tu et al. |
| 2003/0055372 | A1 | 3/2003 | Lynch et al. |
| 2003/0060752 | A1 | 3/2003 | Bergheim et al. |
| 2003/0090898 | A1 | 5/2003 | Goldstein et al. |
| 2003/0097151 | A1 | 5/2003 | Smedley et al. |
| 2003/0181848 | A1 | 9/2003 | Bergheim et al. |
| 2003/0187384 | A1 | 10/2003 | Bergheim et al. |
| 2003/0229303 | A1 | 12/2003 | Haffner et al. |
| 2003/0232015 | A1 | 12/2003 | Brown et al. |
| 2003/0236484 | A1 | 12/2003 | Lynch et al. |
| 2004/0024345 | A1 | 2/2004 | Gharib et al. |
| 2004/0036839 | A1 | 2/2004 | Fischer et al. |
| 2004/0111050 | A1 | 6/2004 | Smedley et al. |
| 2004/0147870 | A1 | 7/2004 | Burns et al. |
| 2004/0154946 | A1 | 8/2004 | Solovay et al. |
| 2004/0196431 | A1 | 10/2004 | Farberov |
| 2004/0210185 | A1 | 10/2004 | Tu et al. |
| 2004/0216749 | A1 | 11/2004 | Tu |
| 2004/0254519 | A1 | 12/2004 | Tu et al. |
| 2004/0254520 | A1 | 12/2004 | Porteous et al. |
| 2004/0260228 | A1 | 12/2004 | Lynch et al. |
| 2005/0041200 | A1 | 2/2005 | Rich |
| 2005/0049578 | A1 | 3/2005 | Tu et al. |
| 2005/0165413 | A1 | 7/2005 | Conston et al. |
| 2005/0209549 | A1 | 9/2005 | Bergheim et al. |
| 2005/0250788 | A1 | 11/2005 | Tu et al. |
| 2005/0277864 | A1 | 12/2005 | Haffner et al. |
| 2005/0288619 | A1 | 12/2005 | Gharib et al. |
| 2006/0032507 | A1 | 2/2006 | Tu |
| 2006/0050229 | A1 | 3/2006 | Farberov |
| 2006/0074375 | A1 | 4/2006 | Bergheim et al. |
| 2006/0084907 | A1 | 4/2006 | Bergheim et al. |
| 2006/0173397 | A1 | 8/2006 | Tu et al. |
| 2006/0195055 | A1 | 8/2006 | Bergheim et al. |
| 2006/0195056 | A1 | 8/2006 | Bergheim et al. |
| 2006/0200113 | A1 | 9/2006 | Haffner et al. |
| 2007/0046948 | A1 | 3/2007 | Podoleanu et al. |
| 2007/0088432 | A1 | 4/2007 | Solovay et al. |
| 2007/0195269 | A1 | 8/2007 | Wei et al. |
| 2007/0276483 | A1 | 11/2007 | Aharoni et al. |
| 2007/0282244 | A1 | 12/2007 | Tu et al. |
| 2007/0282245 | A1 | 12/2007 | Tu et al. |
| 2007/0291277 | A1 | 12/2007 | Everett et al. |

(56) References Cited

U.S. PATENT DOCUMENTS

2007/0293807 A1 12/2007 Lynch et al.
2008/0043199 A1 2/2008 Whalen
2008/0045878 A1 2/2008 Bergheim et al.
2008/0068560 A1 3/2008 Knighton et al.
2008/0183121 A2 7/2008 Smedley et al.
2009/0046251 A1 2/2009 Peyman et al.
2009/0076436 A2 3/2009 Gharib et al.
2009/0128776 A1 5/2009 Keating et al.
2009/0137989 A1 5/2009 Kataoka
2009/0149829 A1 6/2009 Collins
2009/0157062 A1 6/2009 Hauger et al.
2009/0180123 A1 7/2009 Knighton et al.
2009/0225324 A1 9/2009 Berstein et al.
2010/0027857 A1 2/2010 Wang
2010/0056979 A1 3/2010 Smedley et al.
2010/0091244 A1 4/2010 Volk
2010/0118269 A1 5/2010 Shea et al.
2010/0118270 A1 5/2010 Shea et al.
2010/0134759 A1 6/2010 Silvestrini
2010/0208201 A1 8/2010 Knighton et al.
2010/0249562 A1 9/2010 Zhang et al.
2010/0265461 A1* 10/2010 Gille ..................... A61B 3/117 351/219
2011/0026789 A1 2/2011 Hsu et al.
2011/0103658 A1 5/2011 Davis et al.
2011/0213342 A1 9/2011 Tripathi et al.
2012/0078158 A1 3/2012 Haffner et al.
2012/0078362 A1 3/2012 Haffner et al.
2012/0099077 A1 4/2012 Abt
2012/0242957 A1 9/2012 Mordaunt
2012/0257167 A1 10/2012 Gille et al.
2012/0259195 A1 10/2012 Haffner et al.
2013/0018295 A1 1/2013 Haffner et al.
2013/0090534 A1 4/2013 Burns et al.
2013/0103145 A1 4/2013 John et al.
2013/0182223 A1 7/2013 Wardle et al.
2013/0253404 A1 9/2013 Tu
2013/0253405 A1 9/2013 Tu
2013/0271729 A1 10/2013 Ranchod
2013/0281910 A1 10/2013 Tu
2013/0310930 A1 11/2013 Tu et al.
2014/0307229 A1 10/2014 Hassan et al.
2015/0223981 A1 8/2015 Smedley et al.
2015/0327764 A1* 11/2015 Graham ............... A61B 3/0091 351/219
2015/0342875 A1 12/2015 Haffner
2016/0045363 A1 2/2016 Haffner et al.
2016/0354309 A1 12/2016 Heitzmann et al.
2017/0135857 A1 5/2017 Haffner et al.
2017/0181622 A1 6/2017 Graham et al.
2017/0231491 A1 8/2017 Tanassi et al.
2017/0340201 A1 11/2017 Rill
2018/0021170 A1 1/2018 Haffner et al.
2018/0028361 A1 2/2018 Haffner et al.
2018/0070817 A1 3/2018 Kalina, Jr. et al.
2018/0085065 A1 3/2018 Haffner et al.
2018/0161205 A1 6/2018 Tu et al.
2018/0280194 A1 10/2018 Heitzmann et al.
2018/0303665 A1 10/2018 Heitzmann et al.
2018/0310821 A1 11/2018 Kalina, Jr. et al.
2018/0333296 A1 11/2018 Heitzmann et al.
2019/0000673 A1 1/2019 Fjield et al.
2019/0021991 A9 1/2019 Heitzmann et al.
2019/0053704 A1 2/2019 Burns et al.
2019/0083307 A1 3/2019 Burns et al.
2019/0104936 A1 4/2019 Gunn et al.
2019/0224046 A1 7/2019 Heitzmann et al.
2019/0321220 A1 10/2019 Rangel-Friedman et al.
2019/0321225 A1 10/2019 Smedley et al.
2020/0155349 A1 5/2020 Haffner et al.
2020/0179171 A1 6/2020 Crimaldi et al.
2020/0214560 A1 7/2020 Kalina, Jr. et al.
2020/0214561 A1 7/2020 Kalina, Jr. et al.
2021/0015662 A1 1/2021 Haffner et al.
2021/0137737 A1 5/2021 Burns et al.
2021/0154449 A1 5/2021 Haffner et al.
2021/0298948 A1 9/2021 Haffner et al.
2021/0315806 A1 10/2021 Haffner
2021/0369447 A1 12/2021 Kalina, Jr.
2022/0000663 A1 1/2022 Haffner et al.
2022/0015628 A1 1/2022 Kalina, Jr. et al.
2022/0119350 A1 4/2022 Murphy et al.
2022/0233349 A1 7/2022 Haffner et al.
2022/0233354 A1 7/2022 Haffner et al.
2022/0313486 A1 10/2022 Heitzmann et al.
2022/0330979 A1 10/2022 Kalina, Jr. et al.
2023/0053931 A1 2/2023 Haffner et al.
2023/0090539 A1 3/2023 Haffner et al.
2023/0157868 A1 5/2023 Haffner et al.
2023/0210694 A1 7/2023 Crimaldi et al.
2023/0293344 A1 9/2023 Burns et al.
2023/0301830 A1 9/2023 Heitzmann et al.
2023/0372303 A1 11/2023 Liu et al.
2024/0065887 A1 2/2024 Heitzmann et al.
2024/0207091 A1 6/2024 Heitzmann et al.
2025/0057758 A1 2/2025 Haffner
2025/0107929 A1 4/2025 Haffner et al.
2025/0134714 A1 5/2025 Burns et al.
2025/0161109 A1 5/2025 Haffner et al.
2025/0161110 A1 5/2025 Heitzmann et al.
2025/0161206 A1 5/2025 Haffner
2025/0169986 A1 5/2025 Haffner et al.
2025/0288461 A1 9/2025 Haffner et al.
2025/0312190 A1 10/2025 Haffner et al.
2025/0375314 A1 12/2025 Haffner et al.

FOREIGN PATENT DOCUMENTS

GB 1319249 6/1973
WO WO 1994/010900 5/1994
WO WO 2000/64389 11/2000
WO WO 2000/64390 11/2000
WO WO 2000/64391 11/2000
WO WO 2000/64393 11/2000
WO WO 2001/97727 12/2001
WO WO 2002/36052 5/2002
WO WO 2002/080811 10/2002
WO WO 2002/087418 11/2002
WO WO 2002/089699 11/2002
WO WO 2003/073968 9/2003
WO WO 2009/158517 12/2009
WO WO 2010/077987 7/2010
WO WO 2013/109771 7/2013
WO WO 2015/180923 12/2015
WO WO 2017/087713 5/2017
WO WO 2025/170932 8/2025

OTHER PUBLICATIONS

"Beam Steering by Wedge Prisms," last updated Jun. 15, 2006, available at: http://micro.magnet.fsu.edu/primer/java/prismsandbeamsplitters/wedgeprisms/index.html.
Beck, Allen D., et al., "360° Trabeculotomy for Primary Glaucoma," Arch. Ophthalmol. 113 (Sep. 1995), pp. 1200-1202.
Buskirk, E. Michael et al., "Lens Depression and Aqueous Outflow in Enucleated Primate Eyes", American Journal of Ophthalmology, vol. 76, No. 5, Nov. 1973, pp. 632-640.
http://glaucomatoday.com/2016/1 O/gonioscopy-is-essential-for-migs/ Posted Oct. 2016.
Guttman, Cheryl, "Continuous IOP Monitoring Possible with Microsensor: Implantable Device Aims to Overcome Deficiencies of Current Monitoring Techniques", (Improvement in Patient Management) (Intraocular Pressure), Ophthalmology Times, Oct. 15, 2003, as cited in HighBeam Research, http://www.highbeam.com/DocPrint.aspx?DocId=1G1:109595800.
Haag-Streit Contact Glasses Brochure, retrieved Mar. 20, 2007.
https://entokey.com/gonioscopy-2/ Uploaded Oct. 2016.
Newell, Frank W., Ophthalmology Principles and Concepts, 1996, Anne S. patterson/Mosby, Eighth edition, pp. 10-21 and 32.
Nickells, Robert W., "Apoptosis of Retinal Ganglion Cells in Glaucoma: An Update of the Molecular Pathways Involved in Cell

(56) References Cited

OTHER PUBLICATIONS

Death", Survey of Ophthalmology, vol. 43, Supplement 1, Jun. 1999, pp. S-151 through S-161.
Ocular Hill Surgical Gonioprism from at least as early as Jun. 29, 2007 in 3 pages, downloaded from http://www.ocularinc.com.
Ocular Khaw Surgical Gonioprism from at least as early as Jun. 29, 2007 in 3 pages, downloaded from http://ocularinc.com.
Ocular Swan Autoclavable Gonioprism from at least as early as Jun. 29, 2007 in 3 pages, downloaded from http://ocularinc.com.
Product No. E8989; Name: Berdahl Gonio Prism Stabilizer, Feb. 2015, http://storzeye.com/products/49940/other-eye-instruments/berdahl-gonio-prism-stabilizer/e8989.aspx.
U.S. Clinical Wick Trials, Oct. 11, 1999, website http://www.cornea.org/us.htm. Allingham, R. R., et al., "Morphometric Analysis of Schlemm's Canal in Normal and Glaucomatous Human Eyes", Glaucoma Paper Presentation, (abstract only—not dated).
Vandenburgh et al., "A Novel Ocular Hypotensive Lipid: Initial Safety and Efficacy of AGN 192024", Glaucoma Clinical Pharmacology II, Abstract B58, IVOS 1998 vol. 39, (cover page and p. S258).
Volk, "Aspheric Ophthalmic Lenses", Refraction, International Ophthalmology Clinics, vol. 5, No. 2, Jun. 1965.
https://web.archive.org/web/20170106073123/http://ocularinc.com/ Available Jan. 6, 2017.

* cited by examiner

FIG. 54
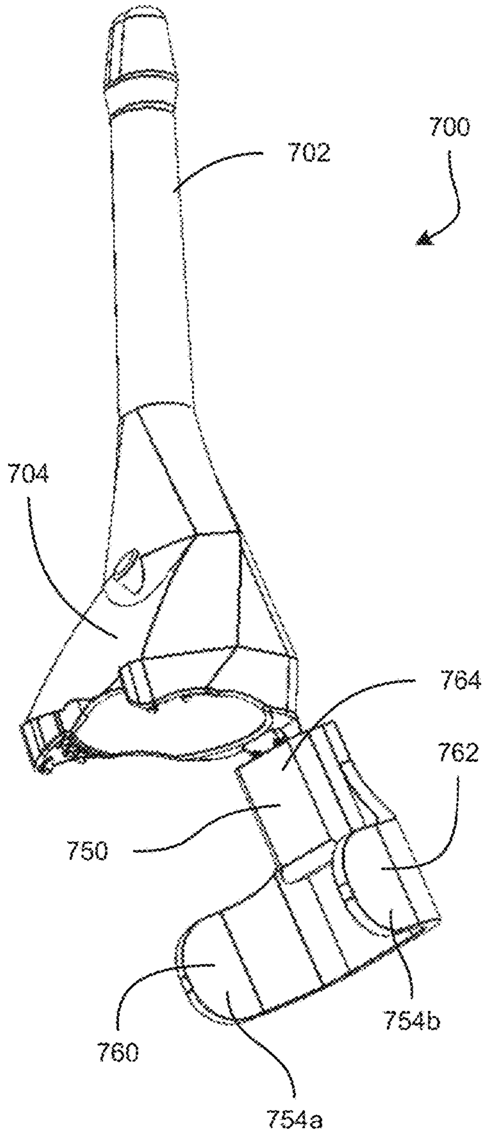
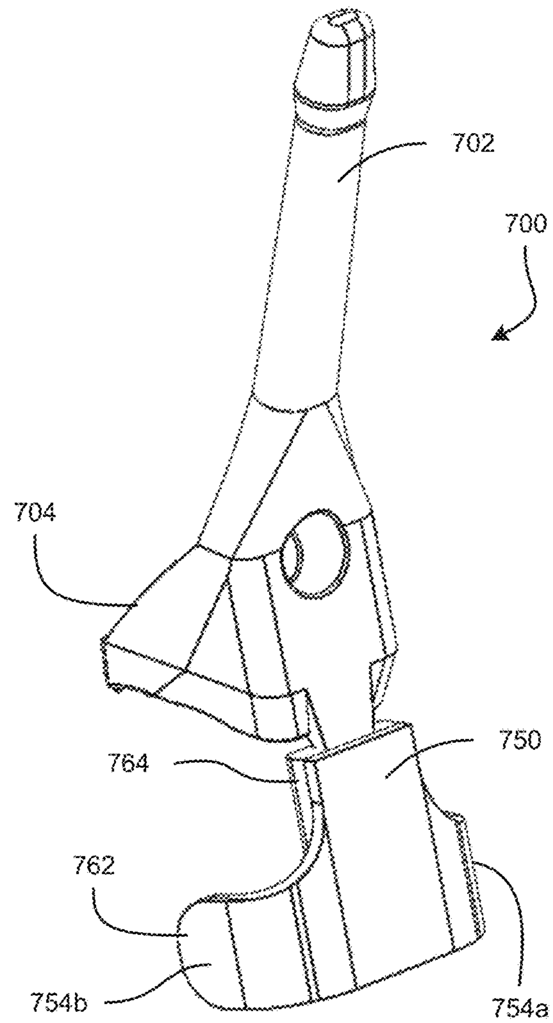
FIG. 55

FIG. 56
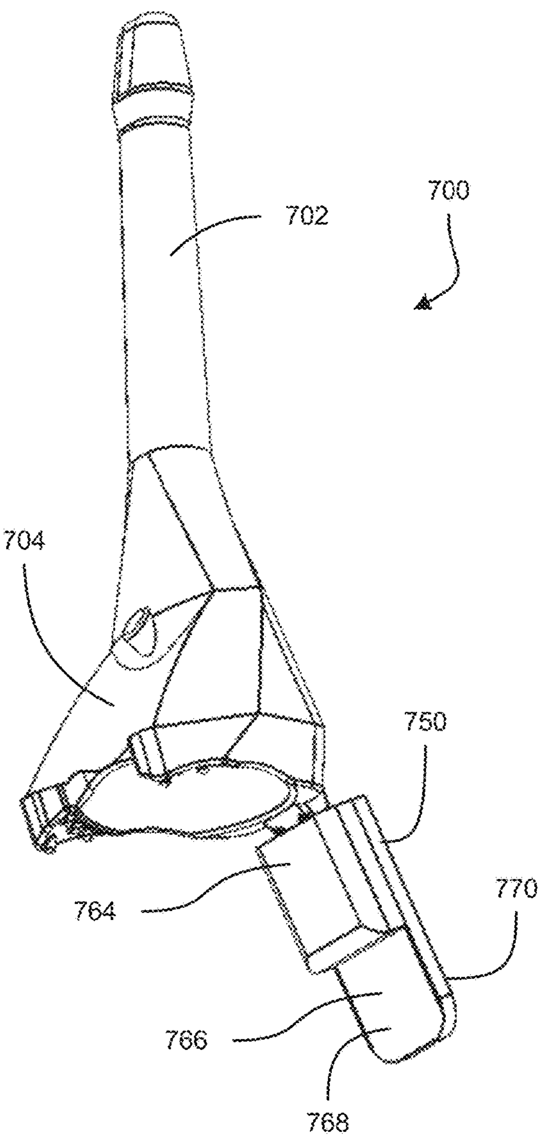
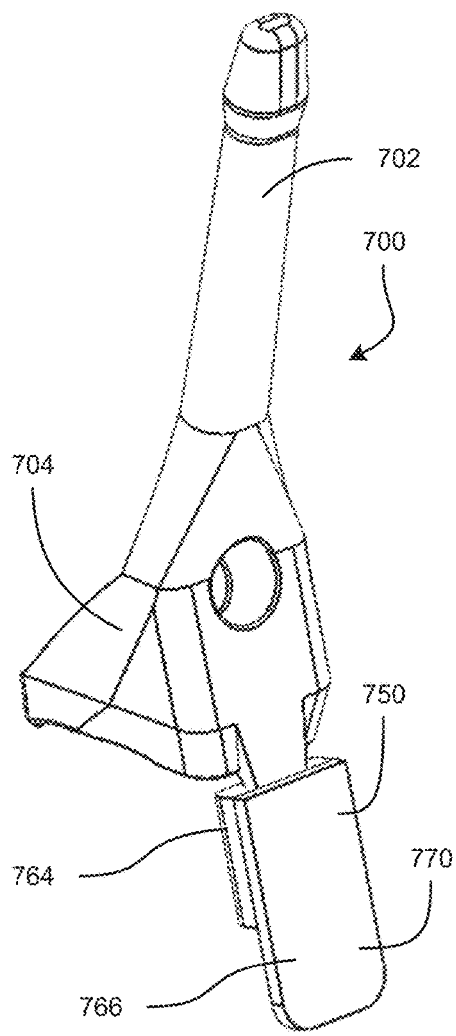
FIG. 57

FIG. 59D
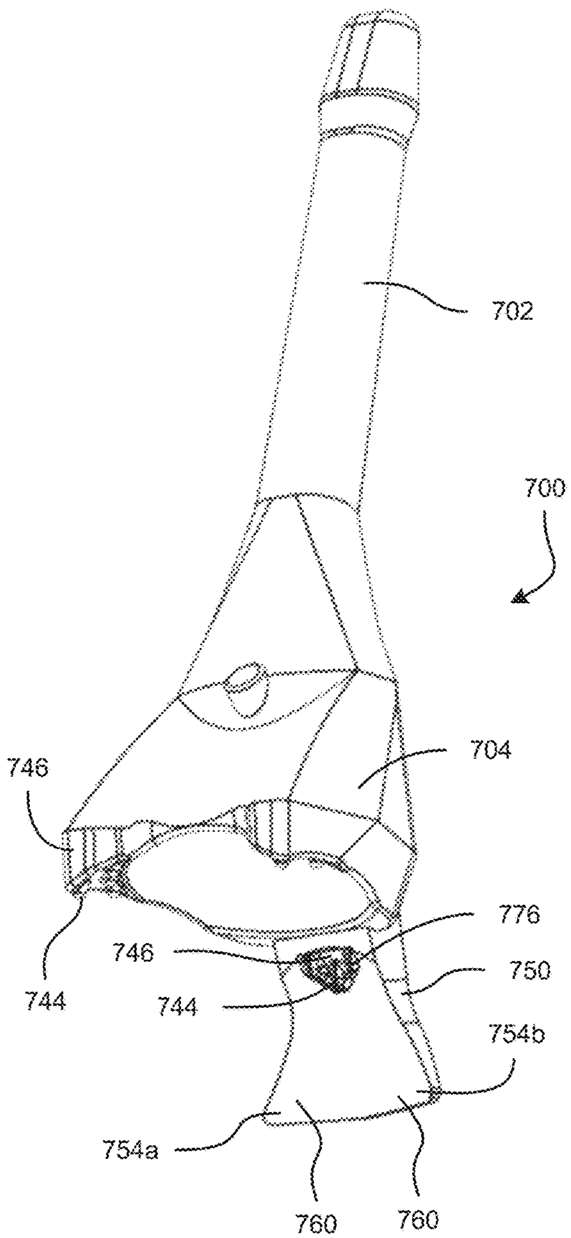
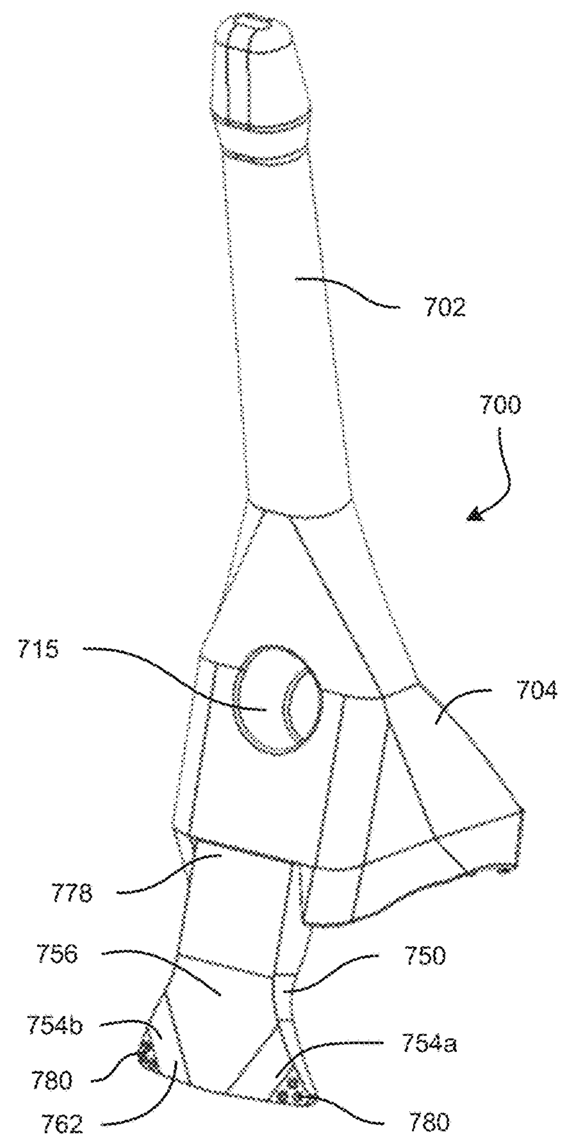
FIG. 59E

GONIOSCOPES

CROSS-REFERENCE TO RELATED APPLICATIONS

This application is a continuation of U.S. patent application Ser. No. 16/894,066, filed Jun. 5, 2020, which is a divisional of U.S. patent application Ser. No. 15/902,904, filed Feb. 22, 2018, which claims the benefit under 35 U.S.C. § 119(e) of U.S. Provisional Patent Application No. 62/463,523, filed Feb. 24, 2017, and titled GONIOSCOPES. The entirety contents of the above-identified application(s) are hereby incorporated by reference herein and made part of this specification for all that they disclose.

INCORPORATION BY REFERENCE

U.S. Pat. No. 8,070,290, issued Dec. 6, 2011, and titled GONIOSCOPE FOR IMPROVED VIEWING, is hereby incorporated by reference in its entirety. U.S. Patent Application Publication No. 2012/0257167, published Oct. 11, 2012, and titled GONIOSCOPE FOR IMPROVED VIEWING, is hereby incorporated by reference in its entirety. PCT Patent Application Publication No. WO 2016/154066, published Sep. 29, 2016, and titled GONIOSCOPIC DEVICES, is hereby incorporated by reference in its entirety.

BACKGROUND

Field of the Disclosure

Various embodiments disclosed herein relate to ophthalmoscopic devices, systems and methods useful for viewing structures including but not limited to the anterior chamber, trabecular meshwork, iris root, scleral spur, and/or related nearby anatomical structures in the eye. Various embodiments described herein may be useful for ophthalmologic diagnoses, treatments, monitoring, and/or surgical procedures.

Description of the Related Art

Gonioscopy is a technique used for viewing the inner parts of the eye, such as the retina and the anterior chamber angle of the eye for evaluation, management, and classification of normal and abnormal structures. Devices used for gonioscopy are known as gonioscopes. Observation of the anterior chamber and especially its angle areas, which are difficult or impossible to see with the use of simple microscopes, can be used for diagnosis of eye diseases. For example, the classification of glaucoma can rely heavily upon knowledge of the anterior segment anatomy, particularly that of the anterior chamber angle. Additionally, some surgical procedures used to treat glaucoma involve placing a small tubular stent into the trabecular meshwork in the anterior chamber angle formed by the iris and the cornea. Proper placement of the stent may depend on visualization of the Trabeculum and the angle.

The anterior chamber of a human eye can be evaluated with an illuminated microscope (e.g., slit lamp stereomicroscopy), but the chamber angle is typically hidden from ordinary view because of total internal reflection of light rays emanating from the angle structures. A small optical device known to ophthalmologists as a gonioscope can be used to enhance visibility of the Trabeculum and the angle. During surgical applications, it may be hand held by the surgeon in place over the patient's cornea while he/she is performing the surgical procedure.

SUMMARY

Certain example embodiments are summarized below for illustrative purposes. The embodiments are not limited to the specific implementations recited herein. Embodiments may include several novel features, no single one of which is solely responsible for its desirable attributes or which is essential to the embodiments.

Various embodiments disclosed herein can relate to a gonioscope that can include a gonioscopic optical element made of transparent material. The gonioscopic optical element can include a distal contact surface that is concave and configured to contact a surface of an eye of a subject, and a proximal surface. The gonioscopic optical element can be configured to receive light from structure inside the eye through the distal contact surface and to output the light through the proximal surface to form an image of the structure inside the eye. The gonioscope can include a handle coupled to the gonioscopic optical element.

In some embodiments, the handle and the gonioscopic optical element can be integrally formed of the same material. The gonioscope can be a disposable item. The gonioscope can be a single-use item.

In some embodiments, the proximal surface can include a viewing portion that can be configured to output the light to form the image of the structure inside the eye, and a light diffusing portion that can be configured to diffuse light that passes through the light diffusing portion. The light diffusing portion can include surface diffusing features. The light diffusing portion can include embedded diffusing features.

In some embodiments, the gonioscopic optical element is configured to form the image with magnification that is less than 1.3×. In some embodiments, the gonioscopic optical element is configured to form the image with magnification that is less than 1.2×. In some embodiments, the gonioscopic optical element can include an anti-reflection coating.

In some embodiments, the gonioscopic optical element can include a curved distal contact surface, a curved proximal surface, and a recess at a front side of the gonioscope formed by an intersection of the curved distal surface and the curved proximal surface. The recess can have a width greater than 7 mm. The recess can have a width greater than 10 mm. The width of the recess can be less than 15 mm.

In some embodiments, the handle can have an elliptical cross-sectional shape with a major axis that is longer than a minor axis. In some embodiments, the handle can be configured to receive light and to propagate the light (e.g., by total internal reflection) to the gonioscopic optical element to input the light into the eye. The handle can be coupled to the gonioscopic optical element at a joint location that is configured to direct light from the handle into the gonioscopic optical element to provide an optical fixation point for the subject. The handle can include one or more light entry areas configured to input light into the handle. In some embodiments, the gonioscope can include an ambidextrous handle coupled to the gonioscopic optical element, and the ambidextrous handle can extend upward along a center plane that divides the gonioscopic optical element into a right side and a left side. The gonioscope and/or the gonioscopic optical element can be symmetrical across the center plane. In some embodiments, the handle can be omitted. In some embodiments, the gonioscope can include a handle coupled to the gonioscopic optical element at a joint location that extends across a width that is at least 50% of the width of the gonioscopic optical element.

In some embodiments, the gonioscope can include a right wing extending from a right side of the gonioscopic optical element and configured to attach to a right-side eye engagement piece of a lid speculum, and a left wing extending from a left side of the gonioscopic optical element and configured to attach to a left-side eye engagement piece of a lid speculum. The right wing can include a hole configured to receive a right post on the lid speculum, and the left wing can include a hole that is configured to receive a left post on the lid speculum.

In some embodiments, the gonioscopic optical element can be configured to receive light from a target structure inside the eye through the distal contact surface and to output the light through the proximal surface to provide an image to a microscope of the target structure inside the eye. The target structure inside the eye can be positioned at a center portion of the image produced by the gonioscopic optical element. The gonioscopic optical element can be configured to receive illumination light from a microscope through the proximal surface and to output the illumination light through the distal surface into eye, such that the target structure receives more of the illumination light than other structures in the eye.

In some embodiments, the gonioscope can weigh less than 3 grams. In some embodiments, the gonioscope can weigh less than 2 grams. In some embodiments, the gonioscope can weigh at least 1 gram. In some embodiments, the distal surface has a radius of curvature of 8 mm to 12 mm.

In some embodiments, the gonioscope includes one or more retention elements configured to engage tissue of the eye to retain the gonioscope in position on the eye. The one or more retention elements can be positioned on one or more arms that extend from the gonioscopic optical element.

Various embodiments disclosed herein can relate to a gonioscope that can include a gonioscopic optical element having a first portion and a second portion. The first portion can include a first distal contact surface that is concave and configured to contact a surface of an eye of a subject at a first location, a first reflection surface, and a second reflection surface. The first portion of the gonioscopic optical element can be configured to receive light from structure inside the eye through the first distal contact surface, to reflect the light from the first reflection surface, to reflect the light from the second reflection surface, and to output the light from the gonioscope to form an image of the structure inside the eye. The second portion can include a second distal contact surface that is concave and configured to contact the surface of the eye at a second location that is spaced apart from the first location. The second portion of the gonioscopic optical element can be configured to receive light from outside the gonioscope and to direct the light through the second distal contact surface to illuminate the structure in the eye.

Various embodiments disclosed herein can relate to a gonioscope that can include a gonioscopic optical element having a first portion and a second portion. The first portion can include a first distal contact surface that is concave and configured to contact a surface of an eye of a subject at a first location. The second portion can include a second distal contact surface that is concave and configured to contact the surface of the eye at a second location that is spaced apart from the first location.

The gonioscope can include a handle, in some embodiments. The handle can include an annular gripping portion positioned around an upper portion of the gonioscopic optical element.

In some embodiments, the gonioscopic optical element can include a proximal surface that extends over both the first portion and the second portion of the gonioscopic optical element.

In some embodiments, the second distal contact portion can be configured to be positioned over the structure of the eye that is being imaged. In some embodiments, the second portion of the gonioscopic optical element can be configured to direct light into the eye without reflecting the light.

In some embodiments, the gonioscope can be configured to block light from outside the gonioscope from entering the eye along the optical axis or along the visual axis of the eye. In some embodiments, the second reflection surface can be configured to be positioned directly above a center of the cornea of the eye. In some embodiments, the first reflection surface can include a reflective material. In some embodiments, the second reflection surface can include a reflective material. The reflective material can include a metal coating.

In some embodiments, the gonioscope can include an optical fixation point light redirection element that is configured to redirect light to provide an optical fixation point viewable by the subject. The light redirection element can include an optical fixation point reflection surface. The optical fixation point light redirection element can be configured to redirect the light toward the outside of the second reflection surface, and the outside of the second reflection surface can be configured to reflect the light into the eye so that the light is visible to the subject to provide the optical fixation point. In some embodiments, the second portion of the gonioscopic optical element can include a surface that has a reflective material with an aperture formed in the reflective material, and the aperture can be configured to enable light redirected by the optical fixation point redirection element to pass through the surface.

Various embodiments can relate to a gonioscope that includes a gonioscopic optical element made of transparent material and having a distal contact surface that is concave and configured to contact a surface of an eye of a subject, and a proximal surface. The gonioscopic optical element can be configured to receive light from structure inside the eye through the distal contact surface and to output the light through the proximal surface to form an image of the structure inside the eye. The proximal surface can be convex along a first direction. The proximal surface can be concave along a second direction. The gonioscope can optionally include a handle coupled to the gonioscopic optical element.

The second direction can be orthogonal to the first direction. The image can have magnification along a first direction of the image that corresponds to the first direction of the proximal surface. The image can have demagnification along a second direction of the image that corresponds to the second direction of the proximal surface. The image can have magnification along a first direction and demagnification along a second direction. The magnification can be between about 1.1× and about 1.5×. The magnification can be between about 1.2× and about 1.4×. The demagnification can be between about 0.95× and about 0.75×. The demagnification can be between about 0.9× and about 0.8×.

Various embodiments can relate to a gonioscope that includes a gonioscopic optical element made of transparent material and having a distal contact surface that is concave and configured to contact a surface of an eye of a subject and a proximal surface. The gonioscopic optical element can be configured to receive light from structure inside the eye through the distal contact surface and to output the light through the proximal surface to form an image of the structure inside the eye. A light entry area can be configured to receive optical fixation light into the gonioscopic optical element. The gonioscopic optical element can include a recess having a base surface configured to redirect the optical fixation light into the eye of the subject to produce an optical fixation feature visible to the subject. The gonioscope can optionally include a handle coupled to the gonioscopic optical element.

The gonioscopic optical element can include a protrusion on a front side, and a surface of the protrusion can include the light entry area. The light entry area can include a curved surface. The light entry area can have optical power. The light entry area can be configured to focus the optical fixation light onto the base surface. The light entry area can be configured to collimate the optical fixation light and to direct the collimated optical fixation light to the base surface. The light entry area can be configured to distribute the optical fixation light across the base surface. The base surface can be configured to reflect the optical fixation light by total internal reflection. The base surface can be configured to scatter the optical fixation light. The base surface can have a first area configured to direct a first amount of the optical fixation light into the eye to produce a first portion of the optical fixation feature visible to the subject, and a second area configured to direct a second amount of the optical fixation light into the eye to produce a second portion of the optical fixation feature visible to the subject. The first portion can be visible distinct from the second portion. The first portion can be brighter than the second portion.

Various embodiments can relate to a gonioscope that includes a gonioscopic optical element made of transparent material having a distal contact surface that is concave and configured to contact a surface of an eye of a subject, and a proximal surface. The gonioscopic optical element can be configured to receive light from structure inside the eye through the distal contact surface and to output the light through the proximal surface to form an image of the structure inside the eye. The gonioscope can include markings that are visible in the image. The gonioscope can optionally include a handle coupled to the gonioscopic optical element.

The markings can be on the distal contact surface and/or on the proximal surface and/or embedded in the gonioscopic optical element. The markings can divide the image into a plurality of areas. The markings can include a plurality of lines. The markings can include a plurality of areas having different light transmission properties. The markings can include a plurality of areas having different colors. The markings can designate angle increments in the image.

Various embodiments can relate to a gonioscopic system that includes a gonioscope having a gonioscopic optical element made of transparent material and including a distal contact surface that is concave and configured to contact a surface of an eye of a subject, and a proximal surface. The gonioscopic optical element can be configured to receive light from structure inside the eye through the distal contact surface and to output the light through the proximal surface to form an image of the structure inside the eye. The gonioscope can optionally include a handle. The system can include a support having an engagement element configured to attach the support to the gonioscope and an eye engagement feature configured to engage between the eye and an anatomical structure adjacent the eye to support the gonioscope.

The engagement element can include a handle attachment configured to attach to the handle of the gonioscope. The handle attachment can include a through hole configured to receive the handle therethrough. The gonioscope can include at least one arm extending from the gonioscopic optical element, and the engagement element can include an arm attachment configured to attach to the arm. The arm attachment can include a recess configured to receive the arm therein. The gonioscope can include a recess, and the engagement element can include a protrusion configured to be received into the recess of the gonioscope. The eye engagement feature can include at least one flap configured to fit between the eye and an eyelid. The eye engagement feature can have a first flap configured to fit between the eye and an upper eyelid and a second flap configured to fit between the eye and a lower eyelid. The eye engagement feature can include at least one flap configured to engage a corner of the eye.

BRIEF DESCRIPTION OF THE DRAWINGS

Certain embodiments will be discussed in detail with reference to the following figures, wherein like reference numerals refer to similar features throughout. These figures are provided for illustrative purposes and the embodiments are not limited to the specific implementations illustrated in the figures.

FIG. 54 is a bottom-front perspective view of an example embodiment of a support being used with a gonioscope.

FIG. 55 is a top-rear perspective view of an example embodiment of a support being used with a gonioscope.

FIG. 56 is a bottom-front perspective view of an example embodiment of a support being used with a gonioscope.

FIG. 57 is a top-rear perspective view of an example embodiment of a support being used with a gonioscope.

FIG. 59D is a bottom-front perspective view of another example embodiment of a support, shown coupled to a gonioscope.

FIG. 59E is a top-rear perspective few of the support coupled to the gonioscope.

DETAILED DESCRIPTION OF CERTAIN EMBODIMENTS

Figure 1:
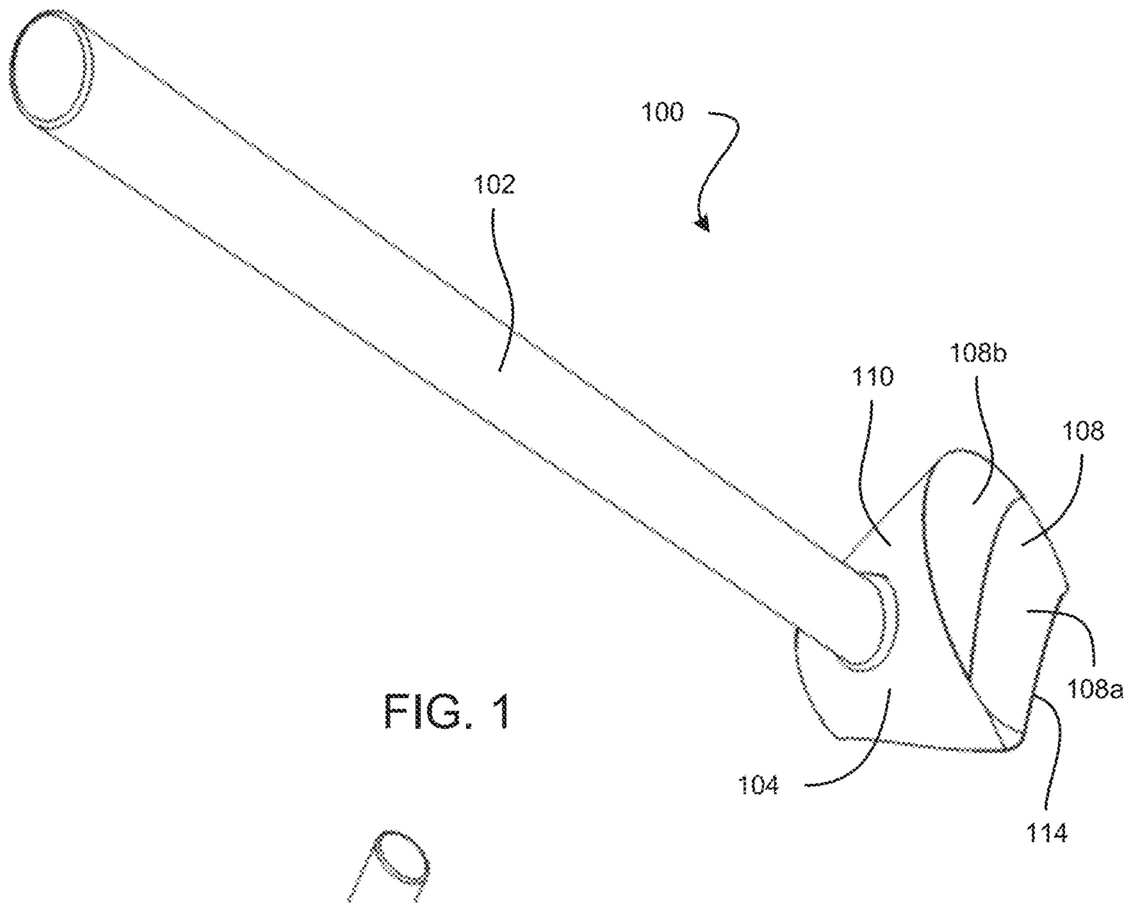
FIG. 1 is a top-front perspective view of an example embodiment of a gonioscope.
Figure 2:
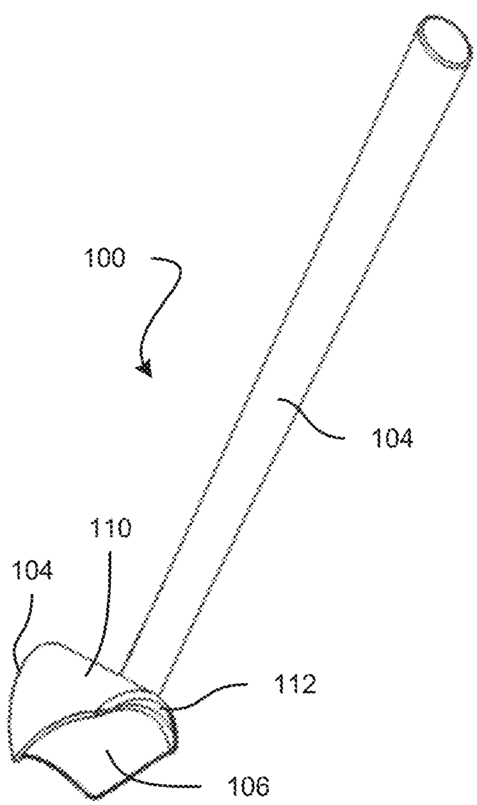
FIG. 2 is a bottom-rear perspective view of the example embodiment of a gonioscope.
Figure 3:
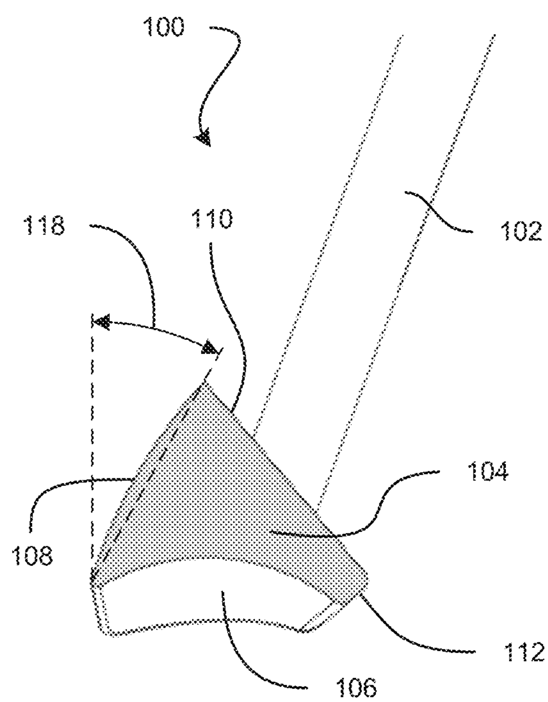
FIG. 3 is a cross-sectional view taken through a center of an example gonioscopic optical element.
Figure 4:
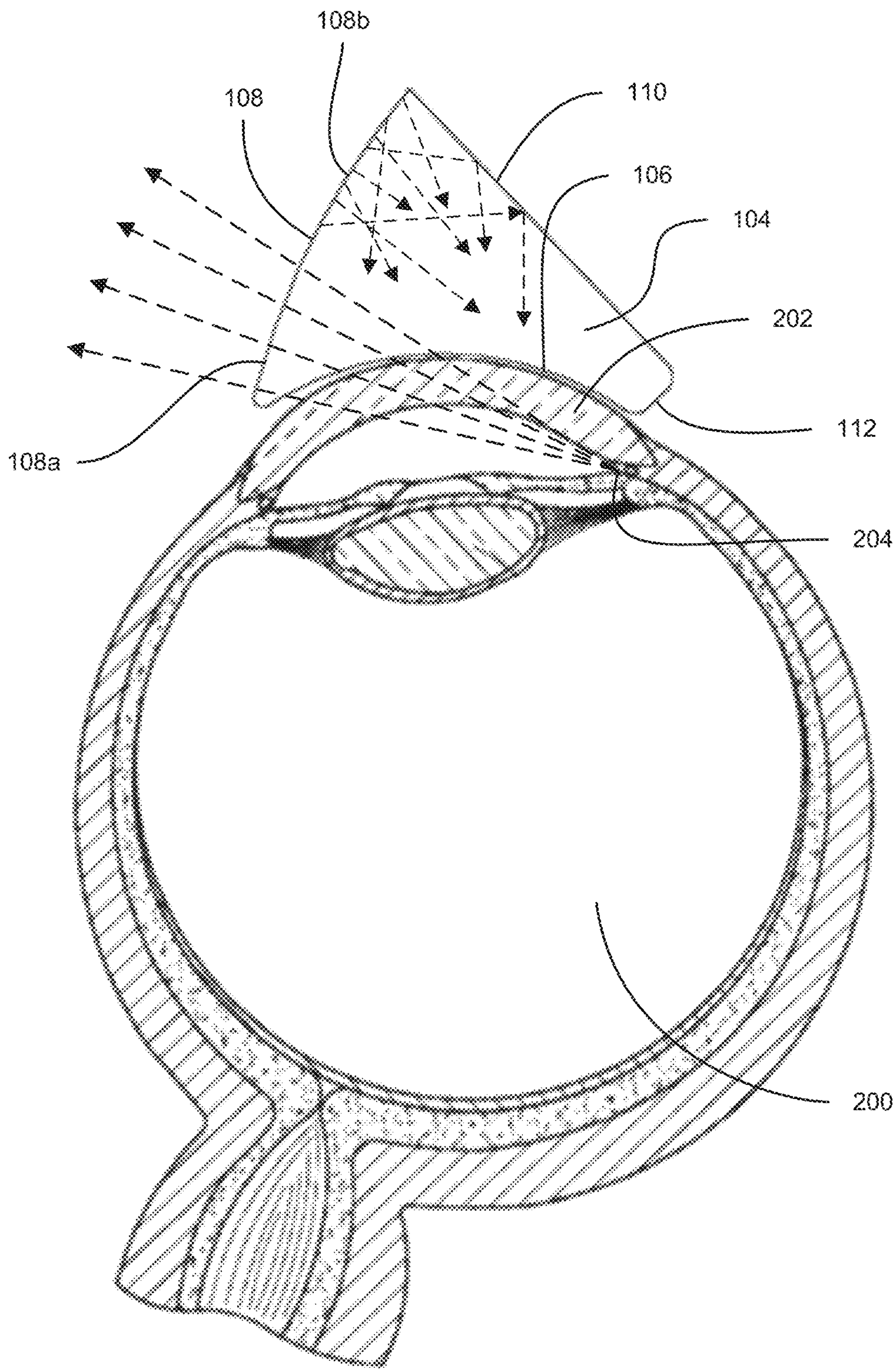
FIG. 4 shows a cross-sectional view of an example gonioscopic optical element positioned on the cornea of an eye.

FIG. 1 is a top-front perspective view of an example embodiment of a gonioscope 100. FIG. 2 is a bottom-rear perspective view of the example embodiment of a gonioscope 100. The gonioscope 100 can include a handle 102 attached to a gonioscopic optical element 104. FIG. 3 is a cross-sectional view taken through a center of the gonioscopic optical element 104. The gonioscope 100 can be configured to be used for viewing structures inside the eye of a subject, including but not limited to the anterior chamber, trabecular meshwork, iris root, scleral spur, and/or related nearby anatomical structures in the eye. FIG. 4 shows a cross-sectional view of the gonioscopic optical element 104 positioned on the cornea 202 of an eye 200. Light from inside the eye 200 (e.g., the anterior chamber angle 204) that would normally be hidden from view by total internal reflection can be permitted to exit the eye through the gonioscopic optical element 104. In some instances, an optical material such as index matching gel, can fill the space between the gonioscopic optical element 104 and the surface of the eye 200 (e.g., the cornea 202). The light exiting the eye through the gonioscopic optical element 104 can be viewed by a medical professional (e.g., using a microscope, using another imaging device, or using the naked eye). The gonioscope 100 can be used for imaging inside the eye 200 for diagnostic purposes as well as for treatment, such as during implantation or removal of a medical device (e.g., for viewing the anterior chamber angle during implantation of a stent into the trabecular meshwork).

The gonioscopic optical element 104 can be a contact lens and can include a distal surface 106 having a concave shape that is configured to contact a surface of a subject's eye, such as the cornea. The distal surface 106 can have a spherical shape. In some embodiments, the surface of the distal surface 106 can be configured to substantially match the shape and size of the cornea of an average eye so as to provide a good fit with the subject's eye. In some embodiments, the concave distal surface 106 may have a radius of curvature between about 5 mm and 11 mm, although curvatures outside this range are also possible. In some embodiments, the concave distal surface 106 can have a radius of curvature that is larger than the cornea of an average eye. For example, the radius of curvature of the distal surface 106 can be greater than 7.5 mm, greater than 8 mm, greater than 9 mm, greater than 10 mm, greater than 11 mm, greater than 12 mm, or any values therebetween, or any ranges bounded by any combination of these values, although values outside these ranges could be used in some instances. The distal surface 106 can have a radius of curvature of 15 mm or less. In some instances, bubbles can be formed in the optical material (e.g., index matching gel) when the gonioscopic optical element 104 is place on the eye 200. A distal surface 106 having a greater radius of curvature than the contact portion on the eye 200 (e.g., the cornea 202) can force the bubbles out of the viewing area (e.g., towards the edges of the gonioscopic optical element 104).

The gonioscopic optical element 104 can also include a proximal surface 108, which can be planar or have a curved (e.g., spherical or toroidal) shape. In some embodiments, the proximal surface 108 can include an imaging portion **108*a* and a light diffusing portion 108*b*. The imaging portion 108*a* can be a smooth surface. As shown in FIG. 4, light from the area being imaged inside the eye 200 (e.g., the anterior chamber angle 204) can exit the eye 200 and enter the gonioscopic optical element 104 through the distal surface 106. The light can propagate through the gonioscopic optical element 104, and can exit the gonioscopic optical element 104 through the imaging portion 108*a* of the proximal surface 108. In some embodiments, the light diffusing portion 108*b* can be omitted, and the entire proximal surface 108 can operate as the viewing portion 108*b***.

Figure 5:
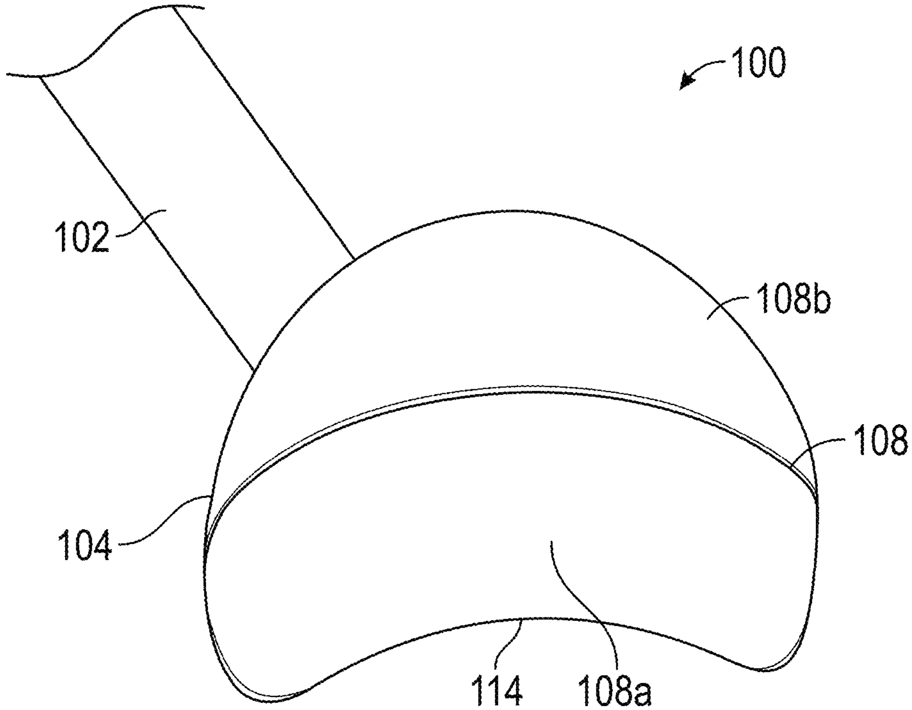
FIG. 5 shows a partial front view of an example embodiment of a gonioscope.
Figure 6:
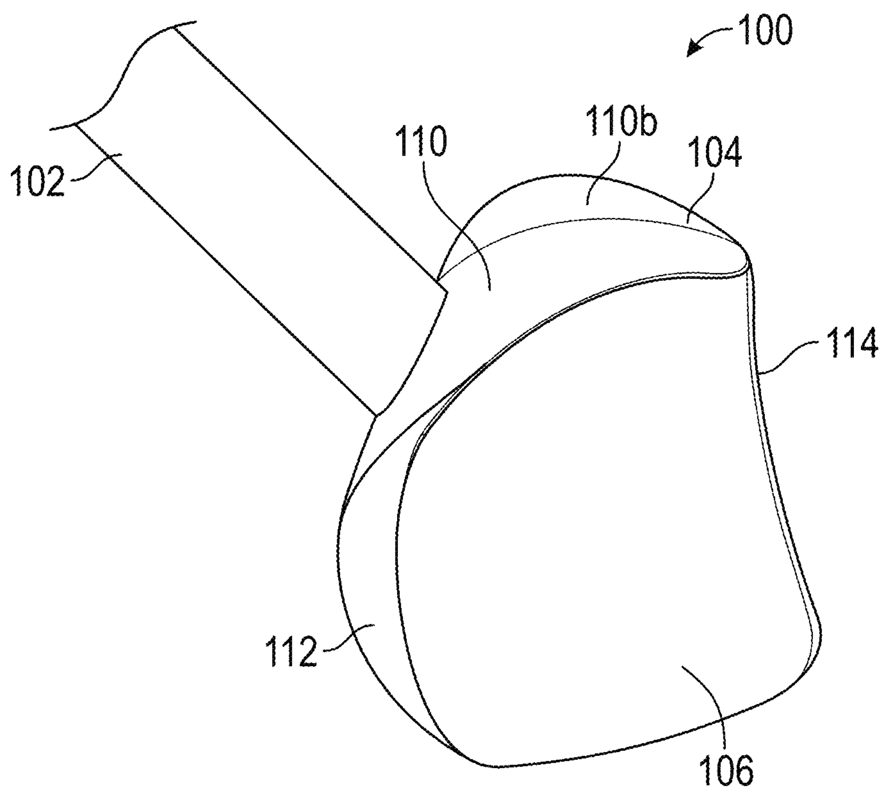
FIG. 6 shows a bottom-rear partial perspective view of an example embodiment of a gonioscope.

The light diffusing portion **108*b* can be configured to diffuse light that passes through the light diffusing portion 108*b*. In some embodiments, the light diffusing portion 108*b* can have surface diffusing features, such as a roughened (e.g., irregular) or frosted surface, as can be seen for example in FIG. 5. For example, a mold that is used to make the gonioscopic optical element 104 (e.g., by injection molding) can have a roughened mold surface configured to form the light diffusing portion 108*b*. In some embodiments, the light diffusing portion 108*b* can initially be smooth, and the light diffusing portion 108*b* can be roughened (e.g., by etching or abrasion) to form surface diffusing features. In some embodiments, a film or coating having surface diffusing features can be applied to the light diffusing portion 108*b*. In some embodiments, the light diffusing portion 108*b* can have embedded diffusing features, such as particulates or voids embedded in the body of the gonioscopic optical element 104 at the light diffusing portion 108*b*, which can be sized and spaced to diffuse light passing through the light diffusing portion 108*b***.

The light diffusing area **108*b* can improve illumination of the structure inside the eye 200 that is being imaged. For example, light from outside the gonioscope 100 (e.g., ambient light and/or light from a microscope or other illumination device) can enter the gonioscopic optical element 104 through the light diffusing portion 108*b* and can be scattered, as can be seen in FIG. 4. Some of the scattered light can be directed into the eye 200 and can illuminate the area being imaged (e.g., the anterior chamber angle 204). Accordingly, in some cases light that otherwise would have avoided the area of the eye 200 being imaged can be redirected to the imaging area by the light diffusing portion 108*b*. Light entering the gonioscopic optical element 104 through the viewing portion 108*a*** can also provide illumination to the imaging area.

The light diffusing portion **108*b* can also impede the light exiting the gonioscopic through the light diffusing portion 108*b* from forming an image. This can focus the attention of the medical professional on the image formed by the imaging portion 108*a*. In many cases, the light that exits the gonioscopic optical element 104 through the light diffusing portion 108*b* is from portions of the eye that are not relevant to the diagnosis or treatment being performed. As discussed further herein, some embodiments can direct light into the eye to provide a fixation point for the subject. In some cases, the light diffusing portion 108*b*** can diffuse the fixation point light that exits the gonioscopic optical element, which can impede the formation of a bright spot that can be distracting to the medical professional.

The gonioscopic optical element 104 can have a back surface 110. In some embodiments, some or all of the back surface 110 can include a light diffusing portion **110*b*, which can have features similar to the light diffusing portion 108*b* of the proximal surface 108. The light diffusing portion 110*b* can have surface diffusing feature, or embedded diffusing features, a roughened or frosted surface, etc., as discussed in connection with the light diffusing portion 108*b*. Light from outside the gonioscope 100 (e.g., ambient light and/or light from a microscope or other illumination device) can enter the gonioscopic optical element 104 through the back surface 110 and can be scattered by the light diffusing portion 110*b*, similar to the scattered light in FIG. 4. Some of the scattered light can be directed into the eye 200 and can illuminate the area being imaged (e.g., the anterior chamber angle 204). For example, some of the light that is scattered can reflect off of the back surface 110 of the gonioscopic optical element (e.g., by total internal reflection or from a reflective material such as a metal coating applied to the outside of the back surface 110) to be directed into the eye 200, as can be seen in FIG. 4. In some cases light that otherwise would have avoided the area of the eye 200 being imaged can be redirected to the imaging area by the light diffusing portion 110*b*. In some cases light that otherwise would have been focused to a central point due to the curvature of the back surface of the gonioscopic optical element 404 can be distributed for illuminating the anterior chamber angle and/or the trabeculum due to the light diffusing portion 110*b*. In some embodiments, all or portions of the gonioscope 100 (e.g., one or more of the gonioscopic optical element, the proximal surface 108, and the back surface 110) can have an anti-reflective coating, which can improve light transfer through the gonioscope 100**.

The gonioscopic optical element 104 can have a generally triangular cross-sectional shape, as can be seen in FIG. 3. The gonioscopic optical element 104 can have a wedge shape. The gonioscopic optical element can be a prism or a lens. The distal surface 106 can be a bottom side, in that the distal surface 106 is primarily visible when the gonioscope 100 is viewed from the bottom. The proximal surface 108 can be a front side, in that the proximal surface 108 is primarily visible when the gonioscope 100 is viewed from the front. The back surface 110 can be a back side of the gonioscopic optical element 104, in that the back surface 100 is primarily visible when the gonioscope 100 is viewed from the back. It will be understood that the back surface 110 is curved such that portions of the back surface 110 wrap down onto side areas of the gonioscopic optical element 104.

The proximal surface 108 (e.g., front side) and the back surface 110 can intersect at a first edge. The distal surface 106 (e.g., bottom side) and the back surface 110 can intersect at a second edge. The second edge can be blunt or rounded, to impede the second edge from injuring the eye 200 of the subject. In some embodiments, a bumper 112 can be at a rear portion of the second edge, and can be configured to abut against an eyelid or other tissue adjacent the eye 200 to facilitate positioning of the gonioscopic optical element 104 for viewing inside the eye 200. The bumper 112 can have a crescent shape, and can be formed by the intersection of the distal surface 106 and the back surface 110 at a rear of the gonioscopic optical element 104.

The distal surface 106 (e.g., bottom side) and the proximal surface 108 (e.g., front side) can intersect at a third edge. The third edge can be blunt or rounded, to impede the third edge from injuring the eye 200 of the subject. A recess 114 at a front of the gonioscopic optical element 104 can facilitate providing access for a medical tool during surgery. The recess 114 can be crescent shaped. The recess 114 can be formed by the intersection of the distal surface 106 and the proximal surface 108. As can be seen by comparing FIGS. 7 and 8, the recess 114 can provide a larger recess area for improved access to the wound site during surgery (see FIG. 7), as compared to some gonioscopes where a recess is provided by grinding away material of the gonioscopic optical element (see FIG. 8). The gonioscope 100 can be configured to have a recess 114 that provides a large recess area while also providing an image of the interior eye structure (e.g., anterior chamber angle 204) that is spaced away from the recess 114 (see FIG. 7). Note that for the gonioscope of FIG. 8, if the recess area were increased to provide more room for access to the wound site, the recess area would encroach further into the image of the eye structure. The recess 114 of the gonioscope 100 can have a width 116 of greater than 7 mm, greater than 8 mm, greater than 9 mm, greater than 10 mm, greater than 11 mm, greater than 12 mm, greater than 13 mm, greater than 14 mm, or any values therebetween, or any ranges bounded by any combination of these values, although values outside these ranges can be used in some implementations. The width 116 can be less than 15 mm, in some embodiments.

The proximal surface 108 can be angled forward more than a traditional gonioscope. With reference to FIG. 3, when the gonioscope 100 is oriented with edges of the distal surface 106 flat along a horizontal plane, the proximal surface 108 can be angled away from vertical by an angle 118 that can be 45 degrees, 40 degrees, 35 degrees, 30 degrees, 25 degrees less, 20 degrees, 15 degrees, 10 degrees, or any values therebetween, or any ranges bounded by any combination of these values, although values outside these ranges can be used in some instances. In some embodiments, the light can be refracted as it exits the gonioscopic optical element 104, such as to redirect the light in a more vertical direction or to otherwise redirect the light towards a microscope or other imaging device. In some embodiments, the curved proximal surface can make the image appear larger in the vertical direction. The proximal surface 108 can be configured (e.g., the orientation and/or curvature thereof) to direct light entering the proximal surface 108 from a light source (e.g., the microscope) to be directed toward the target tissue to be imaged (e.g., the anterior chamber angle), as compared to some other gonioscopes, which can direct most of the incoming light onto the iris of the eye or other structure not being imaged for the medical procedure. In some embodiments, the proximal surface 108 (e.g., the imaging portion 108*a* thereof) can be configured to not redirect light from the imaging area (e.g., the anterior chamber angle 204) during use.

Figure 7:
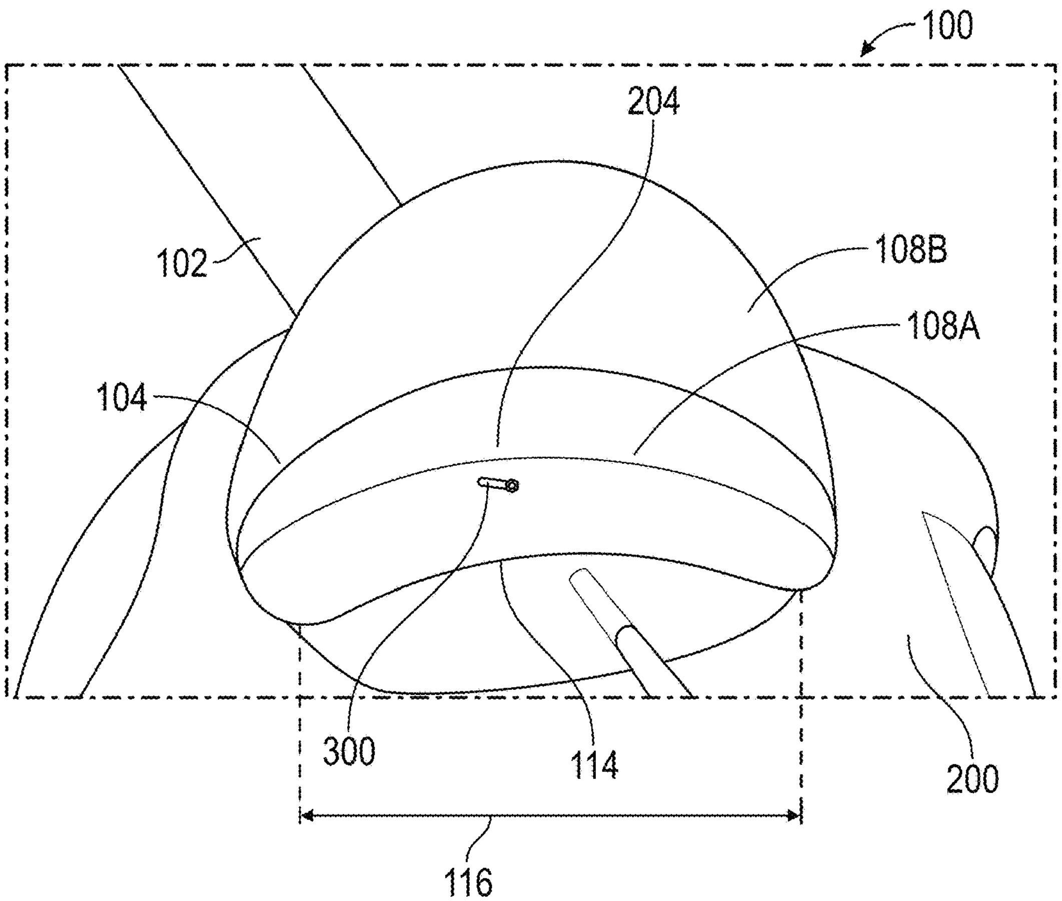
FIG. 7 shows a front partial view of an example embodiment of a gonioscope imaging a medical device inside an eye.
Figure 8:
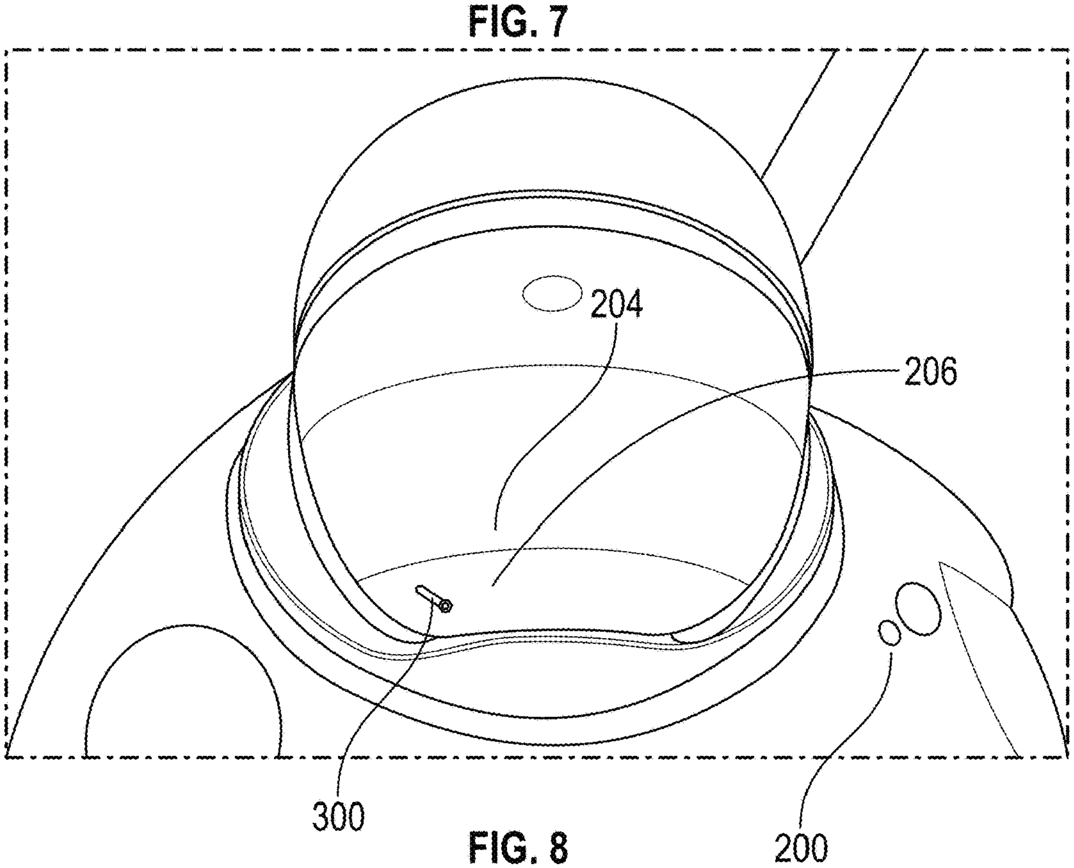
FIGS. 8-10 show front partial views of another gonioscope imaging a medical device inside an eye.
Figure 9:
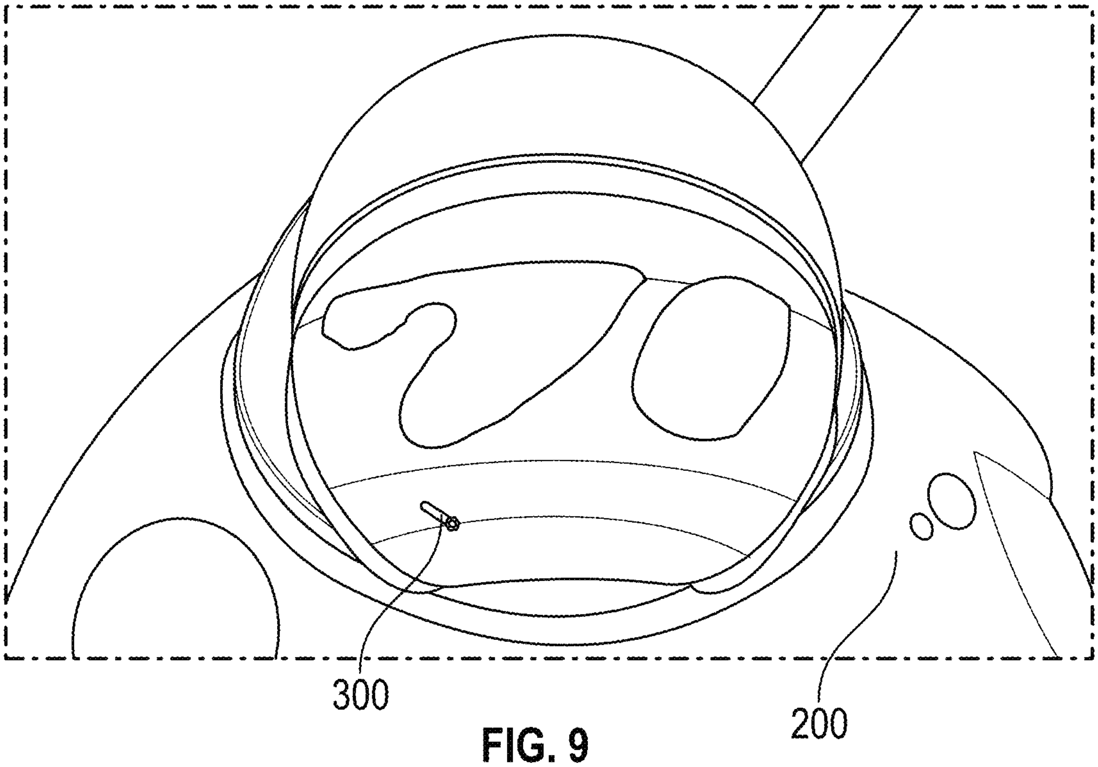
Figure 10:
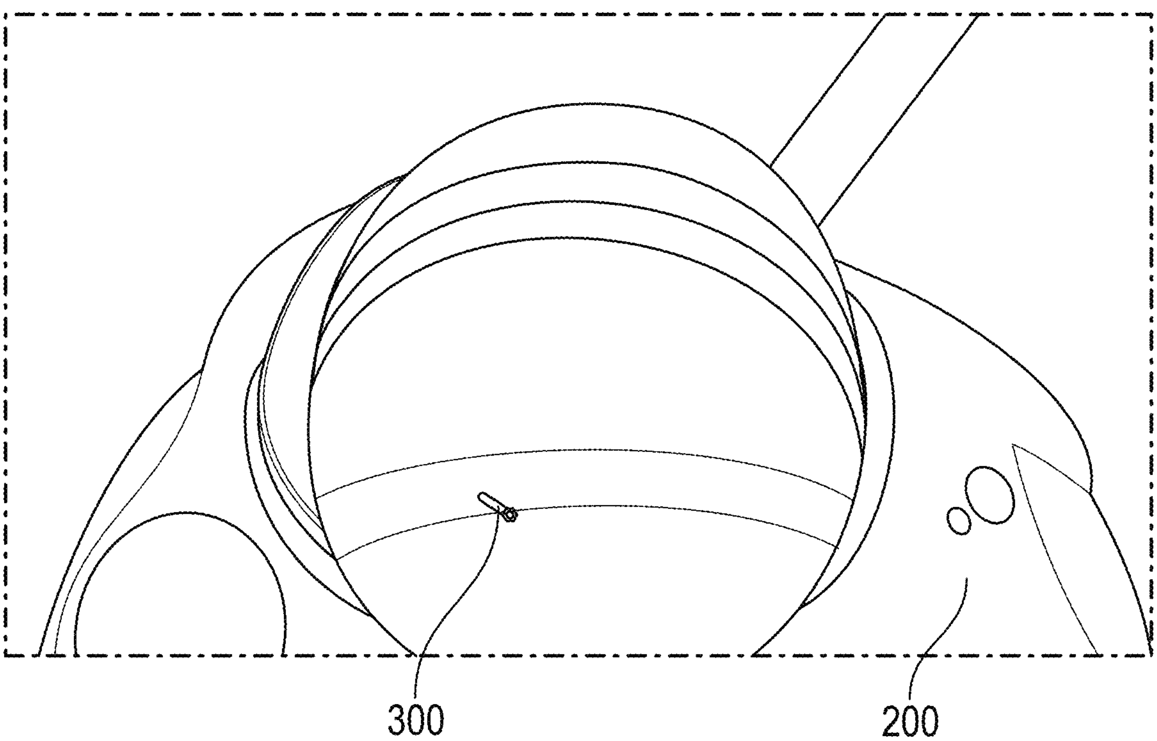

The configuration of the gonioscopic optical element 104 can provide an improved viewing location, as compared to other gonioscopes. FIG. 7 shows the gonioscope 100 being used to image the anterior chamber angle of the eye (e.g., the trabecular meshwork). In FIG. 7, a medical device 300 is in the eye 200, near the trabecular meshwork. In an example medical procedure, a medical professional may use a medical tool to remove or reposition a medical device 300 (e.g., a stent) that improperly positioned near the trabecular meshwork. The target imaging area can be positioned in a generally centralized region of the viewing portion 108*a* of the gonioscope 100 when the gonioscope is positioned with the curvature of the distal surface 106 aligned with the curvature of the contact surface of the eye 200 (e.g., the cornea 202). FIG. 8 shows a different gonioscope where the proximal surface of the gonioscopic optical element is angled further back, which can cause the target image area to be positioned at the edge of the viewing area or in some cases can impede the formation of an image of the target viewing area when the distal surface is aligned with the curvature of the eye 200. In practice, a medical professional may angle the gonioscope of FIG. 8 so that the back lifts up away from the eye 200 in order to position the target image area more in the center of the viewing area on the gonioscope. Lifting the back of the gonioscope can cause the gonioscope to separate from the optical material (e.g., index matching gel), as can be seen in FIG. 9, which can impede the formation of the image. A medical professional may need to remove the gonioscope and add additional optical material (e.g., index matching gel) to enable imaging with the gonioscope lifted forward. Also, suspending the gonioscope steady while angled forward can be difficult, especially since the medical professional would often be operating a medical tool to perform a surgical procedure at the same time. Furthermore, as can be seen in FIG. 10, when the gonioscope is angled forward, the gonioscope can encroach into the area (e.g., the wound site) where the medical professional would need to insert the medical tool. In some cases, the medical professional may move the gonioscope back and forth during a surgical procedure to alternate between providing access to the wound site and providing a suitable image of the target image area. As the medical professional navigates the medical tool during a surgical procedure, the medical tool can bump into or nib against the gonioscope when angled forward, which can restrict motion of the medical tool or can impede the medical professional from accurately positioning the medical tool. As can be seen in FIG. 7, the gonioscope 100 can provide a generally centralized view of the target viewing area while also providing access to the wound site, without angling the gonioscope

100 forward. In some embodiments, the gonioscopic optical element can be configured to receive illumination light from a light source (e.g., from a microscope that is also used for viewing the image produced by the gonioscope 100) through the proximal surface 108 and to output the illumination light through the distal surface 106 into eye 200. The gonioscopic optical element 104 can be configured such that the target structure being imaged (e.g., the anterior chamber angle 204), such as the target structure positioned at a center portion of the image (e.g., center of the viewing portion 108*a*), receives more of the illumination light than other structures in the eye 200. This can provide improved illumination of the area being imaged (e.g., the anterior chamber angle 204, as can be seen in FIG. 7), as compared to other gonioscopes that direct most of the illumination light to a different portion of the eye (e.g., on to the iris 206, as can be seen in FIG. 8) that is not positioned at the center of the image.

Figure 11:
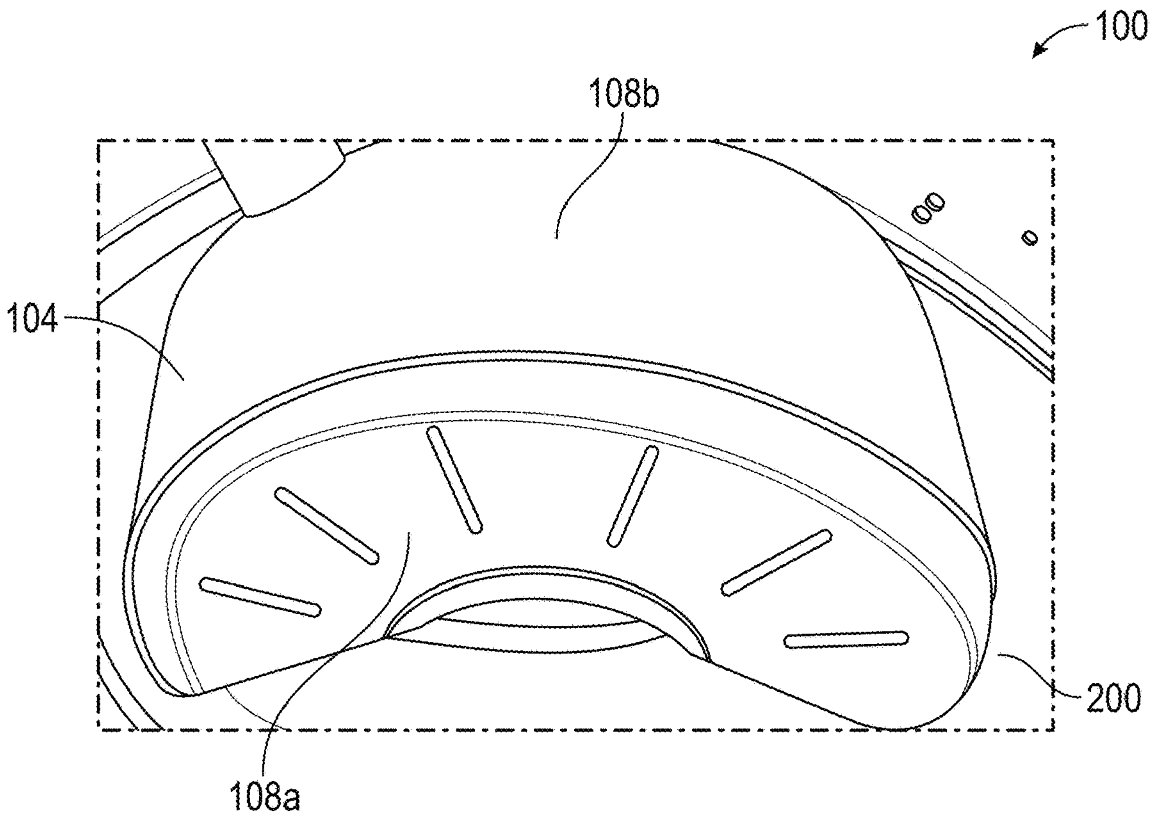
FIG. 11 shows a front view of an example embodiment of a gonioscopic optical element imaging a field of view.
Figure 12:
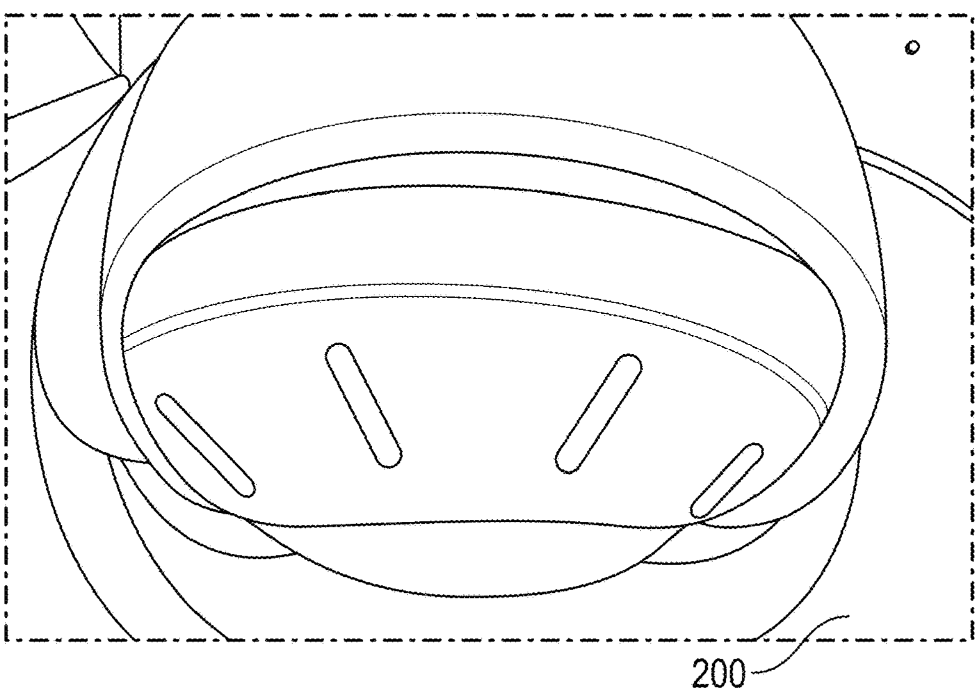
FIG. 12 shows a front view of another gonioscope optical element imaging a different field of view.

As can be seen by comparing FIGS. 11 and 12, the gonioscopic optical element 104 of gonioscope 100 can provide an increased field of view, as compared to other gonioscopes. The gonioscope 100 can provide a view of view of 90 degrees, 105 degrees, 120 degrees, 135 degrees, 150 degrees, or any values therebetween, or any range bounded by any combination of these values, although values outside these ranges may be used in some implementations. FIG. 12 shows a different gonioscope that provides a field of view of less than 90 degrees. The gonioscopic optical element 104 of the gonioscope 100 can provide magnification of 1.3×, of 1.2×, of 1.15×, of 1.1×, of 1.05×, of 0.9×, of 0.8×, of 0.7×, or no magnification, or any value therebetween, or any range bounded by any combination of these values, although magnifications outside these ranges can be used in some implementations. The proximal surface 108 can have a radius of curvature of 14 mm, 15 mm, 16 mm, 17 mm, 18 mm, 19 mm, 20 mm, or any values therebetween, or any ranges bounded by any combination of these values, although values outside of these ranges can be used in some implementations.

The gonioscopic optical element 104 can be made of a transparent material such as acrylic (e.g., poly(methyl methacrylate)), glass, quartz, silica, plastic, or other material that is suitably transparent so that light can propagate through the gonioscopic optical element 104 for imaging structure inside the eye 200. The transparent material does not need to transmit all the light that impinges on it. The transparent material can transmit at least sufficient amounts of light to produce an image as discussed herein, while some other light can be absorbed, or reflected, or otherwise not transmitted through the material. The handle 102 can be made of the same material as the gonioscopic optical element 104. The gonioscope 100 can be a single integrally formed piece that includes both the handle 102 and the gonioscopic optical element 104. The gonioscope 100 can be lightweight. The gonioscope 100 can weigh less than 5 grams, less than 4 grams, less than 3 grams, or between 1 gram and 2 grams, or any values therebetween, or any range bounded by any combination of these values, although weights outside of these ranges can be used in some implementations.

Figure 13:
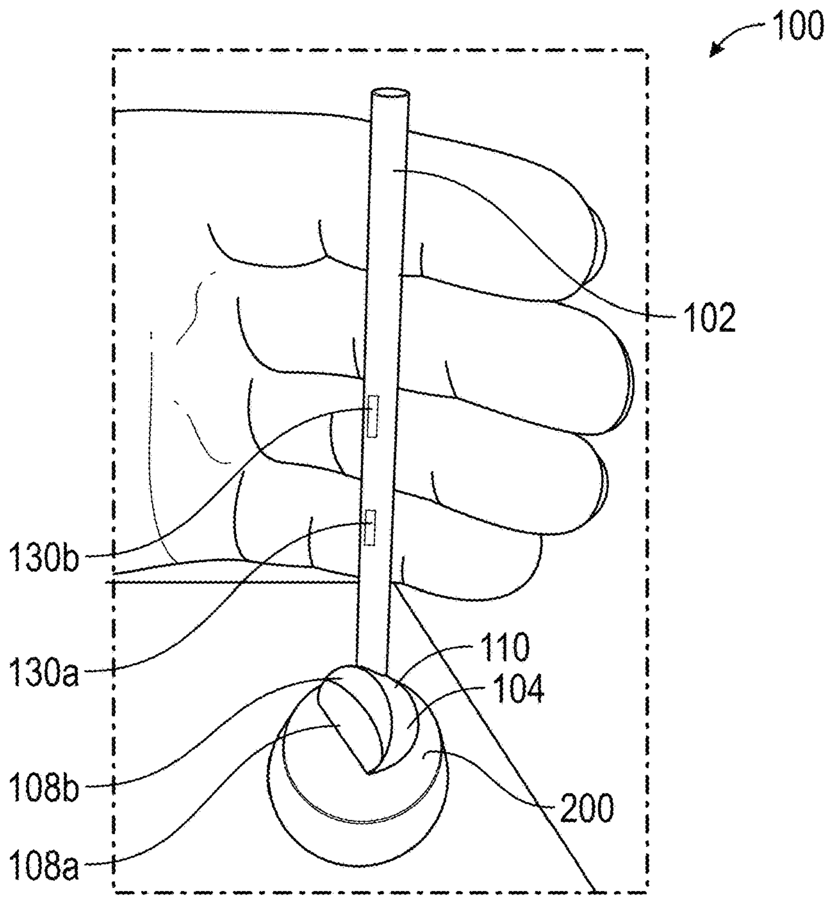
FIG. 13 shows an example embodiment of a gonioscope positioned on an eye and supported by a hand.
Figure 15:
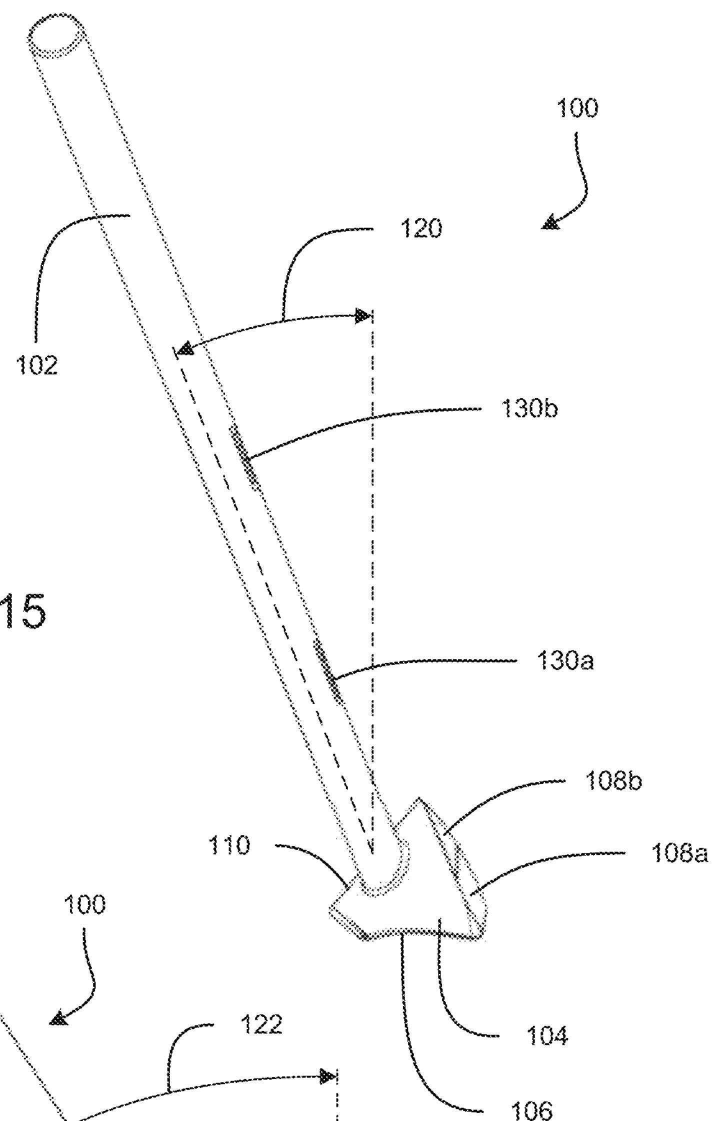
FIG. 15 shows a side view of an example embodiment of a gonioscope.
Figure 16:
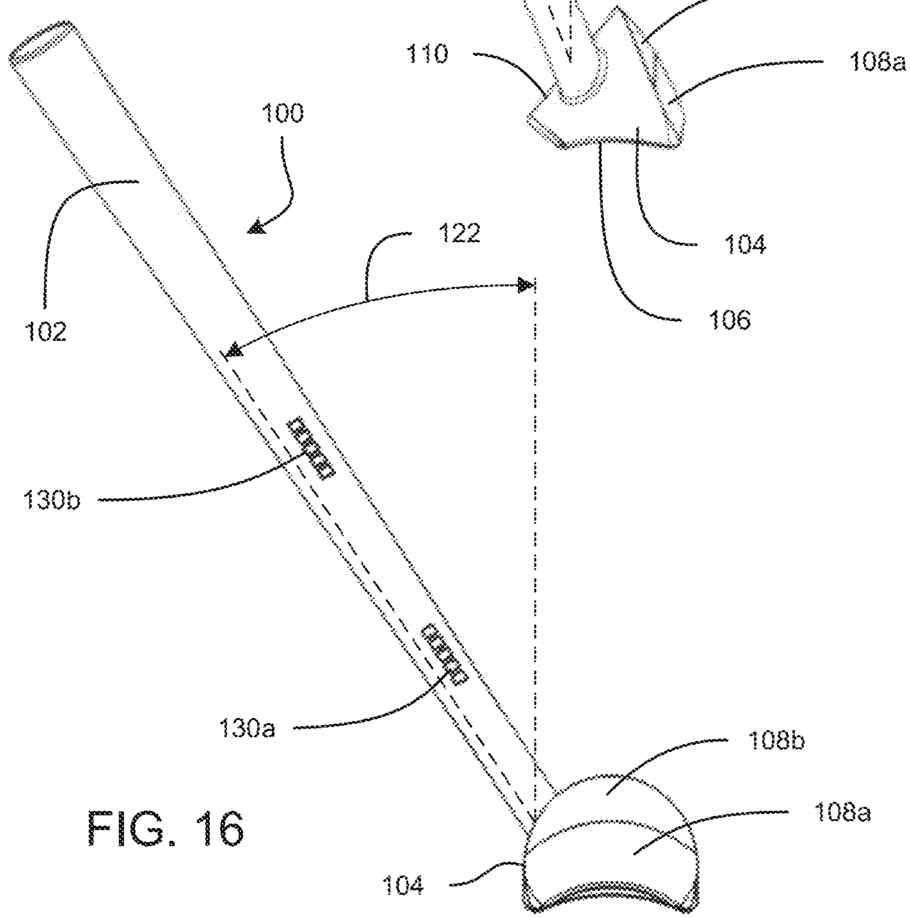
FIG. 16 shows a front view of an example embodiment of a gonioscope.

The handle 102 can be attached to the back surface 110 of the gonioscopic optical element 104. As discussed, the handle 102 can be integrally formed with the gonioscopic optical element 104. Alternatively, the handle 102 can be separately formed and coupled to the gonioscopic optical element 104, such as by an adhesive, a snap fit structure, a friction fit structure, an intermediate coupling mechanism, etc. The low weight, the low center of gravity, and/or the position of the handle 102 can enable the gonioscope 100 to remain in position on an eye 200 when the gonioscope handle 102 resting on a hand or other support positioned under the gonioscope handle 102, as can be seen in FIG. 13. Accordingly, a medical professional can grip the gonioscope handle 102 while positioning the gonioscope 100 (see FIG. 14), and the medical professional can open his/her hand to release the handle 102 and let the handle 102 rest on his/her hand (see FIG. 13) while viewing inside the eye 200 (e.g., during a surgical procedure). With reference to FIG. 15, when the gonioscope 100 is oriented with edges of the distal surface 106 flat along a horizontal plane, the handle 102 can be angled back from a vertical direction by an angle 120 that can be 40 degrees, 35 degrees, 30 degrees, 25 degrees less, 20 degrees, 15 degrees, 10 degrees, or any values therebetween, or any ranges bounded by any combination of these values, although values outside these ranges can be used in some instances. With reference to FIG. 16, when the gonioscope 100 is oriented with edges of the distal surface 106 flat along a horizontal plane, the handle 102 can be angled to the side from a vertical direction by an angle 122 that can be 45 degrees, 40 degrees, 35 degrees, 30 degrees, 25 degrees less, 20 degrees, 15 degrees, or any values therebetween, or any ranges bounded by any combination of these values, although values outside these ranges can be used in some instances. The handle 102 can be angled to the right side of the gonioscope 100 (see FIG. 16), such as to be operated using the left hand (see FIG. 13). The handle 102 can be angled to the left side of the gonioscope 100, such as to be operated using the right hand. In some embodiments, the handle 102 is not angled to the side, and an ambidextrous handle can extend upward, such as from a center of the gonioscopic optical element 104 for use by either the right hand or left hand.

Figure 14:
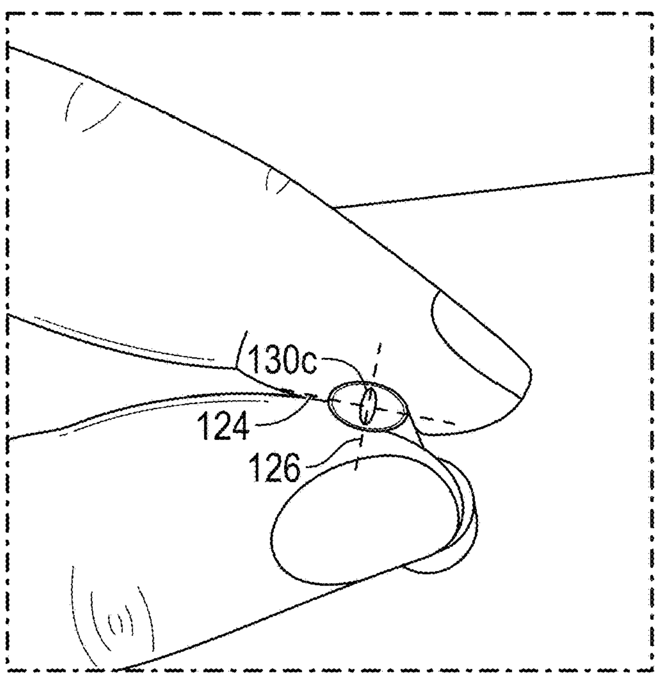
FIG. 14 shows the handle of an example embodiment of a gonioscope being held.
Figure 17:
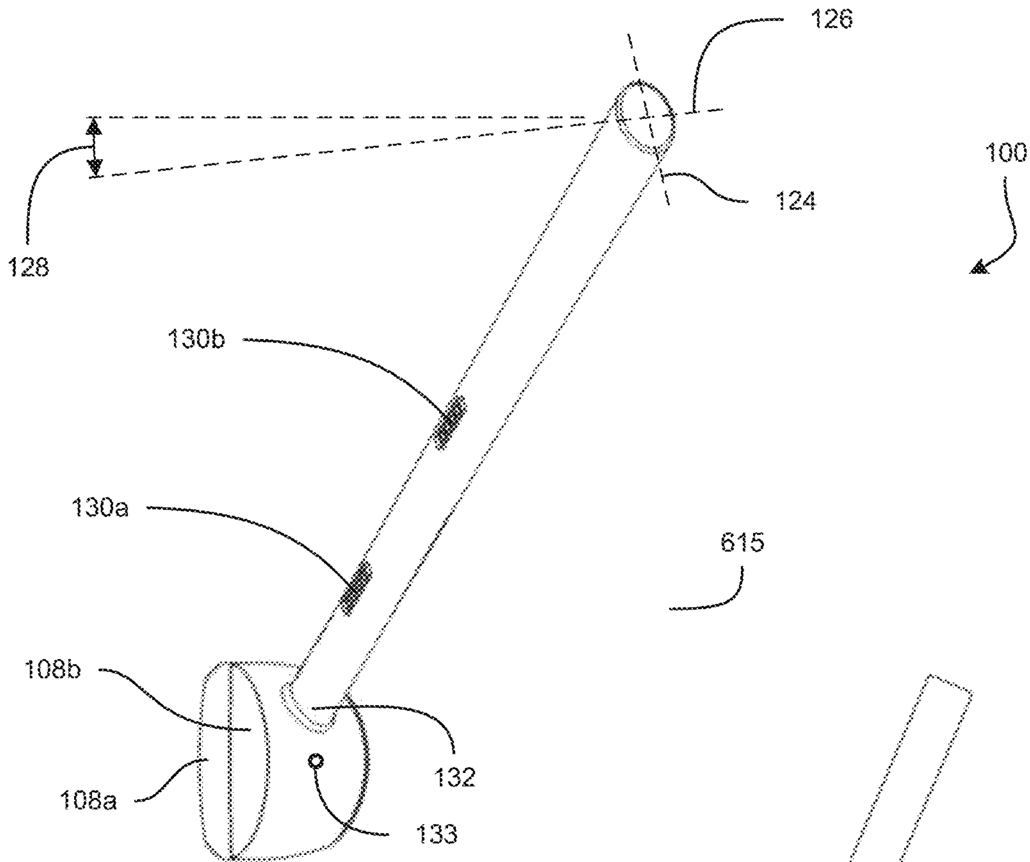
FIG. 17 shows a top view of an example embodiment of a gonioscope.

The handle 102 can have an elliptical cross-sectional shape, as can be seen in FIGS. 14 and 17. The elliptical shape of the handle 102 can encourage proper positioning of the gonioscope 100 when held by the user, such as between the thumb and index finger, as shown in FIG. 14. If the user holds the handle 102 with the major axis 124 extending towards the fingers, applying pressure to the handle 102 can cause the handle 102 to rotate so that the fingers move closer together with the minor axis 126 extending towards the fingers, as shown in FIG. 14. The orientation of the minor axis 126 can be configured so that when the user holds the gonioscope 100 in front of the user (e.g., between the thumb and forefinger) with the wrist and fingers in a natural position, the elliptical shape of the handle 102 encourages the gonioscope 100 to be oriented with the proximal surface 108 of the gonioscopic optical element 104 facing towards the user. With reference to FIG. 17, the minor axis 126 of the elliptical handle 102 can be angled towards the gonioscopic optical element 104 by an angle 128 with respect to an axis extending from front to back. The angle 128 can be 3 degrees, 4 degrees, 5 degrees, 6 degrees, 7 degrees, 8 degrees, 9 degrees, 10 degrees, 11 degrees, 12 degrees, 13 degrees, 14 degrees, 15 degrees, or any values therebetween, or any ranges bounded by any combination of these values, although values outside these ranges can be used in some implementations.

Figure 18:
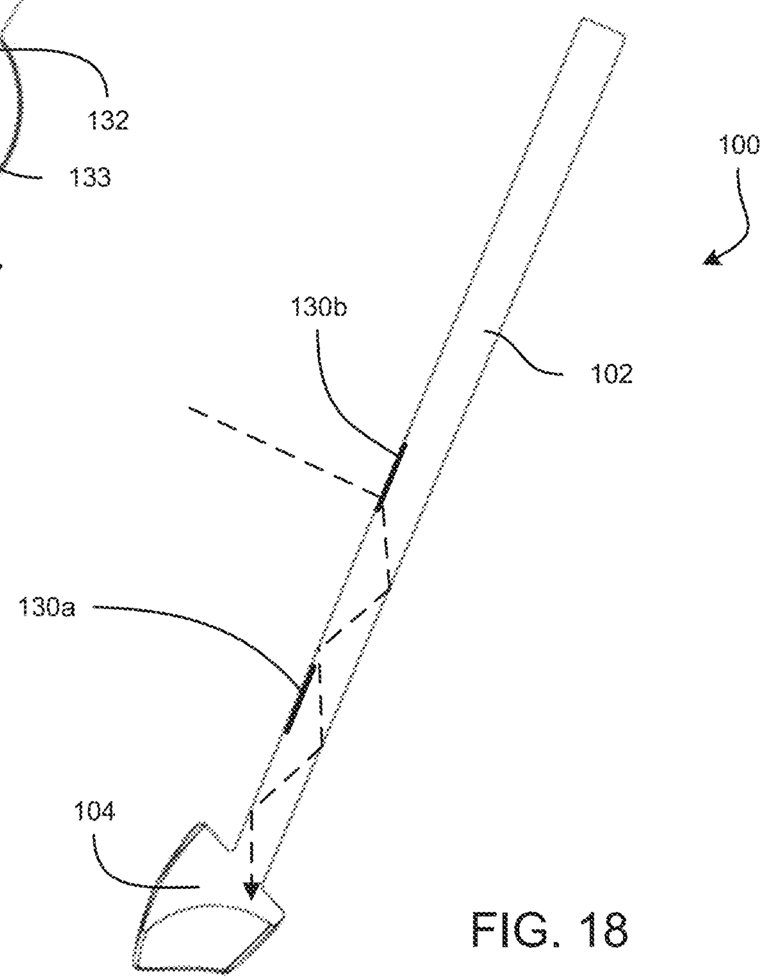
FIG. 18 shows a cross-sectional view of an example embodiment of a gonioscope taken through the handle.

In some embodiments, light can be directed from the handle 102 into the gonioscopic optical element 104. This light can facilitate illumination of the eye structure being imaged. FIG. 18 is a cross-sectional view of the gonioscope 100 taken along a center of the handle 102. As can be seen in FIG. 18, for example, light can enter the handle 102 and can propagate along the handle by total internal reflection to the gonioscopic optical element 104. The handle 102 and gonioscopic optical element 104 can be integrally made of the same material, so that the light can transition seamlessly from the handle 102 to the gonioscopic optical element 104, as can be seen in FIG. 18. In some embodiments, the handle 102 and gonioscopic optical element 104 can be separately formed and optically coupled to enable light to propagate from the handle 102 to the gonioscopic optical element 104, such as by an optical adhesive, an index matching material, etc. In some embodiments, scattering elements (not shown) can scatter the light, such as at the transition from the handle 102 to the gonioscopic optical element 104 to facilitate illumination of the structure in the eye 200.

In some embodiments, light can enter the handle 102 of the gonioscope 100 at one or more light entry areas 130*a-c*. In the example embodiments shown in FIGS. 13 and 15-18, the handle can include two light entry areas 130*a* and 130*b*. The one or more light entry areas 130*a-b* can be positioned on the front side of the handle 102. In some cases, light from a microscope or other illumination device can illuminate the gonioscope 100 from the front side. The light can be directed into the gonioscopic optical element 104, such as through the proximal surface 108, as discussed herein. As can be seen in FIG. 18, the light can also enter the handle 102 at the one or more light entry areas 103*a-b*. In some embodiments, light entry areas can be positioned at other locations on the handle 102, such as to enable ambient light to enter the handle 102. As shown in FIG. 14, in some embodiments, the handle 102 can include a light entry area 130*c* on the top end surface of the handle 102, which can allow light to enter the handle 102 and propagate to the gonioscopic optical element 104 by total internal reflection. Light entry areas can be positioned at other locations as well, such as on the back or other sides of the handle 102. In some embodiments, light can enter the handle through the surfaces of the handle 102 that do not have dedicated light entry areas 103*a-c*. Light can refract as it passes through a surface of the handle 102 and can be redirected by the refraction so that the light propagates along the handle to the gonioscopic optical element 104 by total internal reflection. The light entry areas 130*a-c* can have one or more angled surfaces, such as a saw tooth structure, that are configured to refract light, such as from a microscope or other illumination device directing light to the front side of the gonioscope 100, so that the refracted light propagates by total internal reflection to the gonioscopic optical element 104, as can be seen for example in FIG. 18.

In some embodiments, the gonioscope 100 can be configured to provide an optical fixation point, which can facilitate alignment and/or steadying of the eye 200. An optical fixation point can be used to help a patient orient their eye to align with the gonioscopic optical element 104, a microscope, a surgical tool, a measurement device, a medical professional, etc. A subject can focus his/her vision on the optical fixation point to facilitate keeping the eye steady during a medical procedure (e.g., surgery or a diagnostic measurement). In some procedures, a subject's head it ordinarily tilted at an angle to provide the appropriate orientation of the eye 200 for the procedure. In some cases, a subject can focus on the optical fixation point to provide a reliable tilting of the eye 200 relative to the head, so that the patient can avoid tilting the head during the procedure, which can result in improved patient comfort. The optical fixation point can be used with the gonioscopes discussed herein during procedures and treatments such as, for example, glaucoma surgery (e.g., minimally invasive glaucoma surgery (MIGS), laser trabeculoplasty, fundus laser, vitrectomy laser, and suture lysis optics where ocular retention and eye/lens stabilization would be beneficial).

In some embodiments, light can be directed into the gonioscopic optical element 104 from the handle 102, as discussed herein, and this light can produce a bright spot that can be used as the optical fixation point. The subject can focus his or her vision on the bright spot to stabilize and/or align the eye 200. The handle 102 can join the gonioscopic optical element 104 at a joint location 132 that corresponds to the desired orientation of the eye 200, so that the bright spot formed by light entering the gonioscopic optical element 104 through the joint location 132 is at a location the aligns with the vision axis of the eye 200 when the eye is properly aligned with the gonioscope 100. In some embodiments, the joint location 132 of the handle 102 to the gonioscopic optical element 104 can be at a different location than shown in FIG. 17, in order to produce an optical fixation point. For example, the joint location can be located at position 133 shown in FIG. 17. The joint location can be along a center plane of the gonioscopic optical element 104. The joint location can be at a location 133 that causes the eye 200, when focused on the optical fixation point, to be angled relative to the vertical direction by an angle of 15 degrees, 20 degrees, 25 degrees, 30 degrees, 35 degrees, 40 degrees, 45 degrees, or at any angle between these values, or any range bounded by any combination of the these values, although values outside these ranged can be used in some instances.

Figure 19:
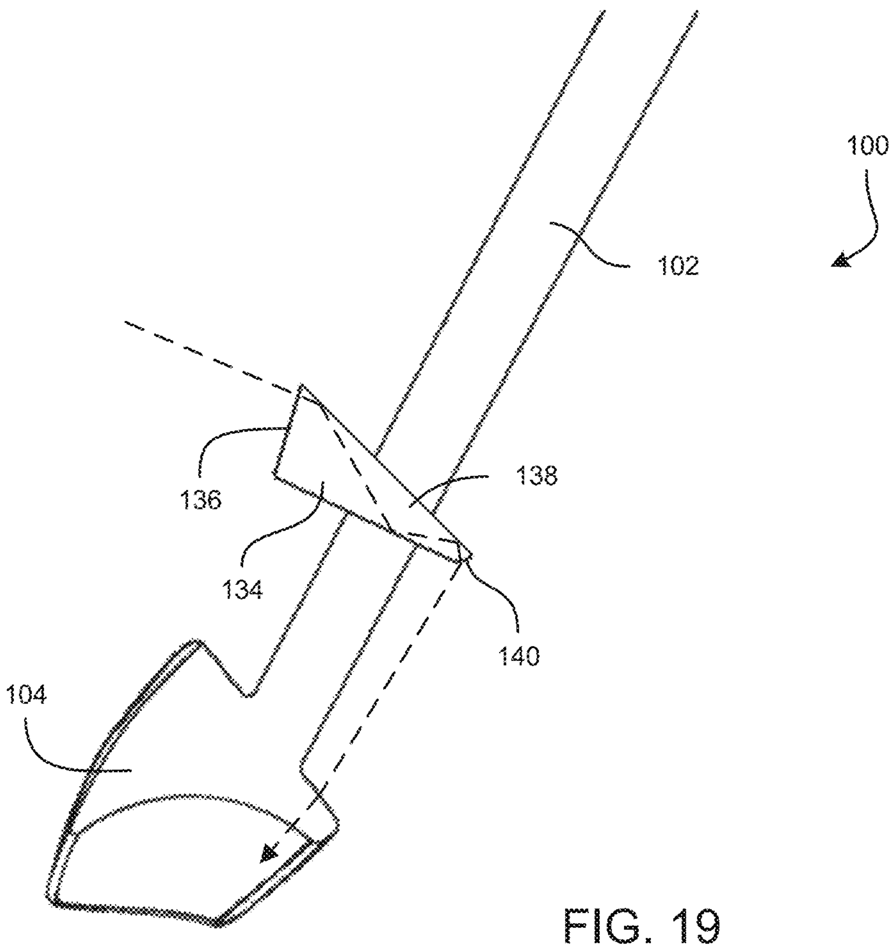
FIG. 19 shows a partial-cross sectional view of an example embodiment of a gonioscope that includes a light guide for providing an optical fixation point.
Figure 20:
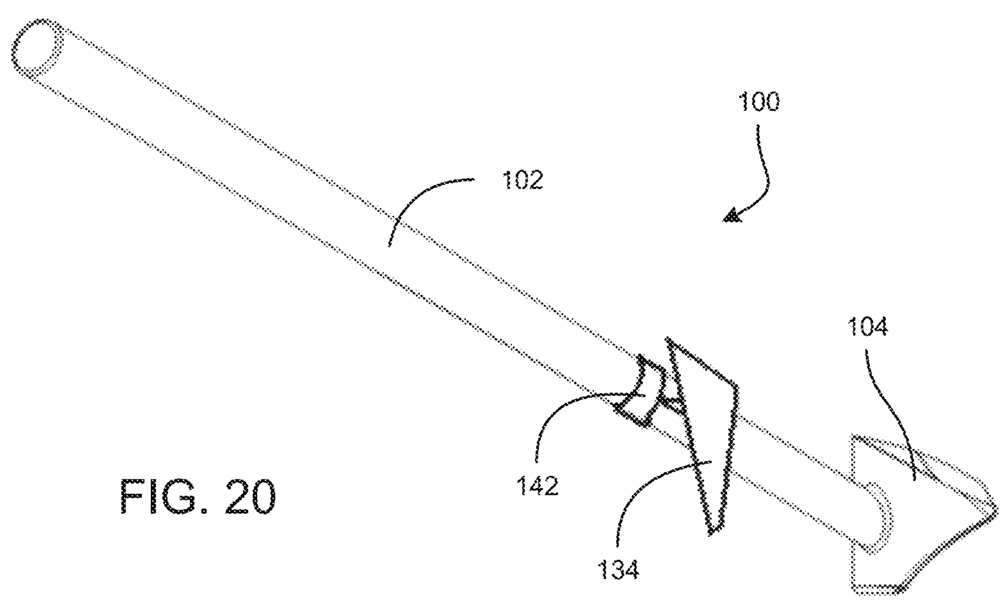
FIG. 20 shows another example embodiment of a gonioscope that includes a light guide for providing an optical fixation point.

In some embodiments, the gonioscope 100 can include an optical fixation point light guide 134. With reference to FIG. 19, the light guide 134 can have a light entry surface 136, which can face forward, such as to receive light from a microscope or other illumination device. A light propagation region 138 can propagate the light (e.g., by total internal reflection) to an illumination point 140, where the light can be redirected (e.g., by refraction or scattering) to the eye (e.g., through the gonioscopic optical element 104 in some embodiments). The illumination point 140 can be positioned at a location that corresponds to the desired orientation of the eye 200, so that a bright spot formed by from the light guide 134 is at a location that aligns with the vision axis of the eye 200 when the eye is properly aligned with the gonioscope 100. In some embodiments, the propagation region 138 can be tapered so that the light guide 134 gets thinner from the light entry surface 136 to the illumination point 140. The light entry surface 136 can gather a relatively large amount of light and the tapered light propagation region 138 can concentrate that light to the illumination point 140, so that the illumination point 140 appears visible to the subject as a bright spot. The light guide 134 can be made of a different material than the handle 102, such as a plastic or glass material, which in some embodiments can have a higher index of refraction than the handle 102. In some embodiments, the light guide 134 can extend through the handle 102. For example a bore can be formed in the handle 102, and the light guide 134 can extend through the bore. In some cases, an adhesive can secure the light guide 134 to the handle 102. The adhesive can have a lower index of refraction than the material of the light guide 134. In some embodiments, the light guide 134 can propagate light outside the handle 102, instead of through the handle 102. For example, with reference to FIG. 20, the light guide 134 can attach to the handle 102, such as be a clip 142 or friction fit, etc., so that the light guide 134 is suspended next to the handle 102. The light guide 134 can be shaped to position the illumination point behind the handle 102, for example.

Various other types of optical fixation points can be used, such as those described in WO 2016/154066.

The light diffusing portion 108*b* can diffuse light from the optical fixation point to impede the medical professional from seeing the optical fixation point, which can be distracting, as discussed herein. The light diffusing portion 108*b* can impede the light of the optical fixation point from reflecting off the proximal surface 108 to make a secondary bright spot, which could be distracting or confusing for the subject.

Figure 21:
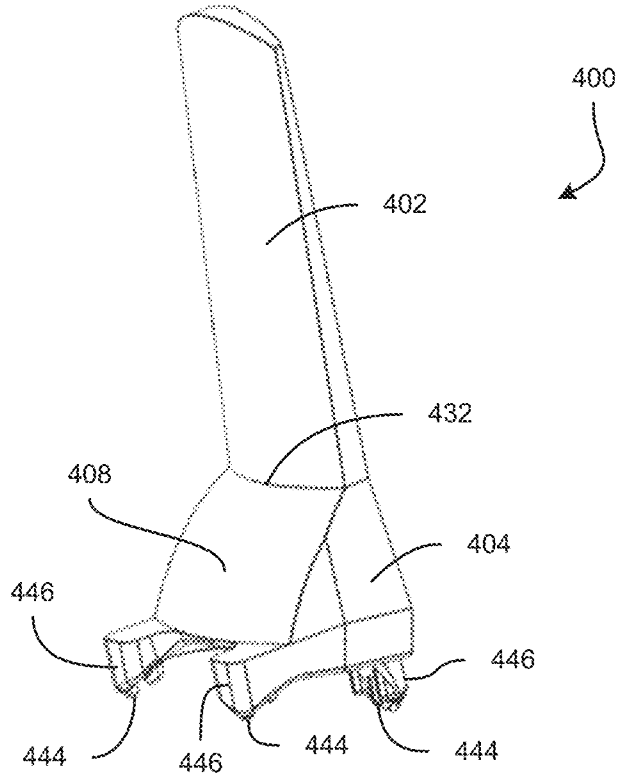
FIG. 21 is a top-front perspective view of an example embodiment of a gonioscope.
Figure 22:
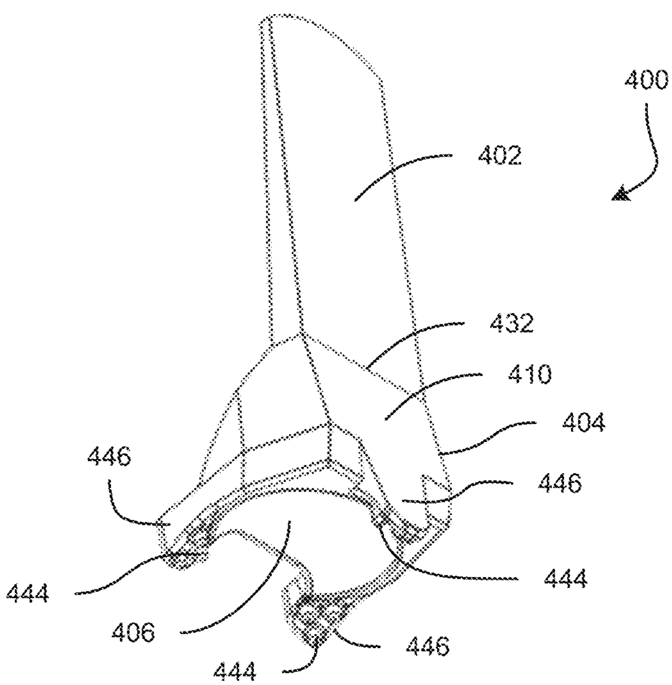
FIG. 22 is a bottom-rear perspective view of the example embodiment of a gonioscope.
Figure 23:
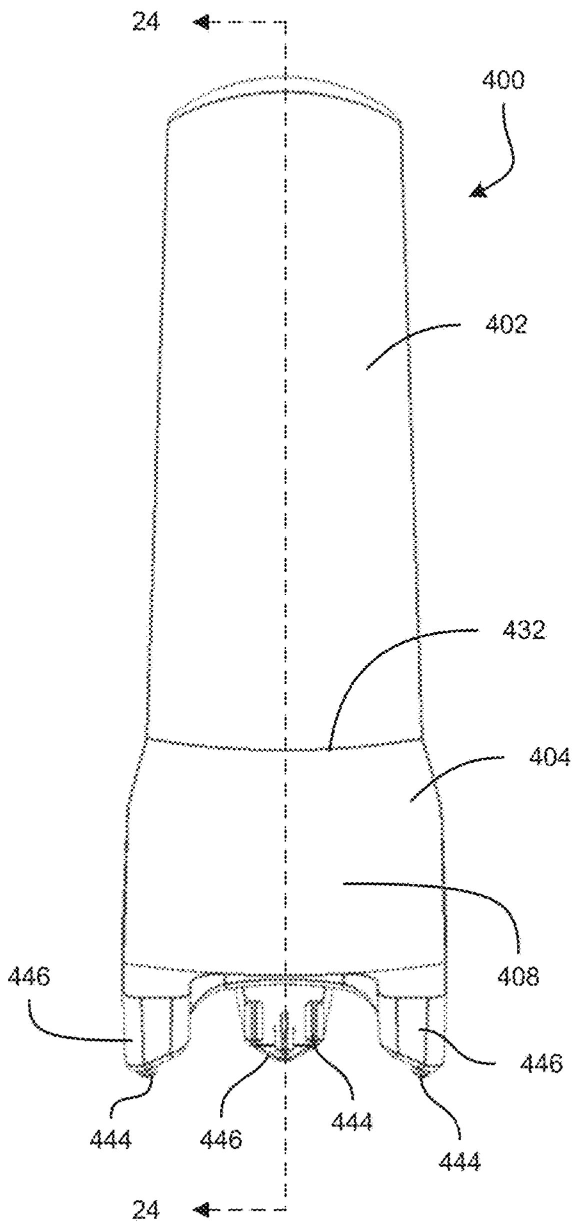
FIG. 23 is a front view of an example embodiment of a gonioscope.
Figure 24:
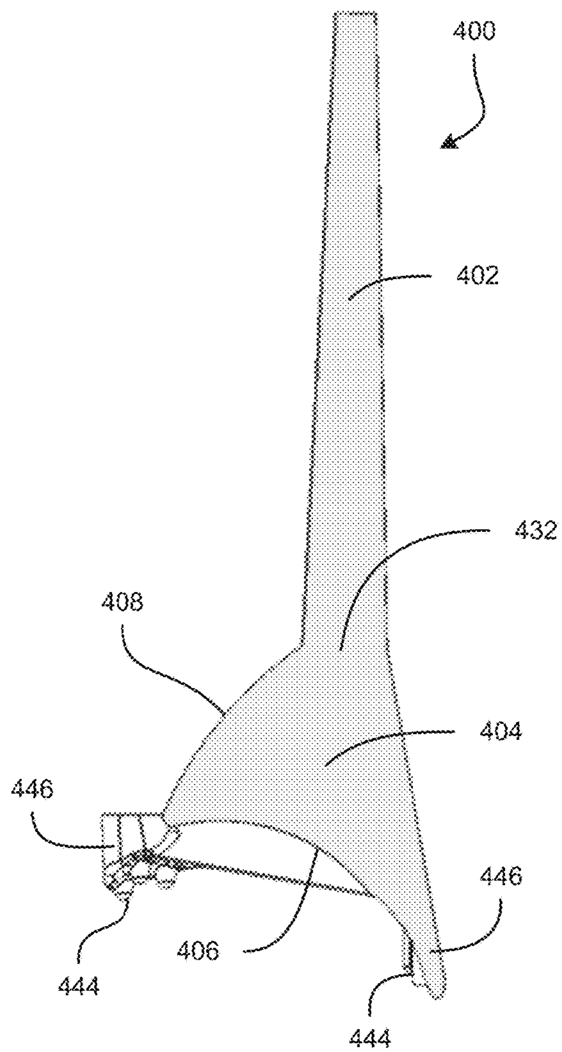
FIG. 24 is a cross-sectional view of an example embodiment of a gonioscope.

FIG. 21 is a top-front perspective view of an example embodiment of a gonioscope 400. FIG. 22 is a bottom-rear perspective view of the example embodiment of a gonioscope 400. FIG. 23 is a front view of the example embodiment of a gonioscope 400. FIG. 24 is a cross-sectional view of the example embodiment of a gonioscope 400 taken at plane 24-24 shown in FIG. 23. The gonioscope 400 can have features that are the same as, or similar to, features of the gonioscope 100. Many features discussed in connection with the gonioscope 100 can apply also to the gonioscope 400 and are not discussed in detail in connection with the gonioscope 400 for sake of brevity.

The gonioscope 400 can include a handle 402 and a gonioscopic optical element 404. The gonioscopic optical element 404 can include a distal surface 406 and a proximal surface 408, similar to the gonioscope 100. In some embodiments, the proximal surface 108 can have a generally rectangular profile from the front, as can be seen in FIG. 23, which can facilitate gathering of light into the gonioscopic optical element 404 to illuminate the eye 200. In some embodiments, the gonioscope 400 can have flat surfaces, other than the curved distal contact surface 406 and the curved proximal surface 408, which is used for viewing the image of the eye 200. The gonioscopic optical element 404 can have a back surface 410 that is flat. The back surface 410 can reflect light (e.g., by total internal reflection or using a reflective material such as a metal coating applied to the outside of the gonioscope 400 at the back surface 410) to redirect light into the eye 200, to illuminate the target structure being imaged. The flat shape of the back surface 410 can facilitate distributing the light across the imaging are of the eye 200, as opposed to focusing the light as can occur with a curved back surface of the gonioscopic optical element 404.

The gonioscope 400 can have one or more retention elements 444, which can be configured to engage tissue of the eye 200, such as scleral tissue around the cornea, to retain the gonioscope 400 in positioned relative to the eye 200. The one or more retention elements 444 can be positioned on the distal side of one or more arms 446. The one or more retention elements 444 and the one or more arms 446 can include features that are the same as, or similar to features of the retention elements and arms described in the WO 2016/154066 publication, which is incorporated herein by reference. Although not shown in the example embodiments illustrated in the Figures, the gonioscope 100 can include one or more retention elements and/one or more arms, similar to those disclosed in connection with the gonioscope 400.

The handle 402 can connect to the gonioscopic optical element 404 at a joint location 432 that extends across the full length of the top edge of the gonioscopic optical element 404, or across at least 90%, at least 80%, at least 70%, at least 60%, or at least 50% of the top edge of the gonioscopic optical element 404, or any values therebetween, or any ranges bounded by any combination of these values, although values outside these ranges can be used in some instances. The wide joint location 432 can provide improved strength to the connection between the handle 402 and the gonioscopic optical element 404, and can impede the gonioscope 400 from breaking, such as when being used to restrain the eye using the retention elements 444.

The handle 402 can extend straight upward from the gonioscopic optical element 404, not angled to either the left side or right side, so that the handle is ambidextrous for use by either the right hand or left hand. The gonioscope 400 can be symmetrical across the plane 24-24 of the cross-sectional view of FIG. 24, which extends across the middle of the gonioscope 400. The right and left sides of the gonioscope 400 can be symmetrical to each other. The gonioscope 400 can be configured such that the handle 402 extends generally vertically upward when positioned on the eye oriented for viewing the anterior chamber angle. The handle 402 can be angled by 20 degrees, 15 degrees, 10 degrees, 5 degrees, or 0 degrees relative to the vertical direction, or any values therebetween, or any ranges bounded by any combination of these values, although values outside these ranges can be used in some instances. The center of gravity of the gonioscope 400 can be positioned generally above the eye 200, which can facilitate maintenance of the gonioscope 400 at the proper position relative to the eye 200 with little input from the medical professional. In some cases the medical professional can release the gonioscope 400, and the gonioscope 400 can stay in place even when not being held or supported by the medical professional (e.g., hands free). The one or more retentions elements 444 and/or the one or more arms 446 can provide a base for the gonioscope 400 that is larger than the distal surface 406 of the gonioscopic optical element 404, to facilitate stabilizing of the gonioscope 400. The handle 402 of the gonioscope 400 can be positioned to be held by the medical professional in a natural position (e.g., without needing muscles to flex to maintain the position) when aligned with the eye. Some gonioscopes can require the medical professional's hand to rotate outwardly to hold the handle of the gonioscope in position, which can be difficult to maintain especially over long periods of time such as during a medical procedure.

Figure 25:
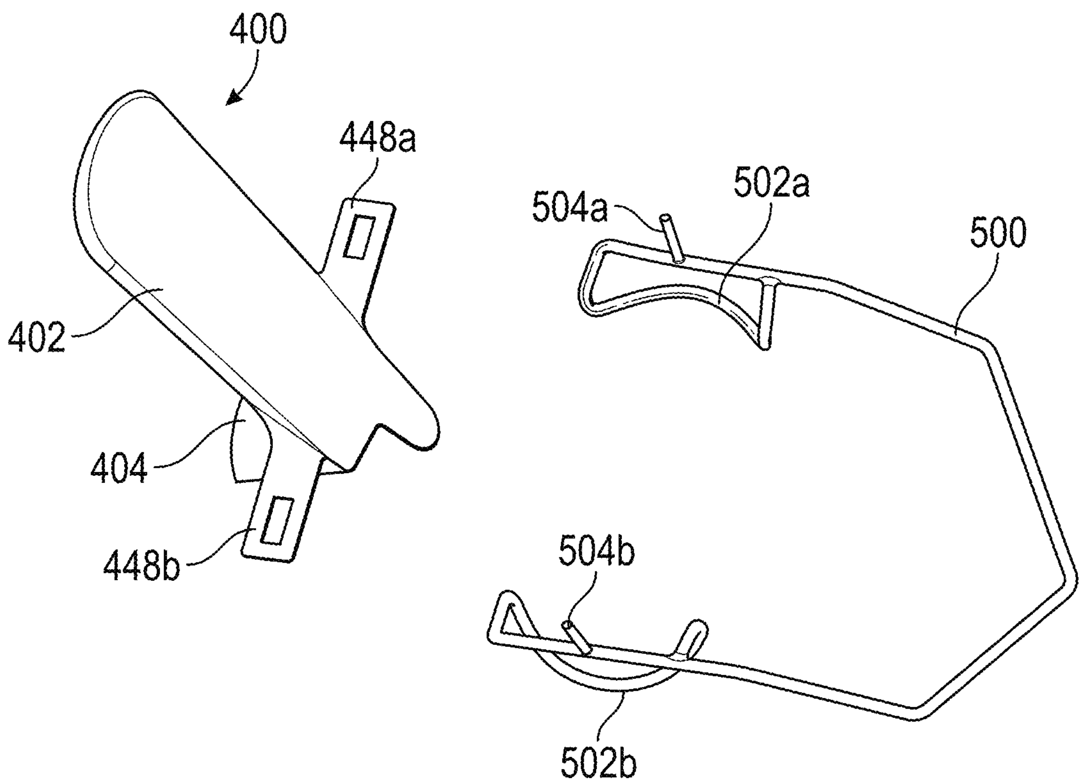
FIG. 25 shows an example embodiment of a gonioscope and a lid speculum.
Figure 26:
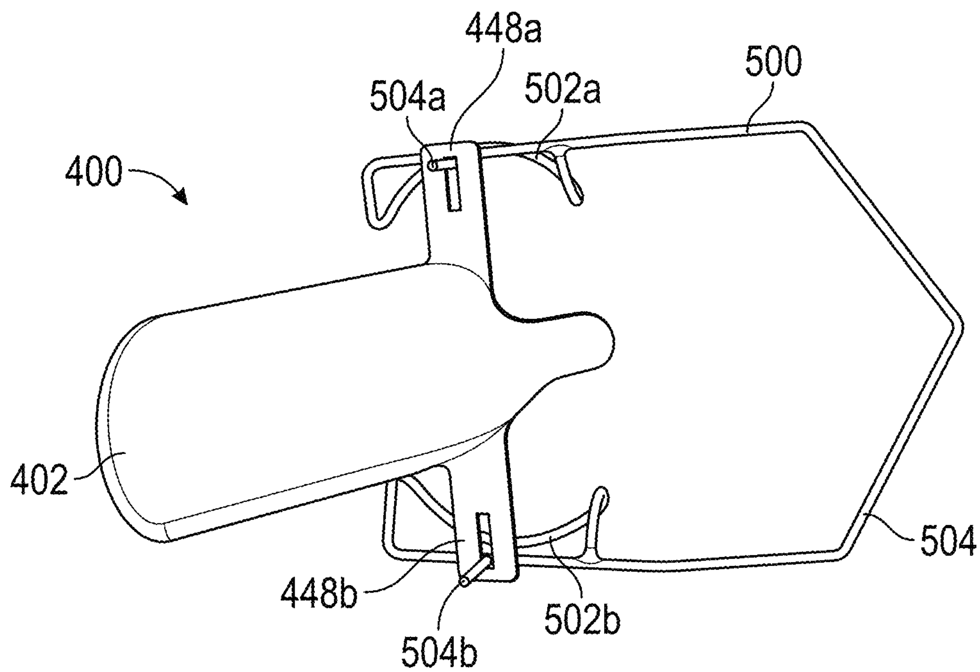
FIG. 26 shows an example embodiment of a gonioscope attached to a lid speculum.

In some embodiments, the gonioscope 400 can be configured to attach to a lid speculum 500. FIG. 25 shows the gonioscope 400 and lid speculum 500 separate from each other. FIG. 26 shows the gonioscope 400 coupled to the lip speculum 500. The gonioscope 400 can include one or more coupling elements that are configured to attach to attachment portions of the lid speculum 500. The lid speculum can have a right-side eye engagement piece 502*a* and a left-side eye engagement piece 502*b*, which are configured to engage the upper and lower eyelids. A biasing member 504 can bias the right-side eye engagement piece 502*a* and the left-side eye engagement piece 502*b* away from each other, to hold the eye 200 of a subject open. The lid speculum 500 can have attachment portions, such as posts 504*a* and 504*b* that are configured to attach to the gonioscope 400. The right post 504*a* can extend upward from the right-side eye engagement piece 502*a*. The left post 504*b* can extend upward from the left-side eye engagement piece 502*b*. The gonioscope 400 can have a right wing 448*a* that extends (e.g., horizontally) from the right side of the gonioscope 400 and a left wing 448*b* that extends (e.g., horizontally) from the left side of the gonioscope 400. The right wing 448*a* and the left wing 448*b* can have holes that are configured to receive the respective right post 504*a* and left post 504*b*. The holes in the wings 448*a-b* can be elongate slots extending to the right and left, to provide a range of motion for the posts 504*a-b* to move within the holes as the right-side eye engagement piece 502*a* and the left-side eye engagement piece 502*b* move relative to each other. The attachment of the gonioscope 400 to the lid speculum 500 can stabilize the gonioscope 400 on the eye 200, such as when a medical professional releases the gonioscope for hands-free use of the gonioscope 400. The gonioscope 100 can also be configured to couple to a lid speculum, such as using wings or other coupling members.

Figure 27:
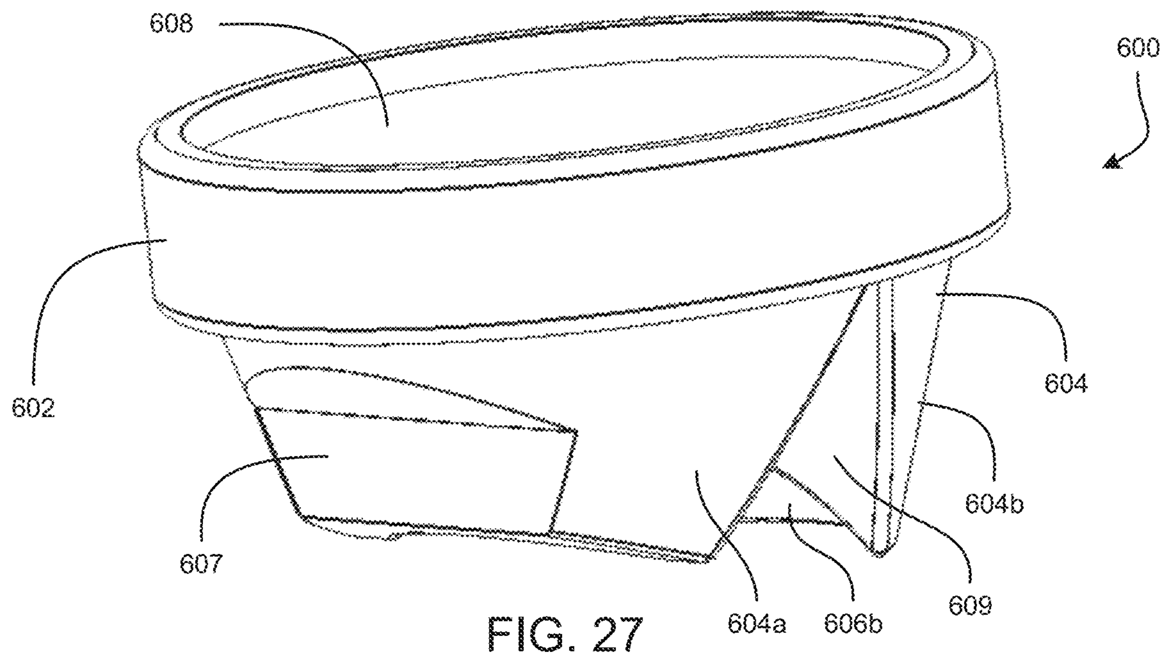
FIG. 27 shows a top-front perspective view of an example embodiment of a gonioscope.
Figure 28:
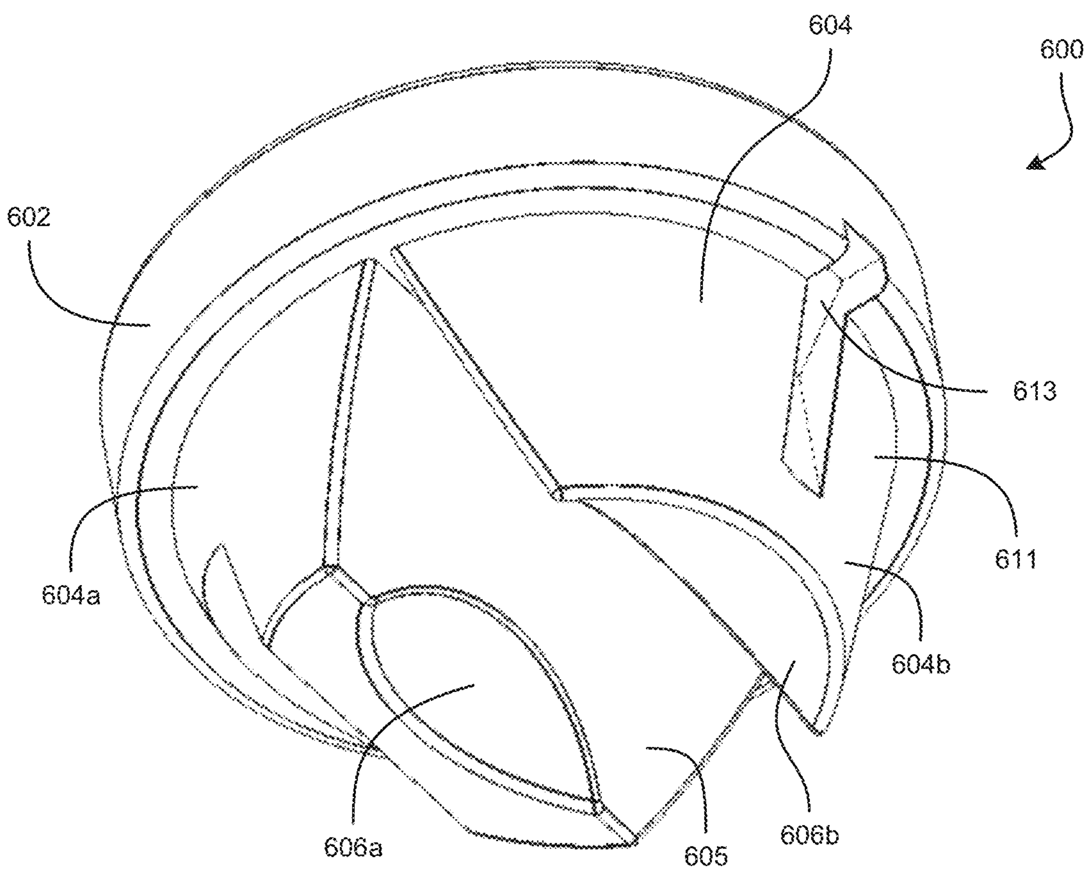
FIG. 28 shows a bottom-rear perspective view of an example embodiment of a gonioscope.
Figure 29:
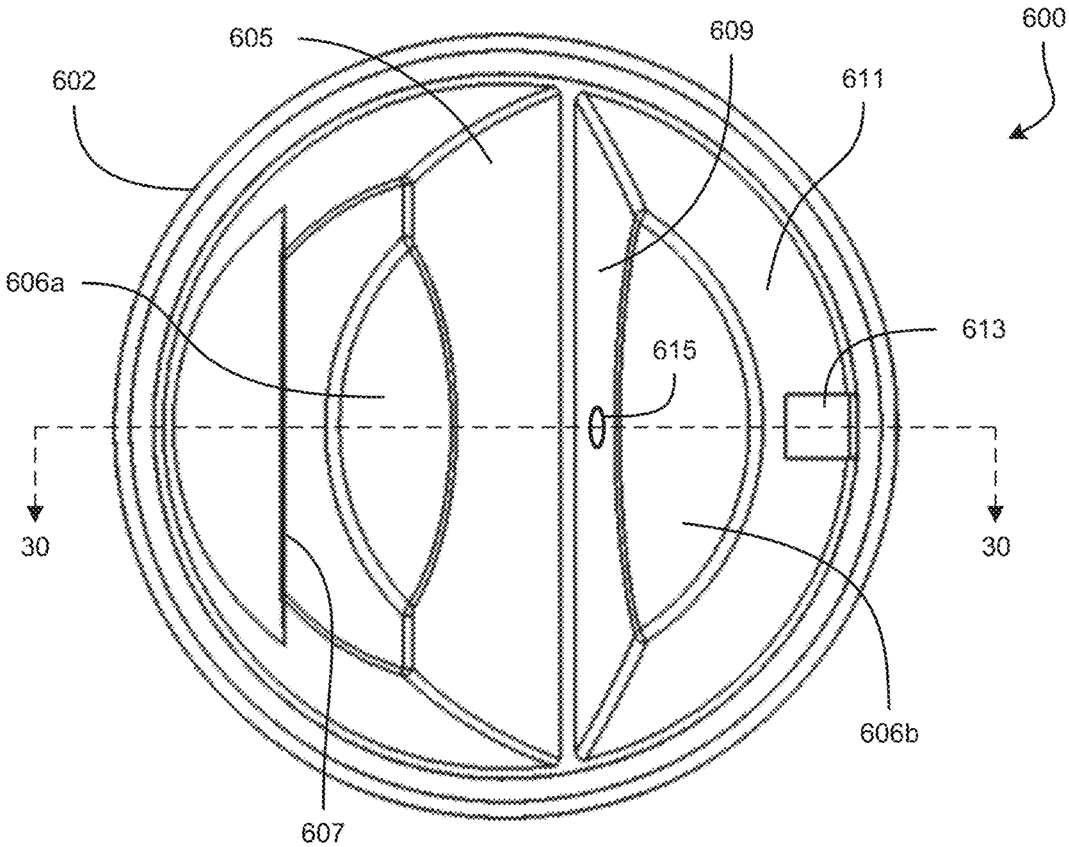
FIG. 29 is a top-down view of an example embodiment of a gonioscope, where the proximal surface is shown transparent to illustrate the surfaces inside the gonioscope.
Figure 30:
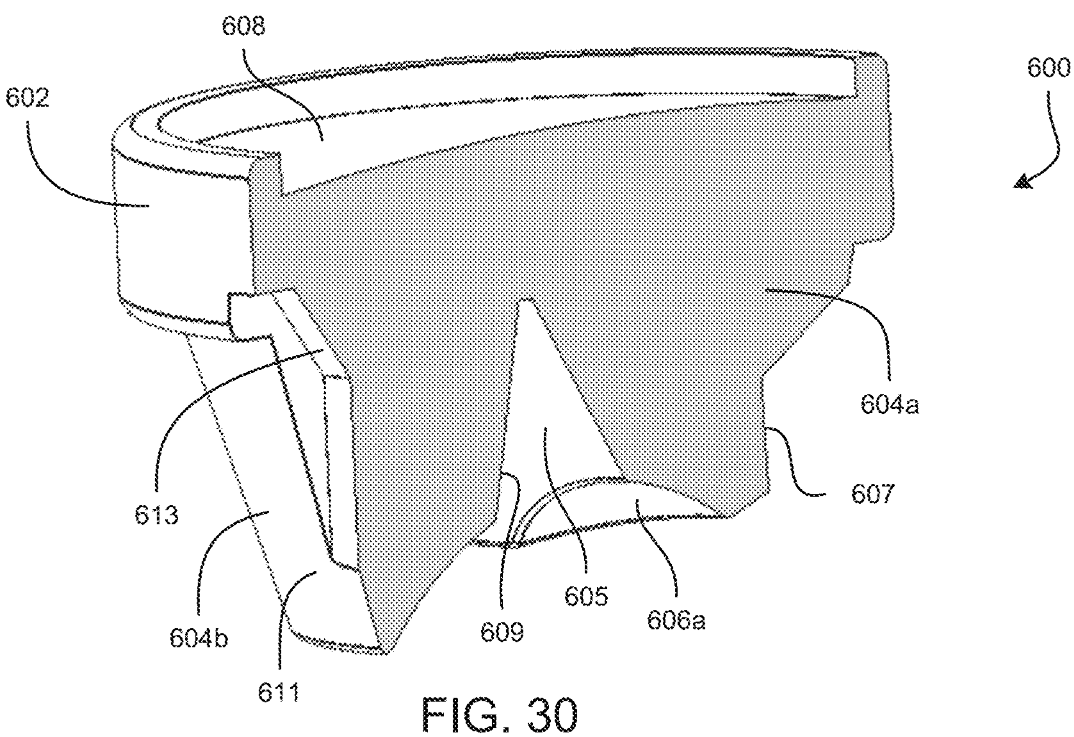
FIG. 30 is a perspective, cross-sectional view of an example embodiment of a gonioscope.
Figure 31:
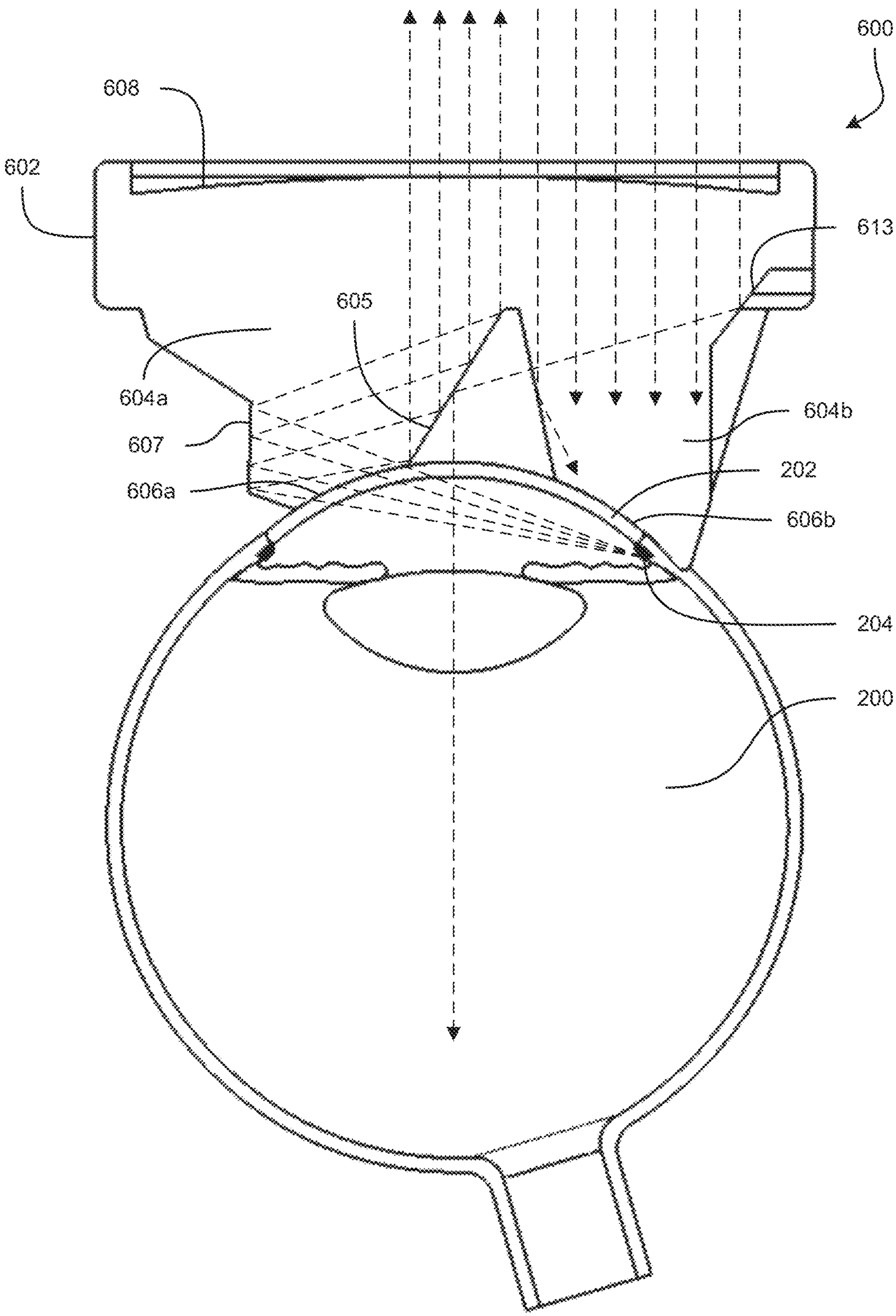
FIG. 31 is a cross-sectional view of an example embodiment of a gonioscope positioned on an eye.

FIG. 27 shows a top-front perspective view of an example embodiment of a gonioscope 600. FIG. 28 shows a bottom-rear perspective view of an example embodiment of a gonioscope 600. FIG. 29 is a top-down view of an example embodiment of a gonioscope 600, where the proximal surface is shown transparent to illustrate the surfaces inside the gonioscope 600. FIG. 30 is a perspective, cross-sectional view of an example embodiment of a gonioscope 600. FIG. 31 is a cross-sectional view of an example embodiment of a gonioscope 600 positioned on an eye 200. The gonioscope 600 can have features that are the same as, or similar to, features of the other gonioscopes 100 and 400 disclosed herein. Many features discussed in connection with the gonioscopes 100 and 400 can apply also to the gonioscope 600 and are not discussed in detail in connection with the gonioscope 600 for sake of brevity.

The gonioscope 600 can include a handle 602 and a gonioscopic optical element 604. The handle 602 can be a gripping portion positioned at the periphery of the upper portion of the gonioscope 600. The handle 602 can extend around all or a portion of the periphery of the gonioscopic optical element 604 (e.g., at an upper end or portion of the gonioscopic optical element 604). The handle 602 can be annular, although other shapes can be used such as a square or rectangular handle 602. In some embodiments, the handle 602 and the gonioscopic optical element 604 can be integrally formed of the same material, such as by injection molding of a single piece. The gonioscopic optical element 604 can be made of a transparent material such as acrylic (e.g., poly(methyl methacrylate)), glass, quartz, silica, plastic, or other material that is suitably transparent so that light can propagate through the gonioscopic optical element 604 for imaging structure inside the eye 200. The handle 602 can be made of the same material as the gonioscopic optical element 604. In some embodiments, the handle 602 can include a textured surface, such as the radially outward facing surface, to facilitate gripping by the user. In some embodiments, the handle 602 can include a different material than the gonioscopic optical element 604. For example, the handle 602 can include an elastomeric material to facilitate gripping of the handle 602 by the user. A sleeve (not shown) can fit over a portion of the gonioscope to form the handle, and can include an elastomeric material to facilitate gripping of the handle 602. In some embodiments, the handle 602 can include a shaft, similar to the handles 102 and 402 disclosed herein. In some embodiments, the handle 602 can be omitted. For example, a user can grip the sides of the gonioscopic optical element 604 directly, or the gonioscope 600 can be configured for hands-free operation.

The gonioscopic optical element 604 can include a first portion 604*a* and a second portion 604*b*, which can be separated such as by a gap (e.g., and air gap) or an intermediate material that is different than the material of the gonioscopic optical element. The space between the first portion 604*a* and the second portion 604*b* of the gonioscopic optical element 604 can increase in width along the downward direction. In some embodiments, the first portion 604*a* and the second portion 604*b* of the gonioscopic optical element 604 can be joined at an upper end, and can diverge away from each other in the downward direction. The first portion 604*a* can be configured to export an image of the structure inside the eye 200 (e.g., the anterior chamber angle 204), as discussed herein. The second portion 604*b* can be configured to direct light into the eye 200 for illumination of the eye structure being viewed, as discussed herein. In some embodiments, light can also be directed into the eye for illumination through the first portion 604*a*.

The gonioscope 600 can include two or more separate, spaced apart contact surfaces 606*a* and 606*b* that are configured to contact the user's eye to transmit light to and/or from the eye 200. The first portion 604*a* of the gonioscopic optical element 604 can include a first distal contact surface 606*a*. The second portion 604*b* of the gonioscopic optical element 604 can include a second distal contact surface 606*b*. The first distal surface 606*a* and/or the second distal surface 606*b* can be concave, and can have a spherical curved shape, and can be configured to fit onto a structure of the eye 200, such as the cornea 202. The radius of curvature of the first distal surface 606*a* and/or the second distal surface 606*b* can be greater than 5 mm, greater than 7.5 mm, greater than 8 mm, greater than 9 mm, greater than 10 mm, greater than 11 mm, greater than 12 mm, or any values therebetween, or any ranges bounded by any combination of these values, although values outside these ranges could be used in some instances. The first distal surface 606*a* and/or the second distal surface 606*b* can have a radius of curvature of 15 mm or less. The first distal surface 606*a* and the second distal surface 606*b* can have the same radius of curvature. The first distal surface 606*a* and the second distal surface 606*b* can lie on the same sphere.

In some embodiments, the gonioscope 600 can be configured to impede light from the light source (e.g., the surgical microscope) from reaching the retina of the eye 200, such as via the surface 605. This can enable the medical professional to increase the amount of light being used for illumination, without that light causing discomfort to the subject or damage to the eye 200. For example, the space between the first distal contact surface 606*a* and the second distal contact surface 606*b* can be positioned on a center (e.g., apex) of the cornea 202, can be positioned between the light source (e.g., the surgical microscope) and the optical axis of the eye or the visual axis of the eye. The gap between the first portion 604*a* and the second portion 604*b* of the gonioscopic optical element 604 can be configured to be positioned over a center (e.g., apex) of the cornea 202. The gap between the first portion 604*a* and the second portion 604*b* of the gonioscopic optical element 604 can be configured to intersect the optical axis of the eye 200 and/or the visual axis of the eye 200. The gap between the first portion 604*a* and the second portion 604*b* of the gonioscopic optical element 604 can be configured to be positioned between the retina of the eye 200 and the light source (e.g., a surgical microscope, which can direct light directly downward, in some implementations). A surface 605 of the gonioscopic optical element 600 can be configured to block light from the light source (e.g., the surgical microscope) from entering the eye 200 along the optical axis and/or along the visual axis. The surface 605 can have an opaque material (e.g., a reflective material) for blocking (e.g., redirecting by reflection) the light that would otherwise be directed from the light source to the retina of the eye 200. The surface 605 can be oriented to reflect light from the light source (e.g., directed along a downward direction such as from a surgical microscope), such as by total internal reflection. In some embodiments, light can be redirected (e.g., reflected) to enter the eye at a different angle, that is not directed towards the retina, such as to illuminate the anterior chamber of the eye 200. In some cases, some light can reach the retina, such as after being reflected or scattered by structures in the eye. The gonioscope 600 can be configured to impede light that enters the proximal surface 608, such as from the light source (e.g., surgical microscope), from reaching the retina of the eye without being reflected or scattered. The gonioscope 600 can be configured to block 95%, 90%, 85%, 80%, 75%, 70%, 65%, or 60% of the light from the light source (e.g., surgical microscope) that would reach the retina if the gonioscope 600 were removed from reaching the retina, or any values between these percentages, or any ranges bounded by any combination of these percentages, although values outside these percentages can be used in some instances. In some instances, the gonioscope 600 can be configured to direct a portion of the light from the light source into the eye to produce a visible optical fixation point, as discussed herein.

The gonioscopic optical element 604 can include a proximal surface 608, which can be shared by both the first portion 604*a* and the second portion 604*b* of the gonioscopic optical element 604. The proximal surface 608 can be curved (e.g., having a spherical curved shape), as can be seen in FIGS. 30 and 31. The proximal surface 608 can be convex. The proximal surface 608 can be curved to prevent the reflected light from the light source (e.g., microscope) from interfering with the view of the image of the eye 200 produced by the gonioscope 600. The gonioscope can provide an image of the structure inside the eye with magnification of 1.3×, of 1.2×, of 1.1×, of 1.05×, of 0.9×, of 0.8×, of 0.7×, or no magnification (0.0×), or any value therebetween, or any range bounded by any combination of these values, although magnifications outside these ranges can be used in some implementations. In some embodiments, the proximal surface 608 can be planar, concave, toroidal, or can have any other suitable shape. The gonioscope 600 can be configured so that the proximal surface 608 faces upward when the gonioscope 600 is positioned on the eye for viewing the structure inside the eye, such as varying from a vertical direction by 0 degrees, 2 degrees, 5 degrees, 10 degrees, 15 degrees, 20 degrees, or any values therebetween, or any ranges bounded by any combination of these values. The light source (e.g., microscope) can direct light downward into the proximal surface 608 of the gonioscope 600. The gonioscope 600 can direct light forming an image of the structure in the eye 200 in an upward direction (e.g., to the microscope positioned above the gonioscope 600). In some cases, the gonioscope 600 can be used without tilting the subjects head to the side and/or with the eye 200 aligned straight forward, which can facilitate patient comfort during use of the gonioscope 600.

With reference to FIG. 31, light from inside the eye 200 (e.g., the anterior chamber angle 204) that would normally be hidden from view by total internal reflection can be permitted to exit the eye through the first portion 604*a* of the gonioscopic optical element 604. In some instances, an optical material such as index matching gel, can fill the space between the gonioscope 600 and the surface of the eye 200 (e.g., the cornea 202). Light from the area being imaged inside the eye 200 (e.g., the anterior chamber angle 204) can exit the eye 200 and enter the gonioscopic optical element 604 through the first distal surface 606*a*. The light can propagate to a first reflection surface 607, where the light can be reflected towards a second reflection surface 605, where the light can be reflected upward, and the light than then exit the gonioscope 600 through the proximal surface 608. Although not shown in FIG. 31 for sake of simplicity, the light can be refracted as it exits the proximal surface 608, and/or as it transitions from the eye to the gonioscope 600 at the distal surface 606*a*. The light forming the image can be reflected twice, so that the gonioscope 600 provides an upright image that is not inverted. The first reflection surface 607 can be positioned radially outward from the second reflection surface 607. The first reflection surface 607 can be on a side of the first portion 604*a* of the gonioscopic optical element 604 that is opposite the second reflection surface 605. One or both of the first reflection surface 607 and/or the second reflection surface 605 can include a reflective material to facilitate reflection of light. For example, a metal coating can be applied to the outside of the gonioscope 600 at the first reflection surface 607 and/or the second reflection surface 605. In some embodiments, the reflective material can be opaque, and can block light from outside the gonioscope 600 from propagating down through the central region of the gonioscope 600 and into the eye 200, as discussed herein. In some embodiments, the first reflection surface 607 and/or the second reflection surface 605 can be oriented so that light is reflected by total internal reflection.

Figure 32:
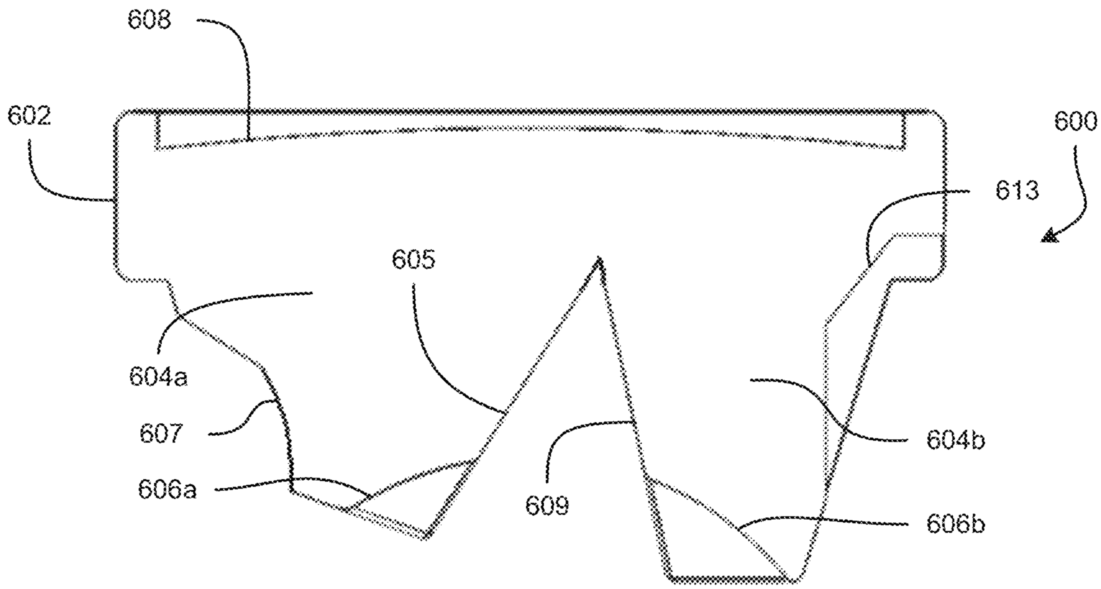
FIG. 32 is a cross-sectional view of an example embodiment of a gonioscope.
Figure 33:
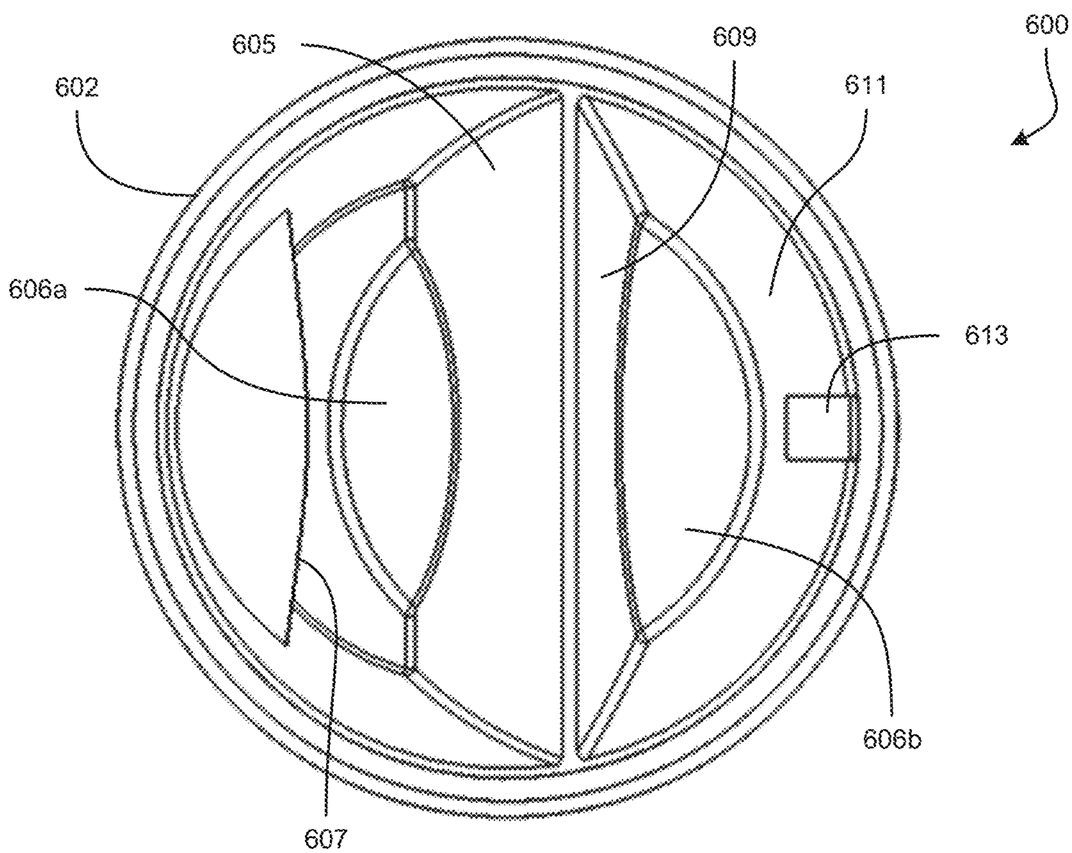
FIG. 33 is a top-down view of an example embodiment of a gonioscope, where the proximal surface is shown transparent to illustrate the surfaces inside the gonioscope.

The first reflection surface 607 and/or the second reflection surface 605 can be planar. In some embodiments, one or both of the first reflection surface 607 and the second reflection surface 605 can be curved, which can adjust the field of view and/or magnification of the image produced by the gonioscope 600. One or both of the reflection surface 607 and the second reflection surface 605 can be concave or convex in one or both of the horizontal and vertical directions, to adjust the image produced by the gonioscope 600. By way of example, with reference to FIGS. 32 and 33, the first reflecting surface 607 can be convex on the inside surface that reflects light, which can increase the field of view of the image produced by the gonioscope 600. The second reflecting surface 605 can be planar. In some embodiments, the second reflection surface 605 can have a larger area than the first reflection surface 607, and the first reflection surface 607 can be configured to diverge the reflected light so light reflected by smaller area of the first reflection surface 607 can reflect from a larger area on the second reflection surface 605, which can increase the size of the image produced by the gonioscope. Many alternatives are possible. The first reflecting surface 607 can be convex on the inside surface that reflects light in the horizontal direction (see FIG. 33) and linear in the vertical direction, to diverge the light in the horizontal direction. The second reflecting surface 605 can be convex on the inside surface that reflects light in the vertical direction and linear in the horizontal direction, to diverge the light in the vertical direction. The second reflecting surface 605 can be convex on the inside surface that reflects light, while the first reflecting surface 607 can be planar. The first reflecting surface 607 can be convex on the inside surface that reflects light in the vertical direction (see FIG. 32) and linear in the horizontal direction. The second reflecting surface 605 can be convex on the inside surface that reflects light in the horizontal direction and linear in the vertical direction. Each of the examples provided above can be modified to have concave curvature on the inside surface that reflects the light, so as to increase magnification of the image.

The gonioscopic optical element 604 can direct light from the light source (e.g., the microscope) into the eye 200 to illuminate the structure being imaged (e.g., the anterior chamber angle 204), such as through the second portion 604*b*. As can be seen in FIG. 31, light from the light source (e.g., the microscope) can propagate downward and enter the gonioscope 600 through the proximal surface 608, can propagate through the second portion 604*b* of the gonioscopic optical element 604 to the second distal surface 606*b*, where the light can transition from the gonioscope 600 to the eye 200. The second distal surface 606*b* can be configured to be positioned over the area of the eye 200 being imaged, such as over the anterior chamber angle 204.

In some embodiments, some of the light can reflect off of one or both of the side surfaces 609 and 611 of the second portion 604*b* of the gonioscopic optical element 604. One or more of the side surfaces 609 and 611 can be angled to receive the light that enters the proximal surface 608 and to reflect the light so that it is redirected towards the structure in the eye 200 being imaged (e.g., the anterior chamber angle 204). FIG. 31 shows light reflecting off of surface 609 to be directed towards the anterior chamber angle 204. One or more of the surface 609 and 611 can be angled so that they draw closer together in the downward direction. The area of the proximal surface 608 that collects light into the second portion 604*b* of the gonioscopic optical element 604 can be larger than the second distal surface 606*b* that outputs the light into the eye 200. The light entering the second portion 604*b* of the gonioscopic optical element 604 can be concentrated as it propagates downward towards the distal surface 606*b*, such as by reflecting off of one or more of the sides 609 and 611 of the second portion 604*b* of the gonioscopic optical element 604. In some embodiments, the surface 609 can be planar, and the surface 611 can be curved, such as having a semicircular cross-sectional shape, as can be seen in FIG. 29. In some embodiments, the second portion 604*b* of the gonioscopic optical element 604 can have 3 sides, 4 sides, 5 sides, 6 sides, or more, each of which can be planar or curved. In some embodiments, the second portion 604*b* of the gonioscopic optical element 604 can have a continuously curved side wall, such as in the shape of a truncated cone. One or more of the side walls 609 and 611 can have a reflective material to facilitate reflection of the light. For example, a metal coating can be applied to the outside of the gonioscope 600 at the side walls of the second portion 604*b* of the gonioscopic optical element 604. In some embodiments, one or more of the side walls 609 and 611 can be oriented to reflect light by total internal reflection.

Some of the light can be directed through the gonioscope 600 and into the eye without any reflections, as can be seen in FIG. 31. Some of the light can be directed through the gonioscope 600 and into the eye with a single reflection, as can be seen in FIG. 31. This can avoid light losses that can occur when the light is reflected multiple times before being provided to the eye 200 for illumination, as is the case with some gonioscopes, especially double-reflection gonioscopes that provide both light input for illumination and light output for producing an image by reflecting the light twice. The gonioscope 600 can be configured to provide 50%, 60%, 70%, 80%, 90% of the light that impinges on the portion of the proximal surface 608 that corresponds to the second portion 604*b* of the gonioscopic optical element 604 to the eye, or any values between these percentages, or any ranges bounded by any combination of these percentages, although values outside these percentages can be used in some instances. Although not shown in FIG. 31 for sake of simplicity, the light can be refracted as it exits the proximal surface 608, and/or as it transitions from the eye 200 to the gonioscope 600 at the distal surface 606*b*. Although not shown in FIG. 31, light from the first portion 604*a* of the gonioscopic optical element 604 can be used to illuminate the eye 200. For example, light (e.g., propagating downward from the light source, such as a microscope) can enter the proximal surface 608 over the first portion 604*a* of the gonioscopic optical element 604, can reflect off of the second reflection surface 605, can reflect off of the first reflection surface 607, and can exit the gonioscope 600 through the first distal contact surface 606*a* to enter the eye 200. This light can follow a path that is opposite to the path of light that produces the image, which is illustrated in FIG. 31.

In some embodiments, the gonioscope 600 can be configured to provide an optical fixation point, which can facilitate alignment and/or steadying of the eye 200, as discussed herein. The gonioscope 600 can include a light redirecting feature to redirect light to produce the optical fixation point. For example, the gonioscope 600 can have an optical fixation point reflection surface 613, which in some embodiments can be formed as a recess in the surface 611 of the second portion 604*b* of the gonioscopic optical element 604. As can be seen in FIG. 31, the optical fixation point reflection surface 613 can be configured to reflect light across the second portion 604*b* of the gonioscopic optical element 604, through the surface 609, across the gap between the first portion 604*a* and the second portion 604*b* of the gonioscopic optical element 604, to the outside of surface of the second reflection surface 605, where the light can be reflected downward into the eye 200 (e.g., along the optical axis or visual axis of the eye 200), so that the light reaches the retina to provide a visible bright spot to the subject. The second reflection surface 605 can have two reflective surfaces. A reflective material on the second reflection surface 605 can have two reflective surfaces, with a first reflective surface facing inward to reflect light propagating inside the first portion 604*a* of the gonioscopic optical element 604, and a second reflective surface facing outward to reflect light to produce the optical fixation point. In some embodiments, the surface 609 can have a reflective material (e.g., a metal coating), which can have an aperture 615 to enable light for the optical fixation point to pass through the surface 609. In some embodiments, the light redirecting feature can include scattering features, such as surface diffusing feature or embedded diffusing features, which can scatter some of the light propagating through the second portion 604*b* of the gonioscopic optical element 604, and some of the scattered light can exit the surface 609 through the aperture 615 to form the optical fixation point.

In some embodiments, the gonioscope 600 can have one or more retention elements and/or one or more arms similar to those discussed in connection with the gonioscope 400. The gonioscope 600 can include a handle that is similar to the handles disclosed in connection with the gonioscopes 100 and 400. The gonioscope 600 can include wings similar to those disclosed in connection with the gonioscope 400, or can otherwise be configured to couple to a lid speculum.

Figure 34:
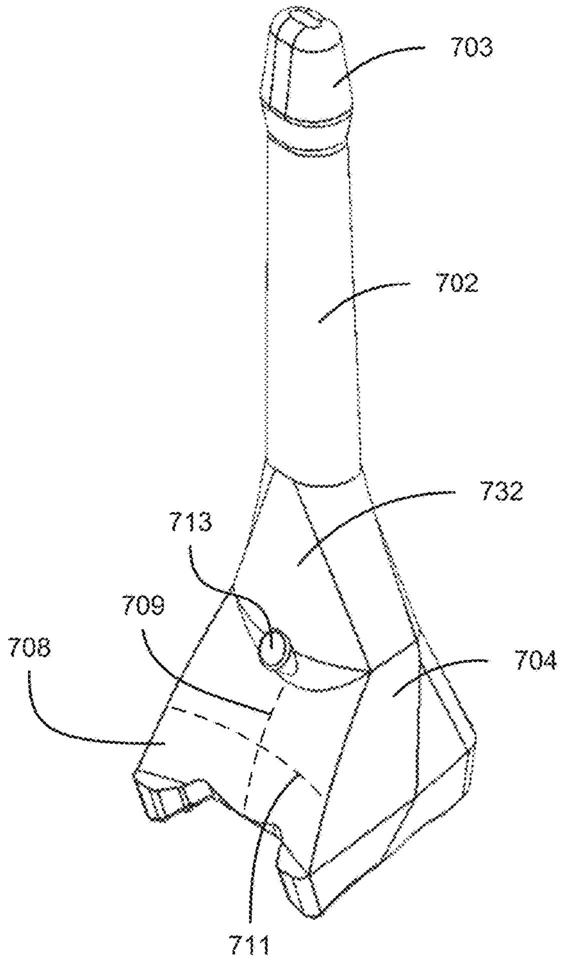
FIG. 34 is a top-front perspective view of an example embodiment of a gonioscope.
Figure 35:
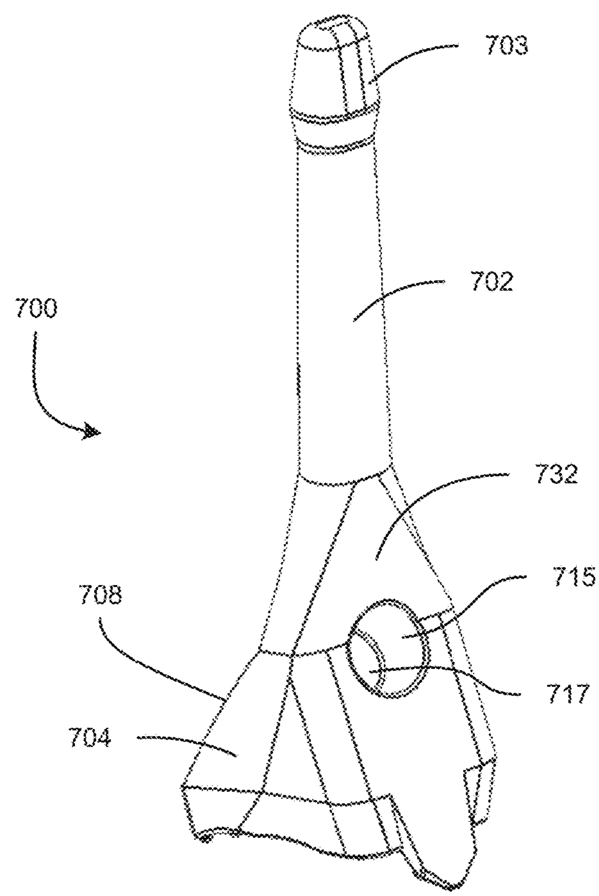
FIG. 35 is a top-rear perspective view of an example embodiment of a gonioscope.
Figure 36:
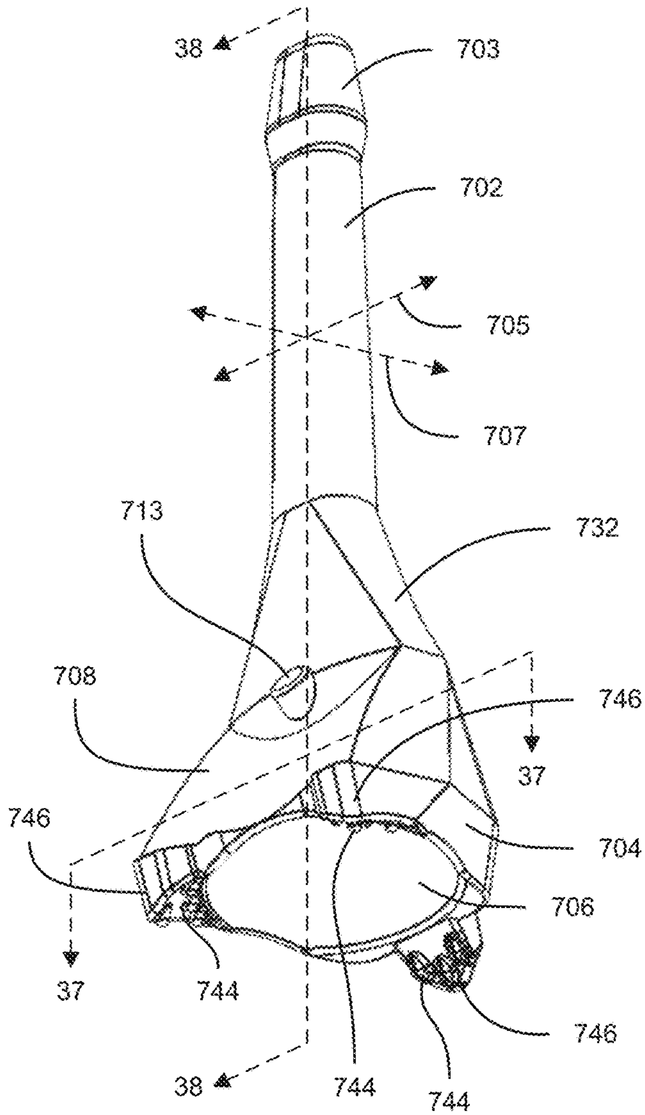
FIG. 36 is a bottom-front perspective view of an example embodiment of a gonioscope.
Figure 37:
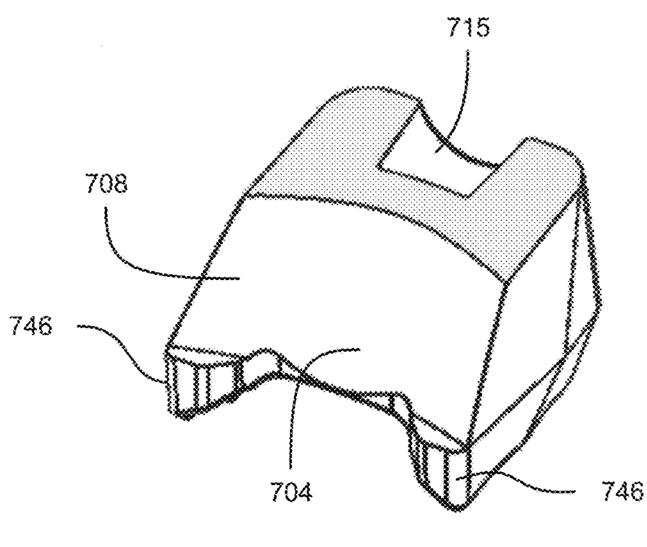
FIG. 37 is a cross-sectional perspective view of the example embodiment of a gonioscope taken at line 37-37 shown in FIG. 36.
Figure 38:
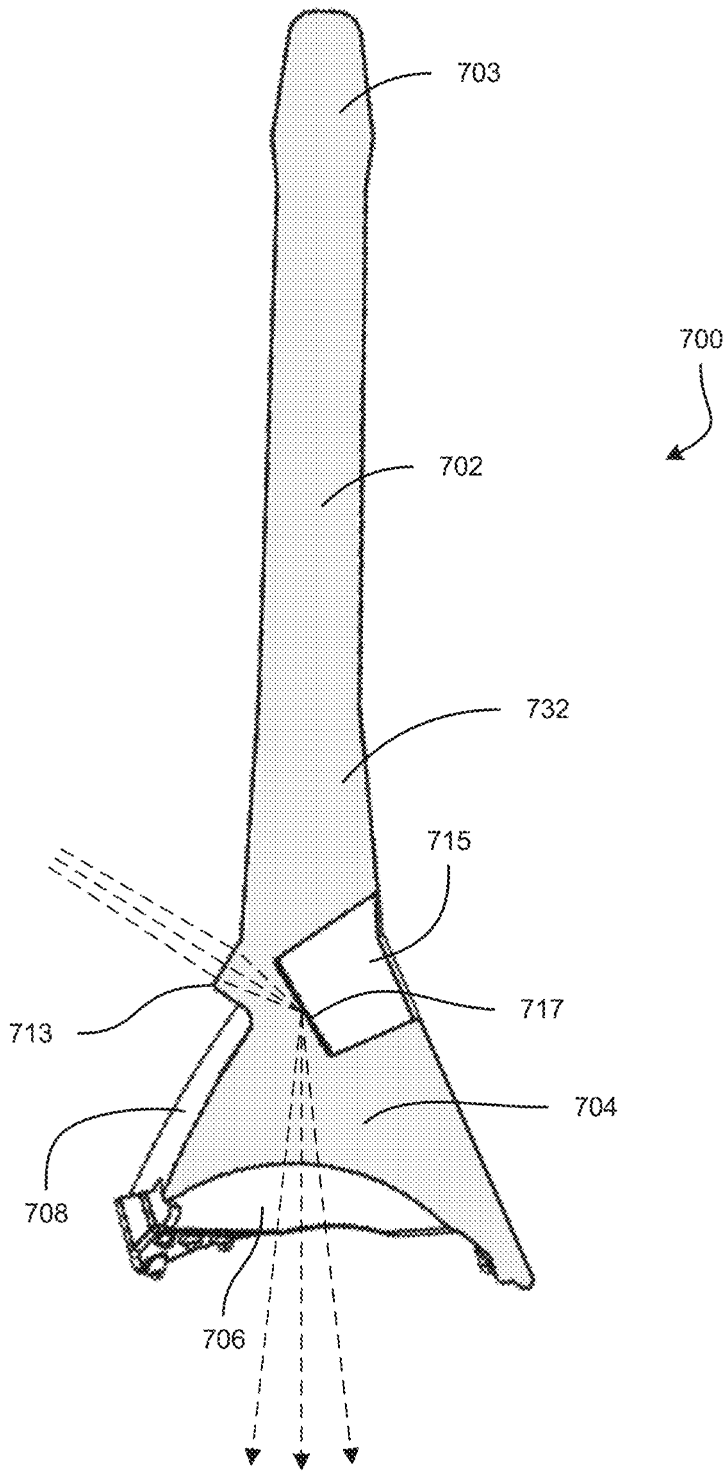
FIG. 38 is a cross-section view of the example embodiment of a gonioscope taken at line 38-38 shown in FIG. 36.

FIG. 34 is a top-front perspective view of an example embodiment of a gonioscope 700. FIG. 35 is a top-rear perspective view of the example embodiment of a gonioscope 700. FIG. 36 is a bottom-front perspective view of the example embodiment of a gonioscope 700. FIG. 37 is a cross-sectional perspective view of the example embodiment of a gonioscope 700 taken at line 37-37 shown in FIG. 36. FIG. 38 is a cross-section view of the example embodiment of a gonioscope 700 taken at line 38-38 shown in FIG. 36. The gonioscope 700 can have features discussed in connection with the other gonioscopes 100, 400, 600 disclosed herein. Many features discussed in connection with the gonioscopes 100, 400, 600 can apply also to the gonioscope 700 and are not discussed in detail in connection with the gonioscope 700 for sake of brevity.

The gonioscope 700 can include a handle 702 and a gonioscopic optical element 704. In some embodiments, the handle 702 and the gonioscopic optical element 704 can be integrally formed of the same material, such as by injection molding of a single piece. The gonioscopic optical element 704 and/or the handle 702 can be made of a transparent material, as discussed herein. The handle 702 can be an ambidextrous handle, similar to the handle 402 of the example gonioscope 400 disclosed herein. The gonioscope 700 can be symmetrical across the plane of the cross-sectional view of FIG. 38, which extends through the middle of the handle 702 and the rest of the gonioscope 700. The gonioscope 700 can be configured such that the handle 702 extends generally vertically upward when positioned on the eye oriented for viewing the anterior chamber angle, and/or such that the center of gravity of the gonioscope 700 can be positioned generally above the eye, similar to the gonioscope 400.

The handle 702 can have a cross-sectional shape that can be generally circular, round, oval, elliptical, or polygonal. This shape can enable a medical practitioner to rotate the gonioscope 700 by twisting the handle 702 between the practitioner's fingers. This can be useful, for example, in a medical procedure where the practitioner desires to view multiple areas in the eye, or to view a large area in the eye. For example, by twisting the handle in the fingers the proximal surface 708 can be rotated thereby allowing the practitioner to view further left or right in the eye as the refractive angle is increased. By comparison, the handle 402 of the gonioscope 400 can be more difficult to rotate between the fingers. The gonioscope 400 can be rotated by moving the wrist. The gonioscope 400 can be useful, for example, in medical procedures where the practitioner desires to focus on a single or small area. The wide handle 402 of gonioscope 400 can impede unintentional rotation of the gonioscope 400. The gonioscope 700 can have a handle 702 as shown in the figures or can have a handle 402 similar to the gonioscope 400. The handle 702/402 can have a ratio between the width (e.g., along a direction 705 extending between the right and left sides of the gonioscope 700) and the depth (e.g., along a direction 707 extending between the front and back sides of the gonioscope 700) of 8 to 1, 6 to 1, 5 to 1, 4 to 1, 3.5 to 1, 3 to 1, 2.5 to 1, 2 to 1, 1.75 to 1, 1.5 to 1, 1.25 to 1, 1.1 to 1, 1 to 1, 1 to 1.1, 1 to 1.25, 1 to 1.5, or any values therebetween, or any ranges bounded by any combination of these values, although other values can be used in some cases.

The handle 702 can have one or more touch features 703, which can be felt by the practitioners fingers while holding the handle 702 to provide an indication of the location on the handle 702 that is being held. The one or more touch features 703 can be wider or narrower than the main shaft of the handle 702. In FIGS. 34 to 36, the handle 702 has a single touch feature 703 (e.g., a widened region) at a top of the handle 702 to indicate to the practitioner when the gripping location is near the top of the handle 702, which can impede accidental dropping or mistaken positioning of the gonioscope 700. The one or more touch features 703 can be one or more ridges, indentations, tear-drop shaped features, rough areas, etc. The handle 702 can connect to the gonioscopic optical element 704 at a junction area 732, which can be tapered from the top of the gonioscopic optical element 704 towards the handle 702. The junction area 732 can serve as a touch feature to indicate that the gripping location is near the base of the handle 702 when the user feels the widening of the juncture area 732.

The gonioscopic optical element 704 can include a distal surface 706 and a proximal surface 708, similar to the other gonioscopes 100, 400, 600 disclosed herein. Many features discussed in connection with the gonioscopic optical elements 104, 404, 604 can apply to the gonioscopic optical element 704 of the gonioscope 700 even though not expressly discussed. The proximal surface 708 can have an aspherical shape. The proximal surface 708 can have a biconic shape, can conform to a portion of a hyperboloid, can conform to an inside portion of a toroid, or any other suitable geometric shape. The proximal surface 708 can be convex along a first direction or axis 709 and/or can be concave along a second direction or axis 711, which can be orthogonal to the first axis 709. The first axis 709 can correspond to a height of the produced image, and the second axis can correspond to a width of the produced image. The convex curvature along the first axis 709 can be seen in FIG. 34, and in the cross-sectional view of FIG. 38. The concave curvature along the second axis 711 can be seen in FIG. 34, and in the cross-sectional view of FIG. 37. The convex curvature along the first axis 709 can produce a magnification along a first direction or axis of the image (e.g., the height of the image), and the magnification can be 1.1×, 1.2×, 1.3×, 1.4×, 1.5×, 1.6×, or any values therebetween, or any ranges bounded by any combination of these values, although amounts of magnification can be produced in some embodiments. The concave curvature along the second axis 711 can produce a demagnification along a second direction or axis of the image (e.g., the width of the image), and the demagnification can be 0.95×, 0.9×, 0.85×, 0.8×, 0.75×, 0.7×, 0.65×, 0.6×, or any values therebetween, or any ranges bounded by an combination of these values, although other amounts of demagnification can be produced in some embodiments.

The image can provide more detail of the imaged tissue in the first axis (e.g., the height of the trabecular meshwork, anterior angle, etc.), while also provide a wide field of view. In some cases, the demagnification can be used so that the size of the gonioscopic optical element 704 can be reduced, while still providing a sufficiently wide field of view (e.g., a horizontal field of view). For example, the width of the distal surface 706 of the gonioscopic optical element 704 can be reduced while still providing the same or similar field of view along the width of the image because of the demagnification. In some medical conditions, the peripheral portion of the cornea can become hazy. A smaller gonioscopic optical element 704 (e.g., which can still produce a sufficiently large field of view) can be advantageous because it can enable imaging of the eye through a more central area of the cornea, and can facilitate avoiding the peripheral portions of the cornea, which can be hazy in some instances. Also, a smaller gonioscopic optical element 704 can be less cumbersome to use, and/or can give the practitioner move flexibility in positioning the gonioscope 700.

The gonioscope 700 can have one or more retention elements 744, which can be configured to engage tissue of the eye, such as scleral tissue around the cornea, to retain the gonioscope 700 in positioned relative to the eye. The one or more retention elements 744 can be positioned on the distal side of one or more arms 746. The illustrated embodiment of FIG. 36 has three arms 746, although any suitable number of arms can be used, such as one arm, two arms, four arms (e.g., one at each corner), five arms, six arms, etc. The one or more retention elements 744 and the one or more arms 746 can include features that are the same as, or similar to features of the retention elements and arms described in the WO 2016/154066 publication, which is incorporated herein by reference.

The gonioscope 700 can be used to create an optical fixation feature for the subject to look at or focus on during use of the gonioscope 700, which can impede movement of the subject's eye relative to the gonioscope 700. The gonioscope 700 can include a light entry area or surface 713 on a front of the gonioscope 700. Light for producing the optical fixation feature can enter the gonioscope 700 through the light entry surface 713. The light can then be redirected into the eye to produce the optical fixation feature (e.g., a bright spot, shape, pattern, etc.). The light entry surface 713 can be positioned above the proximal surface 708 of the gonioscopic optical element 704. The light entry surface 713 can be between the gonioscopic optical element 704 and the handle 702, and/or between the gonioscopic optical element 704 and the juncture area 732. The light entry surface 713 can be position in a middle of the gonioscope 700 (e.g., equidistant between the right and left sides). A plane down the middle of the gonioscope 700 dividing the gonioscope 700 into right and left sides (e.g., the plane of the cross-sectional view of FIG. 38) can extend through the light entry surface 713. The light entry surface 713 can be on a protrusion that extends from a front surface of the gonioscopic optical element 704, such as on or above the proximal surface 708. The light entry surface 713 can be oriented to face towards a light source, such as a light source on a surgical microscope, although other light sources can be used in some implementations. The light entry surface 713 can have a shape of a circle, oval, square, polygon, or any other suitable shape. In some cases, the light entry surface 713 can be a portion (e.g., upper portion) of the proximal surface 708 of the gonioscopic optical element 704. The light entry surface 713 can have a colored coating to transmit light of a particular color (e.g. red, green or blue), to produce a colored optical fixation feature.

The gonioscope 700 can have a recess 715 formed on a back side of the gonioscope 700 (e.g., formed in the back side of the gonioscopic optical element 704). A surface of the recess 715 can redirect the light. For example, the recess 715 can have a base surface 717, which can be used to redirect light (e.g., light that entered through the light entry surface 713) into the eye to produce the optical fixation feature. The base surface 717 can reflect light by total internal reflection (TIR). The recess 715 can contain air or some other material having a lower index of refraction than the material of the gonioscopic optical element 704. In some embodiments, the base surface 717 can have layer (e.g., a coating) of a material having a lower index of refraction than the material of the gonioscopic optical element 704. In some embodiments, the base surface 717 can have a reflective layer, such as a metallic material, to facilitate reflection of light. In some cases, the base surface 717 can have light scattering features and can redirect a portion of the light into the eye by scattering the light. At least a portion of the base surface 717 can be a diffuse surface. In some cases the base surface 717 can be a frosted surface to diffuse or scatter light.

The light entry surface 713 can be curved (e.g., concave or convex). The light entry surface 713 can be a lens. The light entry surface 713 can have optical power. The light entry surface 713 can cause the light entering the gonioscope 700 therethrough to converge, to diverge, to increase or decrease in convergence, or to increase or decrease in divergence. The light entry surface 713 can have a spherical curvature. In some embodiments, an aspherical curvature, a paraboloidal curvature, or any other suitable curvature shape can be used to modify the light entering the gonioscope 700.

Figure 39:
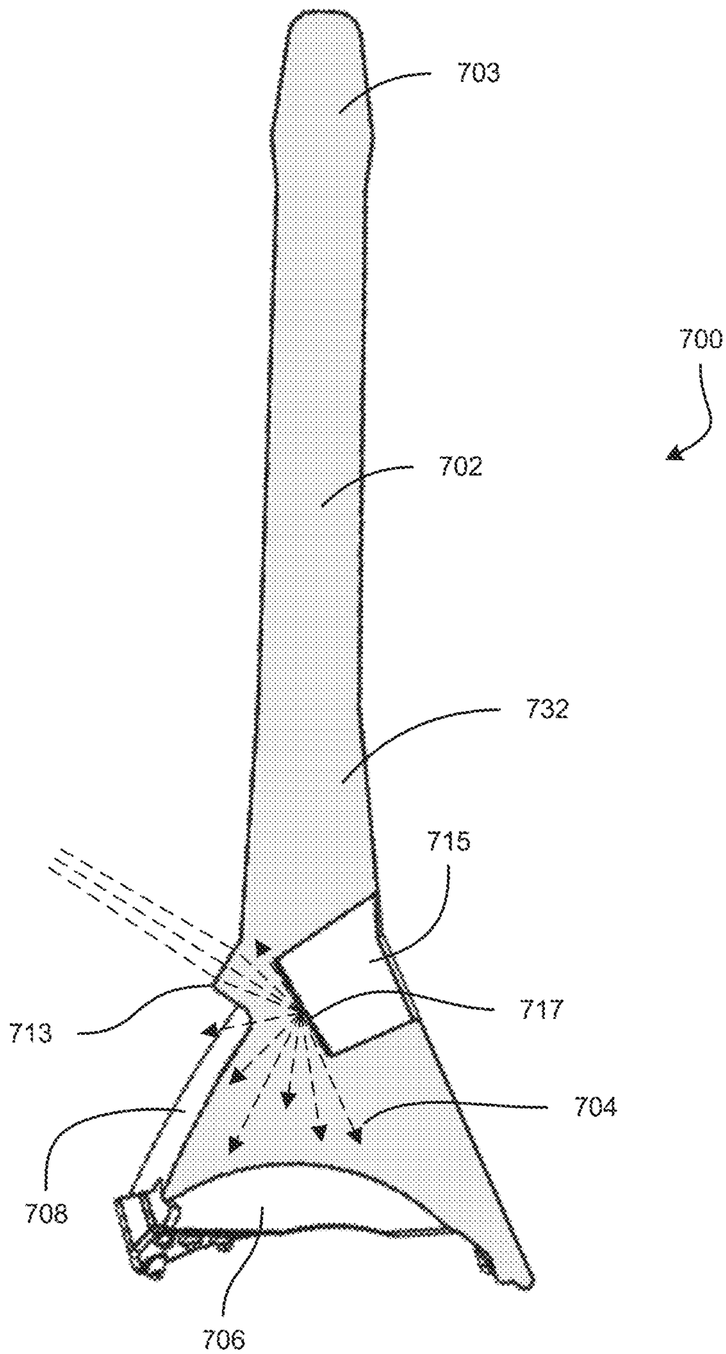
FIG. 39 is a cross-section view of an example embodiment of a gonioscope.

With reference to FIG. 38, the light entry area or surface 713 can focus the light onto a subset (e.g., a spot) of the base surface 717. The light (e.g., from a surgical microscope) can be diverging or collimated. The light entry surface 713 can have positive power to focus the light. The light can be reflected (e.g., by TIR) by the base surface 717 so that the light is directed into the eye to be visible to the subject (e.g., as a bright spot). In some embodiments, the optical fixation feature light directed into the eye by the gonioscope 700 can be diverging. In some cases the eye can focus the optical fixation feature light onto the retina. With reference to FIG. 39, in some embodiments, the base surface 717 can be configured to scatter the light that is focused at the spot or on the subset of the area of the base surface 717. Some of the scattered light enters the eye and is visible to the subject (e.g., as a spot that is less bright than the embodiment of FIG. 38).

Figure 40A:
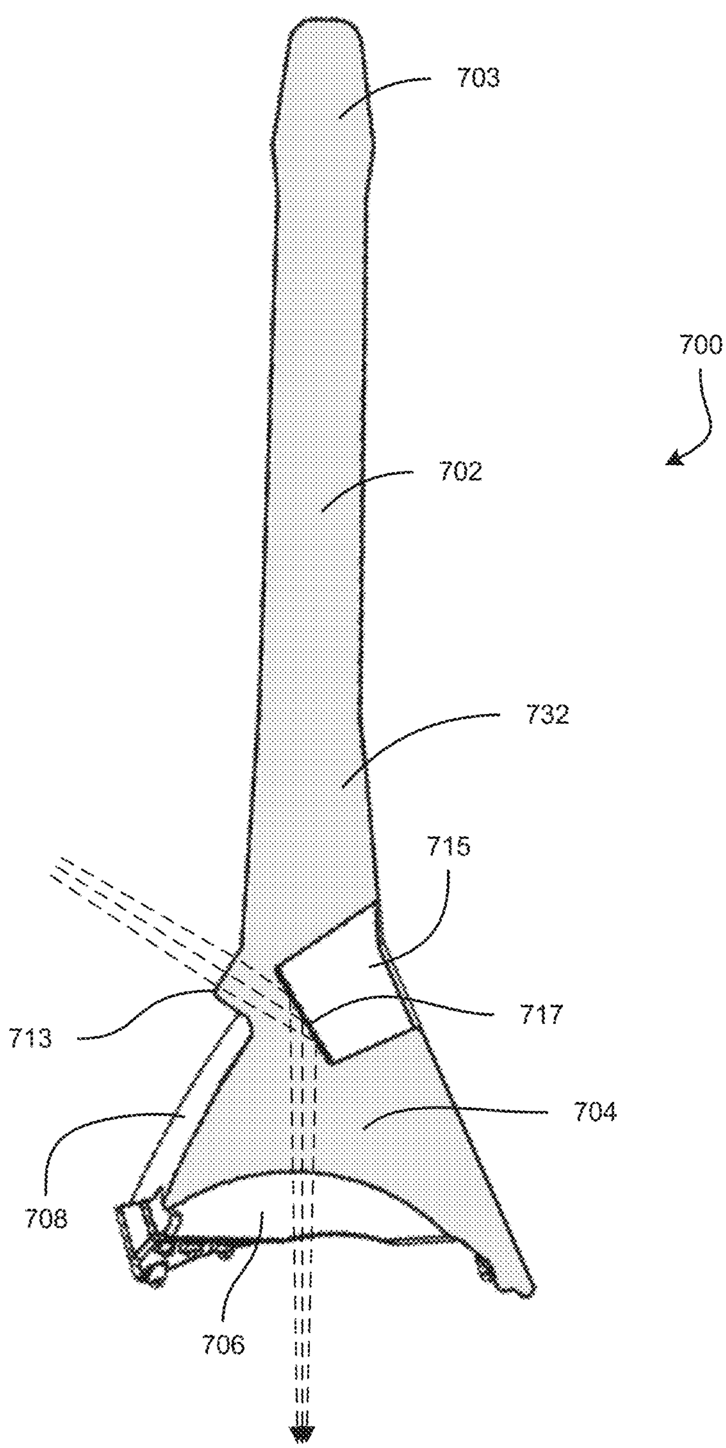
FIG. 40A is a cross-section view of an example embodiment of a gonioscope.
Figure 40B:
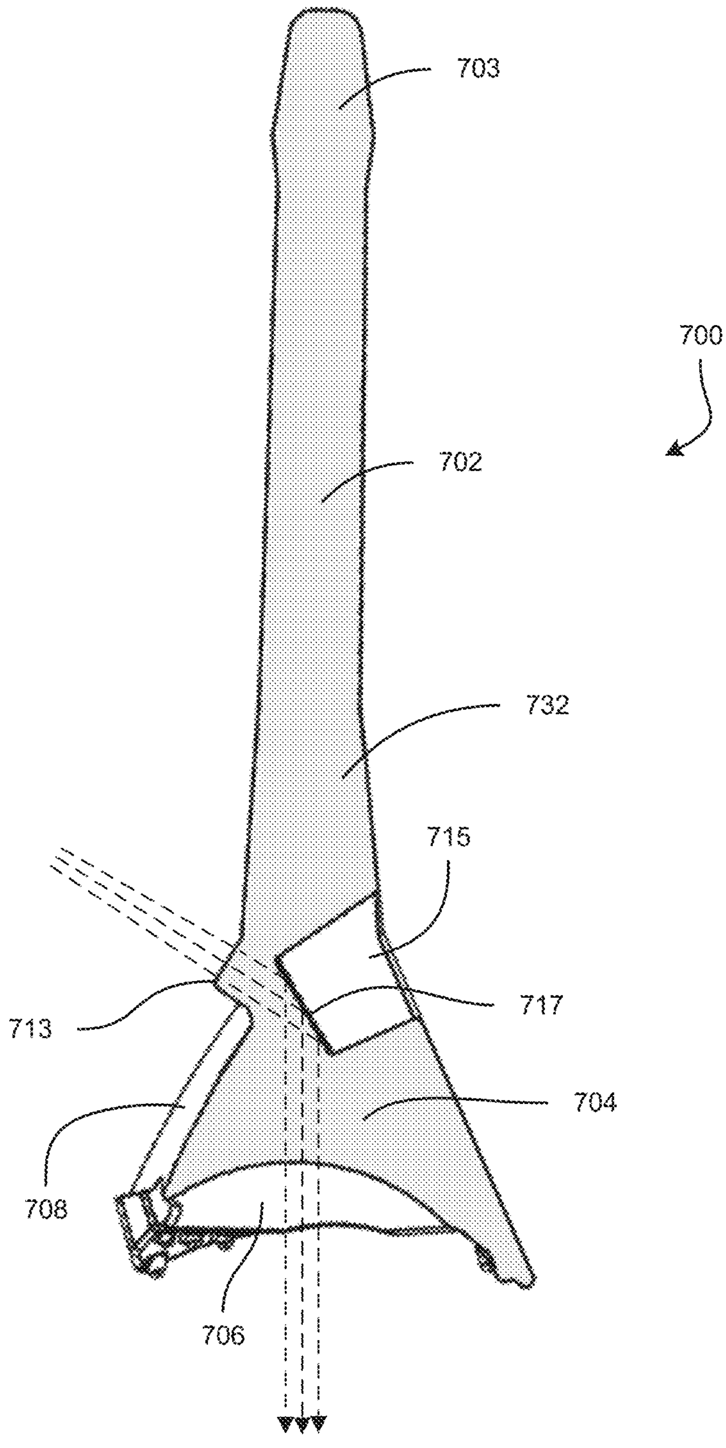
FIG. 40B is a cross-section view of an example embodiment of a gonioscope.
Figure 40C:
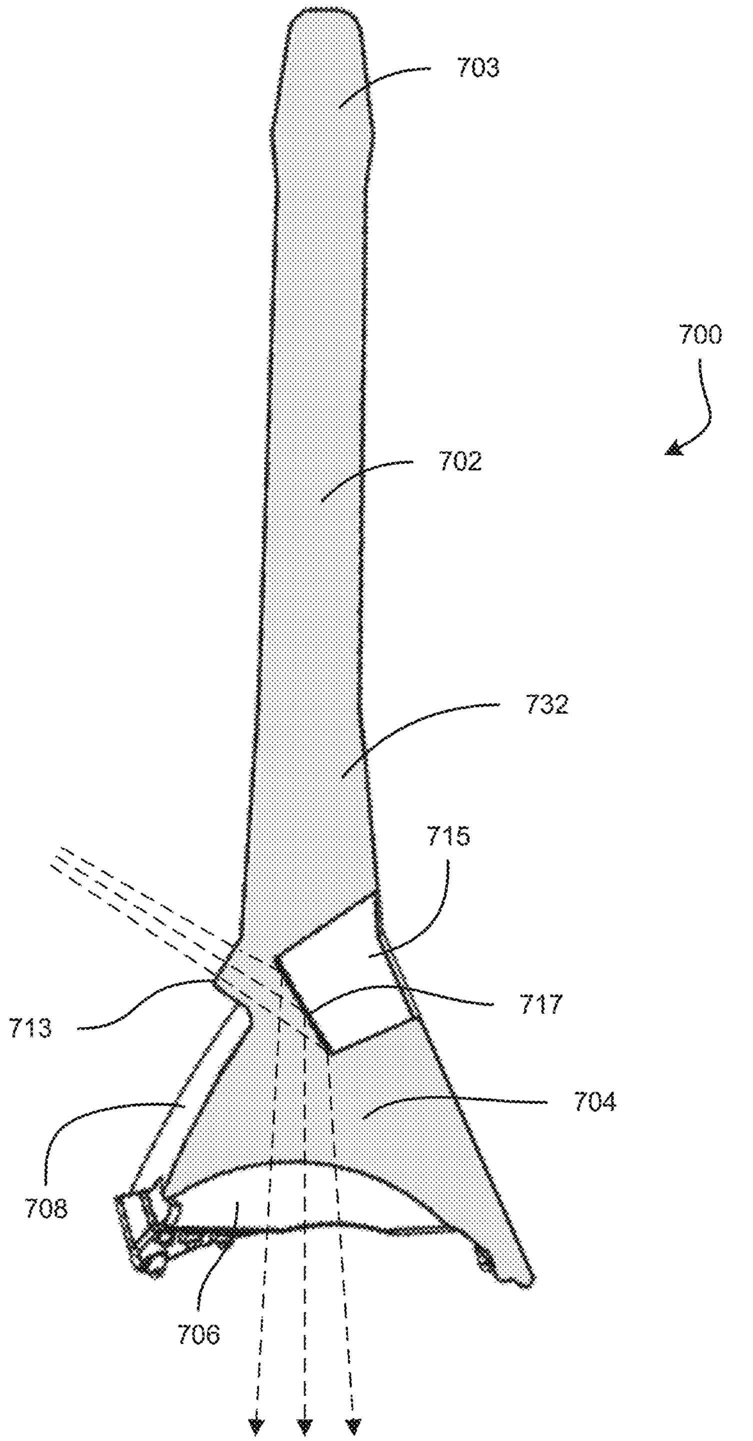
FIG. 40C is a cross-section view of an example embodiment of a gonioscope.

With reference to FIGS. 40A-C, the light entry area or surface 713 and the light reflecting surface 717 can output optical fixation feature light that is converging (as shown in FIG. 40A), collimated (as shown in FIG. 40B), or diverging (as shown in FIG. 40C). The light entry surface 713 can cause the light entering the gonioscope 700 to converge, as shown in FIG. 40A. The converging light can be reflected by the base surface 717, and the light can continue converging after being reflected. The light can be focused on the retina of the eye. In some cases, the natural lens of the eye can also focus the light onto the retina to make an optical fixation feature visible to the subject. With reference to FIG. 40B, in some embodiments the light entry surface 713 can collimate the light entering the gonioscope 700. The light (e.g., from a surgical microscope) can be diverging and the light entry surface 713 can have optical power to reduce the divergence of the light as it enters the gonioscope 700. The collimated light can be reflected (e.g., by TIR) by the base surface 717 and into the eye of the subject. The natural lens of the eye can focus the collimated light onto the retina. The light can be visible to the subject as it can be focused to a point of light on the retina (e.g., as a bright spot). In some cases the size and/or brightness of the spot or other optical fixation feature can depend on the size of the light entry surface 713 that collimates the light and/or the size of the surface 717 that reflects the light. With reference to FIG. 40C, the light entry surface 713 can cause the light entering the gonioscope 700 to diverge. The light (e.g., from a surgical microscope) can be diverging, and the light entry surface 713 can increase the divergence of the light, can permit the light to enter the gonioscope 700 without changing the divergence, or can decrease the divergence of the light. The diverging light can be reflected by the base surface 717 and can continue diverging as the light is directed to the eye. In some cases, the natural lens of the eye can focus the diverging light onto the retina to produce an optical fixation feature visible to the subject.

In some embodiments, the base surface 717 can modify the convergence or divergence of the light. For example, the surface 717 can have a curved (e.g., aspherical) surface. The base surface 717 can have various different configurations to modify the light in different ways. The base surface 717 can receive light that is converging, collimated, or diverging and can be configured to output light towards the eye that is converging, collimated, or diverging.

Figure 41:
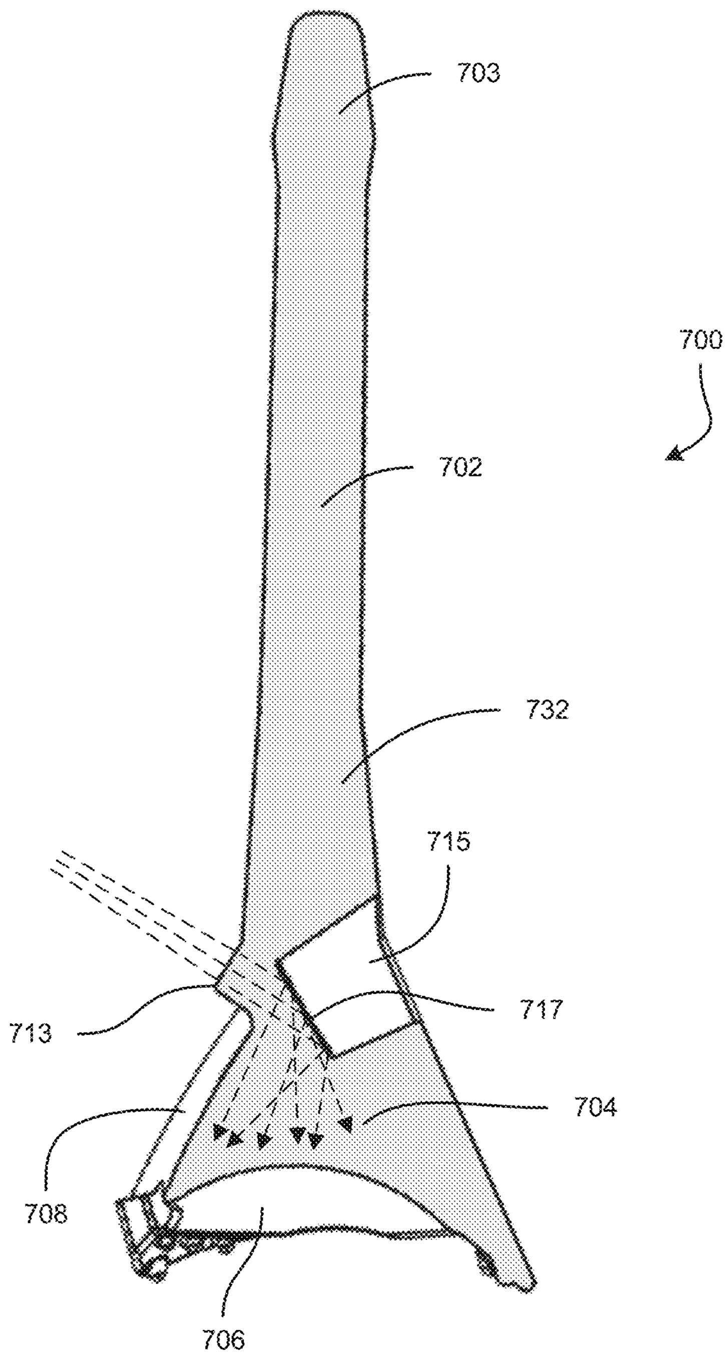
FIG. 41 is a cross-section view of an example embodiment of a gonioscope.
Figure 42:
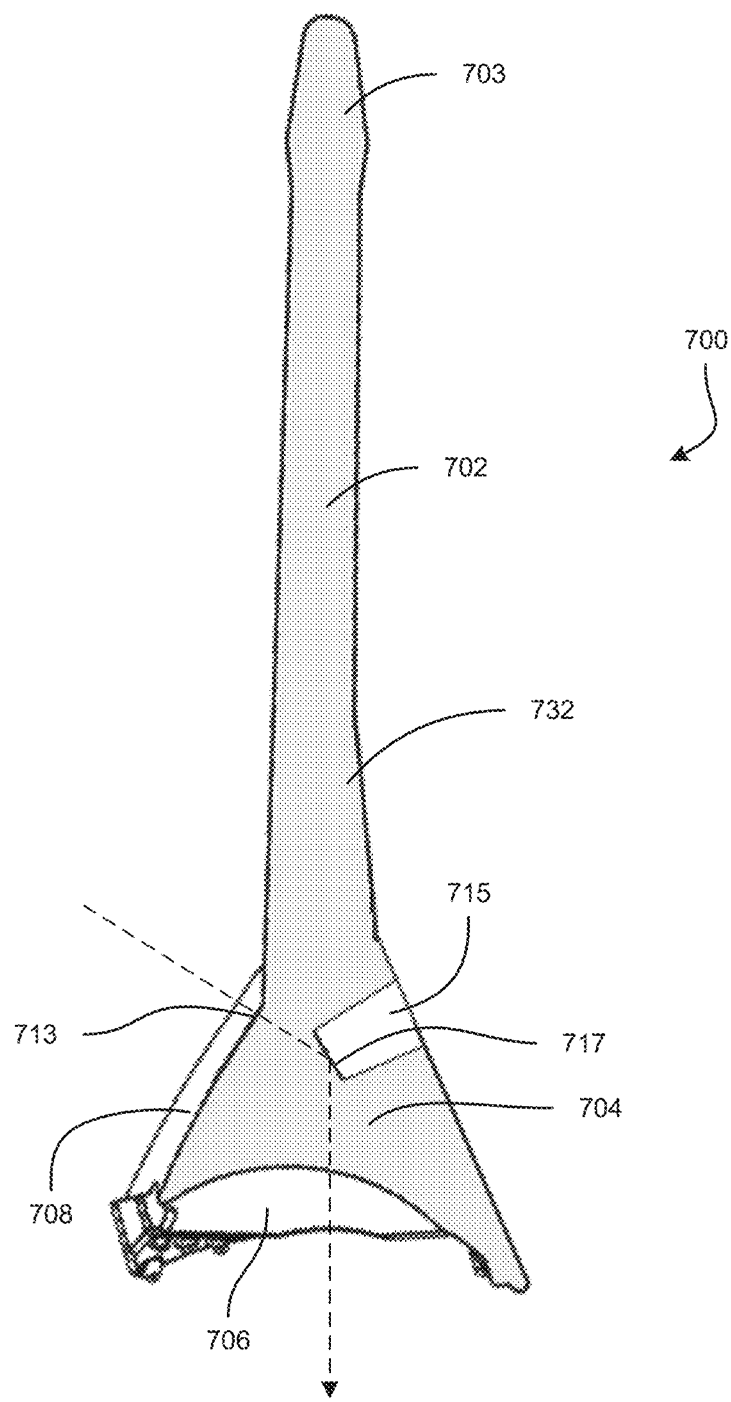
FIG. 42 is a cross-section view of an example embodiment of a gonioscope.

With reference to FIG. 41, in some embodiments, the base surface 717 can be configured to scatter the light. Some of the scattered light enters the eye and is visible to the subject (e.g., as a spot that is less bright than the embodiments of FIG. 40A-C). In some cases, the embodiments of FIGS. 38, 39, and 41 can be less susceptible to alignment errors than the embodiment of FIG. 40A-C. In the embodiment of FIG.

41, the light entry surface 713 can cause light entering the gonioscope to converge, collimate, or diverge, as discussed herein.

Many alternatives are possible. In some embodiments, the light entry area or surface 713 can scatter light entering the gonioscope. The light entry area can have surface diffusing features, a roughened surface, a frosted surface, etc. Some of the scattered light reaches the base surface 717 and is reflected into the eye (e.g., by TIR or by a reflective surface) to make a fixation feature visible to the subject. For example, a gonioscopic optical element similar to FIG. 4 can have a reflective portion on a back surface 110 (e.g., a mirror coating) to reflect a portion of the scattered light into the eye to produce an optical fixation feature visible to the subject. In some embodiments, diffused light can be reimaged by a curved surface 717 (e.g., an aspherical mirrored surface 717) to produce an optical fixation feature visible to the subject. In some embodiments, the light entry surface 713 can be configured to diverge (or increase divergence of) the light entering the gonioscope, such as to distribute the light across the area of the base surface 717. In some cases, the light entry surface 713 can permit light to enter the gonioscope 700 without changing the divergence or convergence of the light. The light entry surface 713 may have no optical power, in some embodiments.

Figure 43:
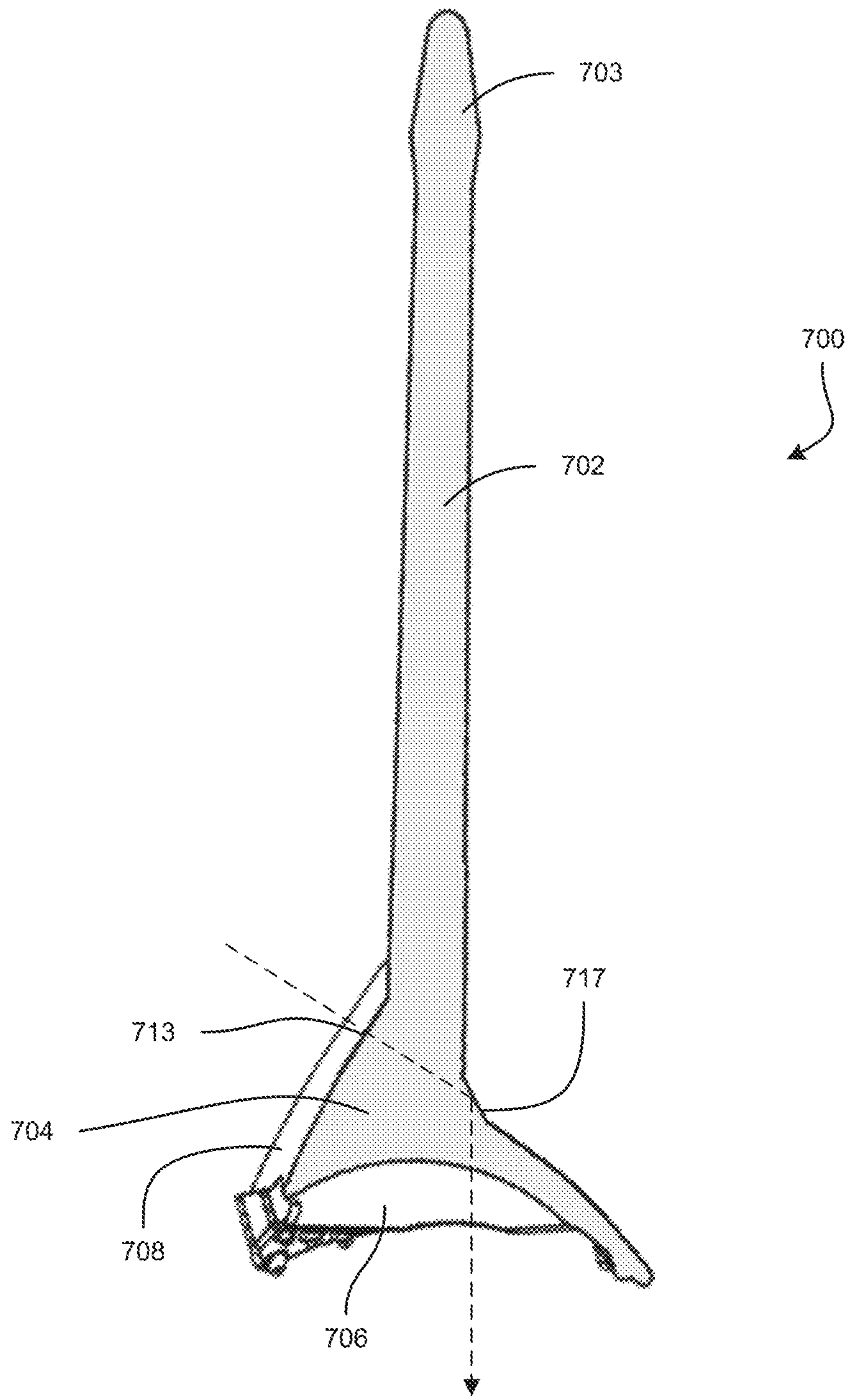
FIG. 43 is a cross-section view of an example embodiment of a gonioscope.

The gonioscope 700 can have a dedicated light entry surface 713 (e.g., on a raised protrusion). With reference to FIG. 41, in some embodiments, a portion of the proximal surface 708 of the gonioscopic optical element can be used for the light entry area or surface 713. In some implementations, the protrusion on the front of the gonioscope 700 can be omitted. In some embodiments, the recess 715 on the back of the gonioscope 700 can be omitted, for example, as can be seen in FIG. 43. A back surface of the gonioscope 700 (e.g., a back side of the gonioscopic optical element 704) can be used as the surface 717 for reflecting and/or scattering light into the eye to produce the optical fixation feature.

Figure 44:
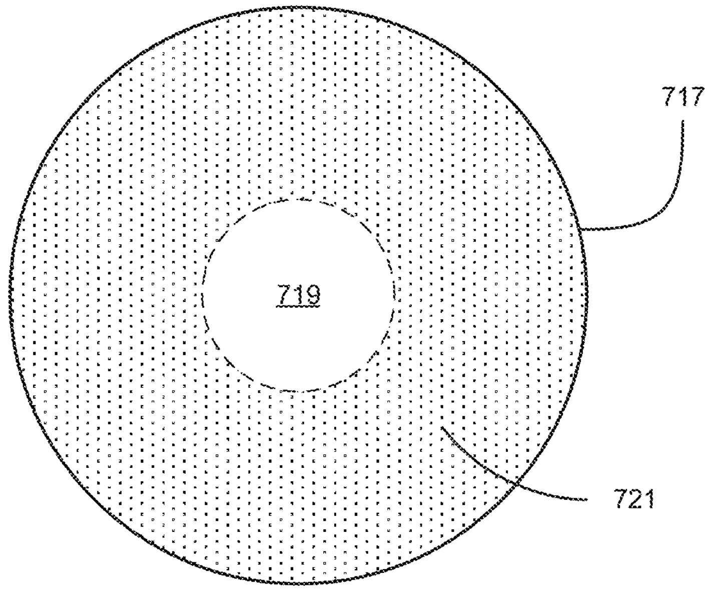
FIG. 44 shows an example embodiment of a surface for producing an optical fixation feature.
Figure 45:
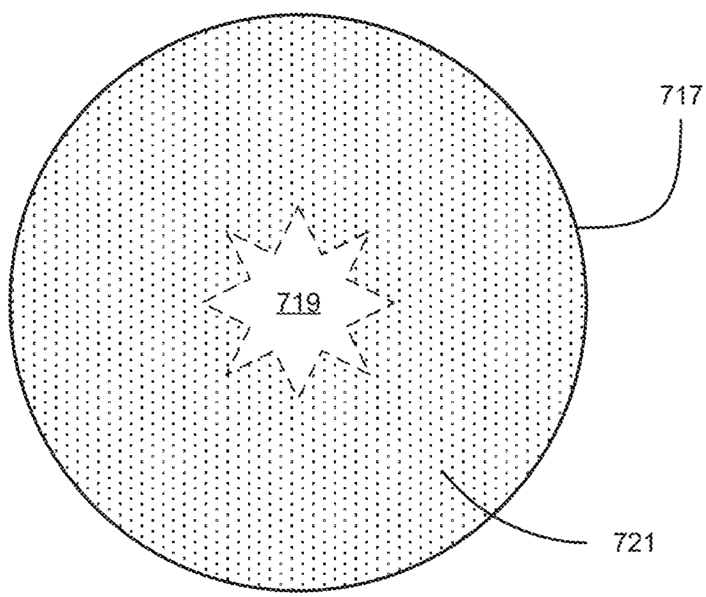
FIG. 45 shows an example embodiment of a surface for producing an optical fixation feature.
Figure 46:
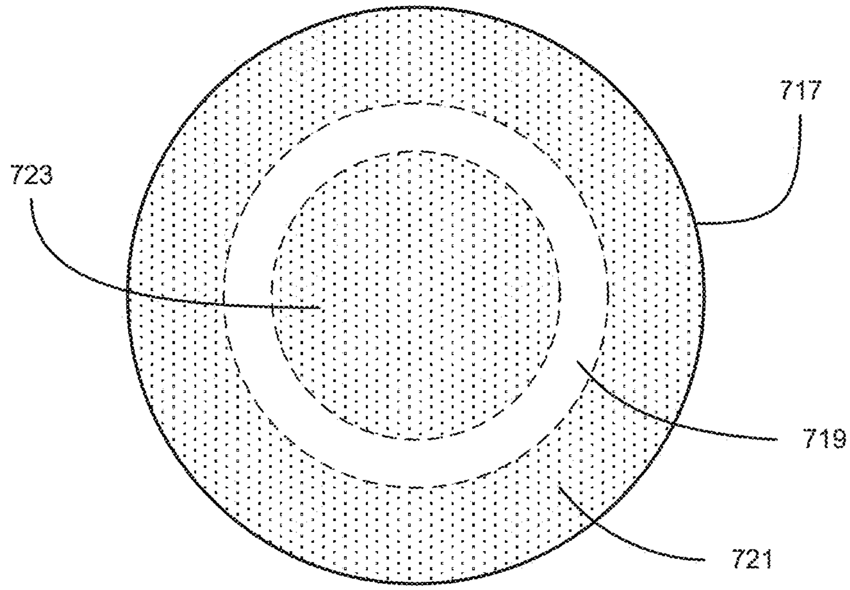
FIG. 46 shows an example embodiment of a surface for producing an optical fixation feature.
Figure 47:
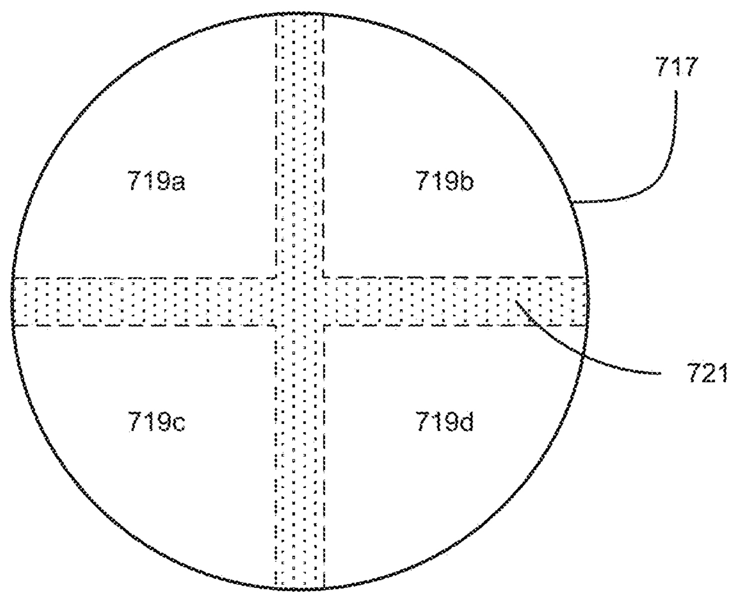
FIG. 47 shows an example embodiment of a surface for producing an optical fixation feature.

The configuration of the surface 717 can be used to produce different types of optical fixation features. With reference to FIG. 44, a first area 719 (e.g., a center region) of the surface 717 can be configured to direct more light into the eye than a second area 721 (e.g., an outer region). For example, the first area 719 can reflect light (e.g., by TIR or by a reflective surface), and the second area 721 can scatter light. Alternatively, the first area 719 of the surface 717 can be configured to scatter light, and the second area 721 of the surface 717 can be configured to absorb light (e.g., having a dark material or light filter). Light can be sent to the surface 717, such as from the light entry surface 713, such that light is distributed across at least apportion of the first area 719 and at least a portion of the second area 721. In some cases the light can be distributed across the full first area 719, the full second area 721, and/or the full surface 717. In some cases the light can be distributed across a majority of the first area 719, a majority of the second 721, and/or a majority of the surface 717. In the embodiment of FIG. 44, the surface 717 can be configured to produce an optical fixation feature having the same of a circular spot. Any other suitable shape can be used. FIG. 45 shows a surface 717 configured to produce an optical fixation feature having the shape of a star. FIG. 46 shows a surface 717 configured to produce an optical fixation feature having the shape of a bright ring with a dimmer area inside the ring. A third area 723 (e.g., inside the ring) can be configured the same as the second area 721, or it can direct a third different amount of light into the eye. The subject can be instructed to look at the center of the ring (which can be dimmer or dark). The center of the ring can be the optical fixation point even though the center of the ring can be less bright than the ring, or can be a dark area inside the ring. In some cases, it can easier for the subject to focus on a dark or dimmer area than to focus on a bright spot or area. FIG. 47 shows an example embodiment have four first areas 719*a-d* configured to direct more light into the eye than a second area 721, which can have the shape of a cross. Many other shapes can be used, such as a bull's eye, an arrow, etc. Each of the embodiments of FIGS. 44-47 can be inverted, so that the areas 719 direct less light in to the eye than the areas 721 or 723.

Many alternatives are possible. In some embodiments, the optical fixation feature can be white light, or can include color (e.g., a red spot). Colored light can be used in some cases to produce a colored optical fixation feature. In some embodiments, the surface 717 and/or the light entry surface 713 can have one or more color filters to produce colored or multicolored light for the optical fixation feature. In some cases, the surface 717 can have a curved shape that produces a shape for the optical fixation feature. For example, the curvature of the surface 717 can reimage the light that impinges on the surface 717 to produce a bright ring, with a dim center region inside the ring, or any other suitable shape. In some cases, ambient light can enter the gonioscope (e.g., through the light entry area or surface 713) to produce the optical fixation feature. In some cases, the gonioscope can include a light source (e.g., a light emitting diode (LED)) and a power supply (e.g., a battery) for powering the light source to produce the optical fixation feature. The LED can be recessed into the gonioscopic optical element 704 (e.g., in the recess 715) or the handle 702. Additional details regarding optical fixation feature embodiments are disclosed in WO 2016/154066, which is incorporated herein by reference.

Figure 48:
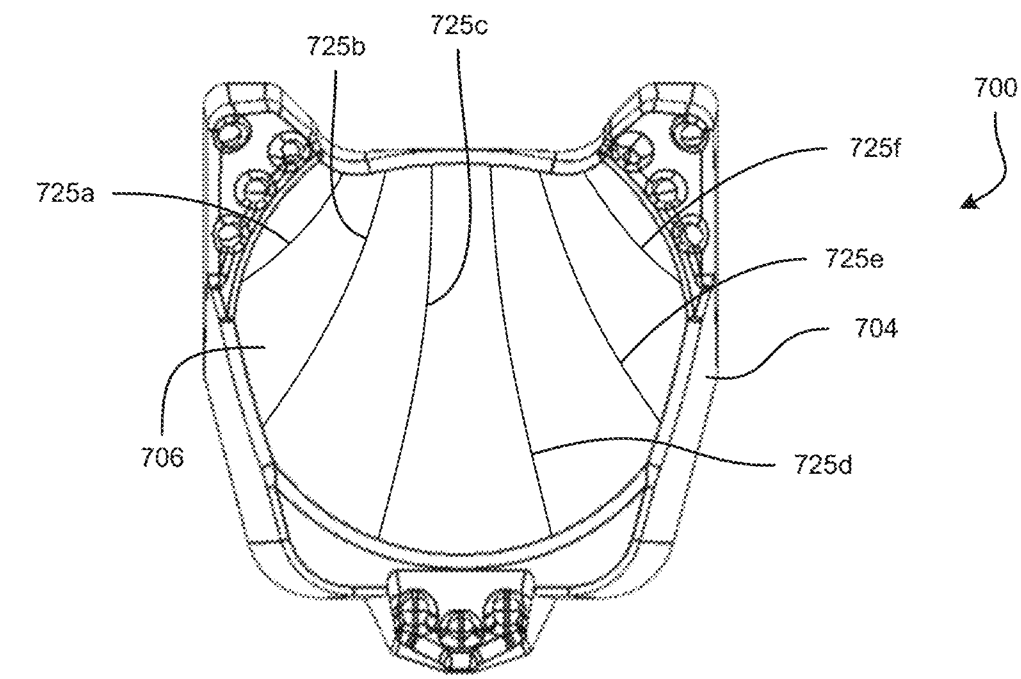
FIG. 48 shows an example embodiment of a gonioscope having markings.
Figure 50:
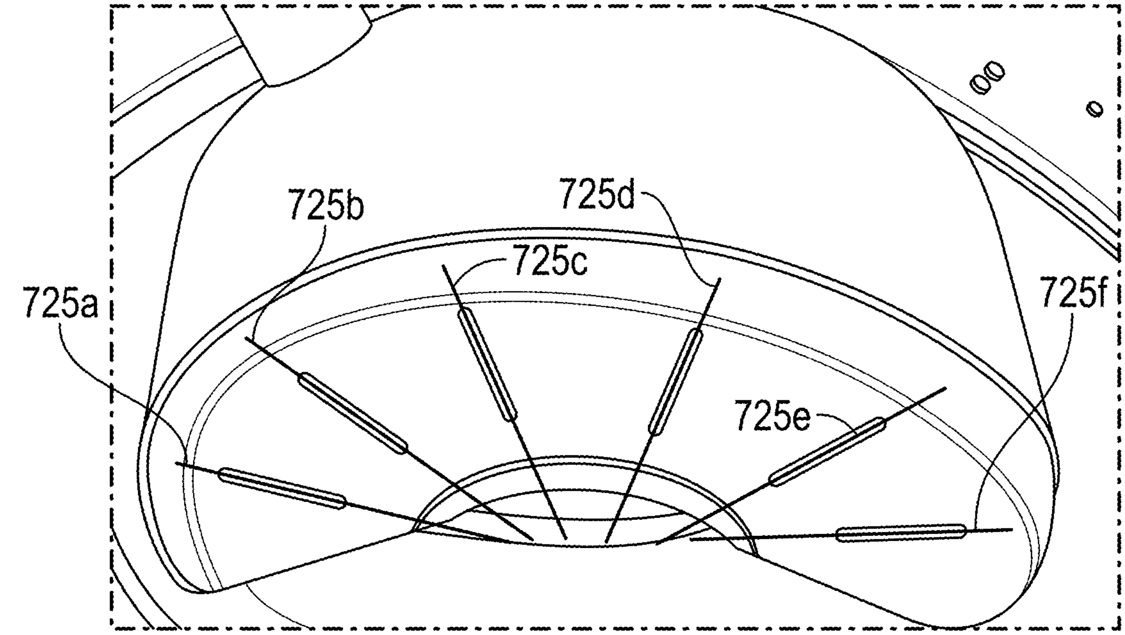
FIG. 50 shows an image resulting from the markings similar to FIG. 48.

In some embodiments, the gonioscope 700 can include one or more markings that are visible in the image produced by the gonioscope 700. The markings can denote angles within the field of view of the image. The markings can divide the image by angle increments. For example, a gonioscope can produce an image having a field of view of 6 clock hours (e.g., 180 degrees), and the markings can divide the image into individual clock hours (e.g., by angles of 30 degrees). The different areas can be denoted by lines or different colors or any other suitable visual features. With reference to FIG. 48, the distal surface 706 of the gonioscopic optical element 704 can have lines 725*a-f*. When the gonioscope 700 of FIG. 48 is used to produce an image, the image can have the lines 725*a-f*, which can be similar to those shown in FIG. 50. The lines 725*a-f* can be positioned on the distal surface 706, such that when shown in the image the lines divide the field of view by angle increments (e.g., by 30 degrees, or by 1 clock hour). More lines or fewer lines can be used, and the gonioscope can be configured to produce a different image having a different field of view than shown in FIG. 50. The markings (e.g., lines) can divide the field of view in the image by angle increments of 5 degrees, 10 degrees, 15 degrees, 20 degrees, 25 degrees, 30 degrees, 35 degrees, 40 degrees, 45 degrees, 50 degrees, 55 degrees, 60 degrees, or any values therebetween, or any ranges bounded by any combination of these values, although other configurations are also possible.

The lines 725*a-f* can be burned (e.g., laser etched) into the gonioscope 700 material (e.g., the distal surface 706). The lines 725*a-f* can be etched into the gonioscope 700 material (e.g., the distal surface 706). The lines 725*a-f* can be drawn onto the gonioscope 700 (e.g., the distal surface 706). The lines 725*a-f* can be an added layer (e.g., added onto the distal surface 706). The lines 725*a-f* can rough or frosted areas (e.g., on the distal surface 706), which can scatter light. The lines 725*a-f* can be made using air gaps.

Figure 49:
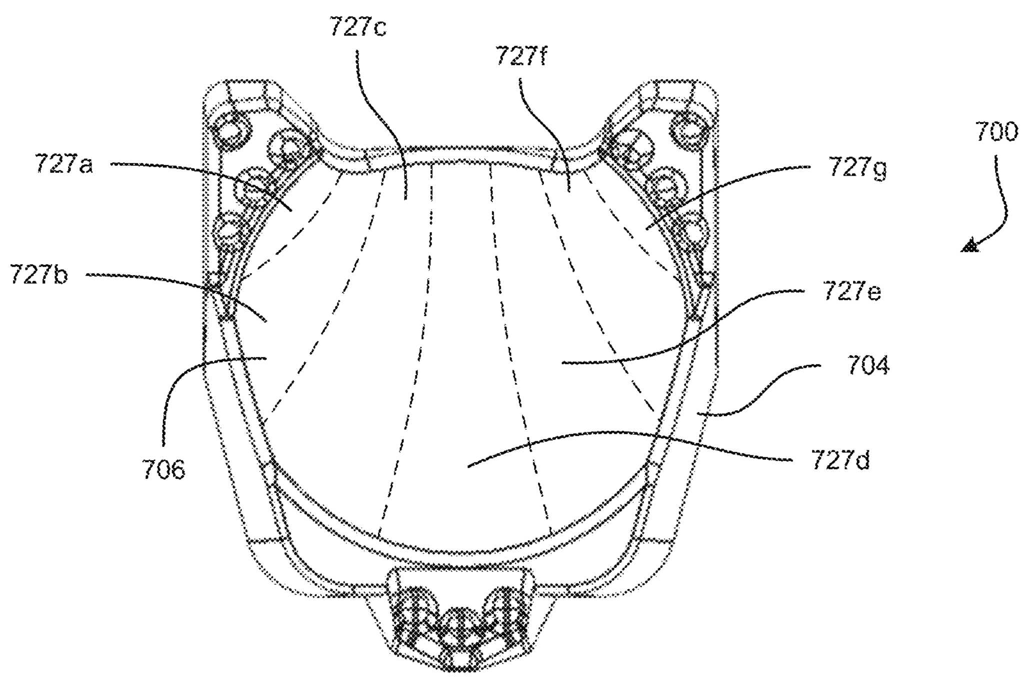
FIG. 49 shows another example embodiment of a gonioscope having markings.
Figure 51:
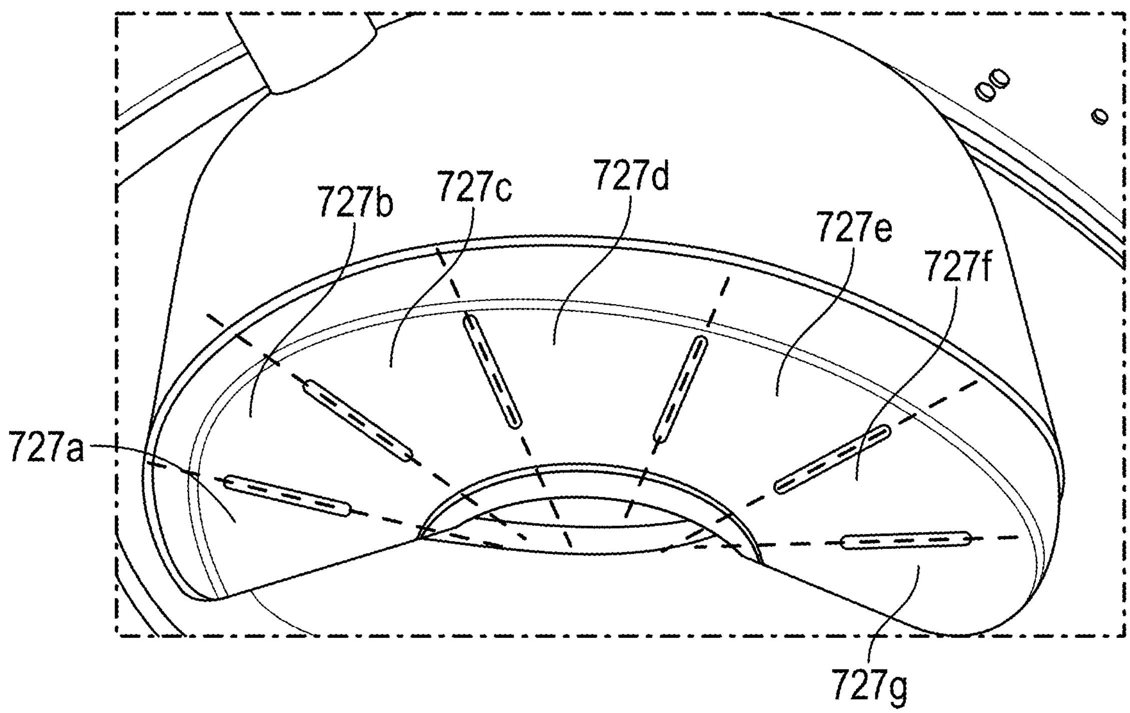
FIG. 51 shows an image resulting from the markings similar to FIG. 49.

FIG. 49 shows can example embodiment of a gonioscope 700 with markings that divide the field of view into areas 727*a-g*. FIG. 51 shows the resulting image. The areas 727*a-g* can have different light transmission properties so that the areas 727*a-g* differ visibly. In some cases, each area can correspond to an angular range (e.g., one clock hour) of the field of view of the image. The areas 727*a-g* can be visually distinct, such as having different colors so that they can be differentiated in the resulting image. The distal surface 706 of the gonioscopic optical element 704 can have a layer with different colors at different areas. In some cases, a different visual parameter (e.g., color) can be used for each of the areas 727*a-g*, or two alternating visual parameters (e.g., colors) can be used. For example areas 727*a*, 727*c*, 727*e*, and 727*g* can have a first visual parameter, such as a color filter coating that produces a red hue to the areas 727*a*, 727*c*, 727*e*, and 727*g* in the resulting image. Areas 727*b*, 727*d*, and 727*f* can have a second visual parameter, such as a color filter coating that produces a green hue to the areas 727*b*, 727*d*, and 727*f* in the resulting image. In some cases, one or more of the areas can be visually unmodified. For example, areas 727*b*, 727*d*, and 727*f* can have no color filter or other visual modifier, which can visually distinguish them from areas 727*a*, 727*c*, 727*e*, and 727*g* that do have a visual modifier (e.g., a color filter). Adjacent areas can have different visual properties so that they can be distinguished visually in the resulting image. In some embodiments, one or more neutral density filters can be used to visually distinguish between adjacent areas. For example, areas 727*a*, 727*c*, 727*e*, and 727*g* can have a neutral density filter while areas 727*b*, 727*d*, and 727*f* do not, which can produce an image that is darker at areas 727*a*, 727*c*, 727*e*, and 727*g* than at areas 727*b*, 727*d*, and 727*f*. Many alternatives are possible. For example, in some embodiments, the markings can be located so that they cover substantially only the portion of the image that corresponds to the trabecular meshwork, or other anatomical feature in the eye. In some embodiments, the markings can be a grid. The markings can be used by a medical practitioner to measure or gauge distances in the eye. This can be particularly useful when the image has magnification in one direction and demagnification in another direction.

Figure 51A:
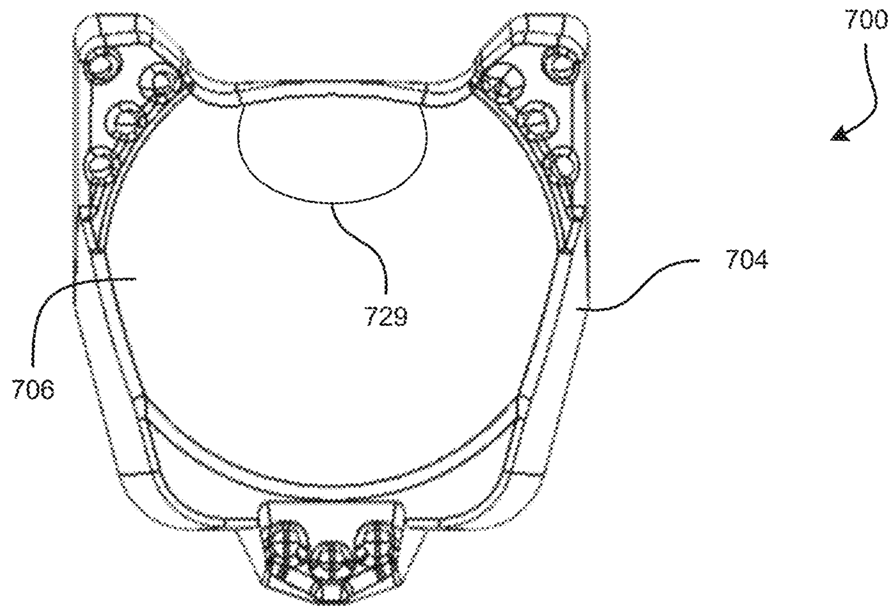
FIG. 51A shows another example of a gonioscope having marking.
Figure 51B:
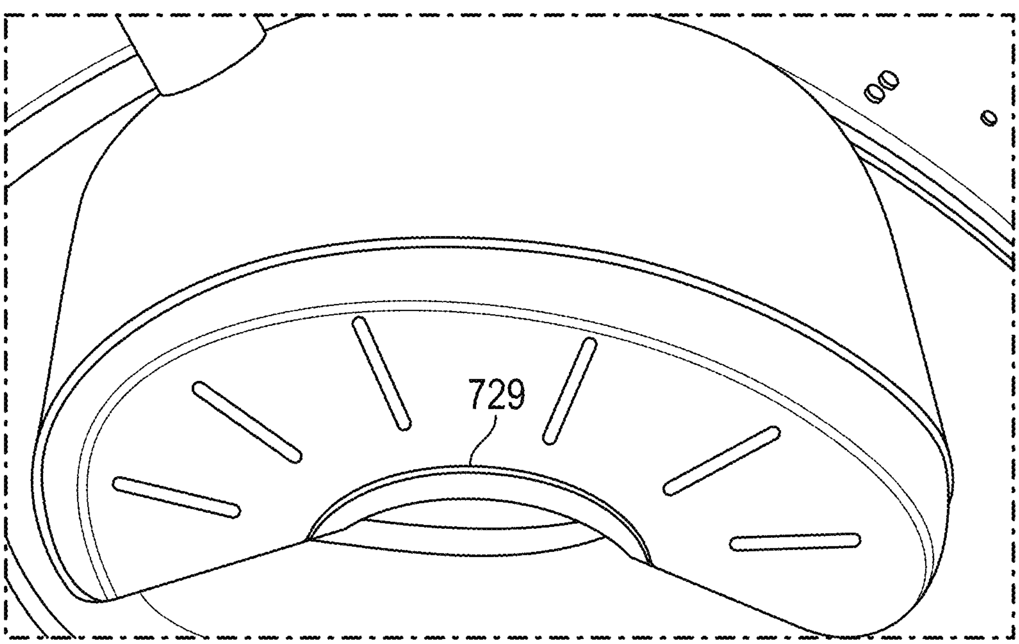
FIG. 51B shows an image resulting from the markings similar to FIG. 51A.
Figure 51C:
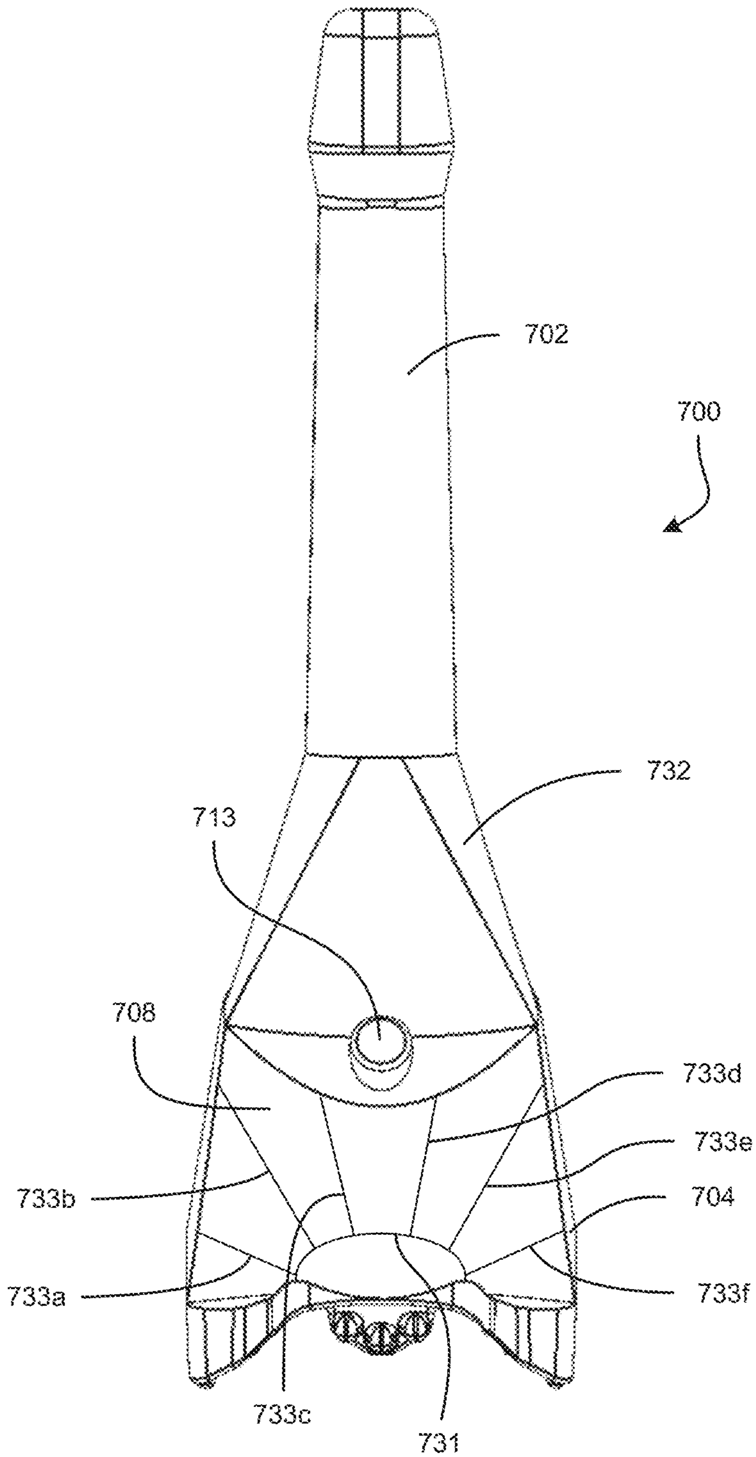
FIG. 51C shows another example of a gonioscope having markings.

In some embodiments, the one or more markings can be positioned so that the one or more markings indicate where the pupil of the eye should be located in the resulting image. FIG. 51A shows an example embodiment of a gonioscope 700 having a marking (e.g. a line 729, or color region, etc.) that at least partially encircles the pupil of the eye as shown in FIG. 51B when the gonioscope 700 is positioned properly. This can provide an indication to the practitioner that the angle of the eye and/or gonioscope 700 is optimally positioned to view the trabecular meshwork. The marking can be an arcuate line 729, a plurality of concentric lines which can correspond to different pupil sizes, a plurality of dots, arrows, or other markings along an arcuate path configured to correspond with the pupil in the resulting image, as discussed herein. In some embodiments, the one or more markings (e.g., line 727) corresponding to the pupil can be used together with the markings indicating angles in the image (e.g., lines 725*a-f*). For example, FIG. 51C shows can example embodiment having an arcuate line 731 that is configured to align with the pupil of the eye in the resulting image, and lines 733*a-f* that extend outward from the line 731 to indicate angular regions in the resulting image. Various other combinations of markings can be used.

Also, in FIG. 51C, the markings are positioned on the proximal surface 708 of the gonioscopic optical element. Any of the markings discussed herein can be positioned on the proximal surface 708, or the distal surface 706, or embedded in the gonioscopic optical element 704 (e.g., between the proximal surface 708 and the distal surface 706. In some cases, markings on the distal surface 706 can be more focused in the image viewed by the practitioner, because the distal surface 706 is closer to the target structure than the proximal surface 708. Accordingly, it can be advantageous to have the one or more markings on the distal surface 706. However, in some cases, it may be advantageous to have the one or more markings somewhat out of focus in the image seen by the practitioner, since this may make the markings less distracting while performing an implantation or other procedure. The one or more markings can be embedded in the gonioscopic optical element 704 by using two gonioscopic optical element portions that are joined (e.g., glued, sonic welded, laser welded, etc.). The one or more markings can be on the inside surface of one or both of the gonioscopic optical element portions. The one or more markings can be formed by voids (e.g., air gaps) between the two portions. For example, one or more recesses, trenches, protrusions, or ridges can be formed in one or both of the gonioscopic optical element portions to form the one or more voids to produce the one or more markings. In some embodiments, laser etching can be used to produce one or more markings inside the gonioscopic optical element 704.

In some embodiments, the gonioscope 700 can be used with a support 750, which can be configured to support the gonioscope 700 during use. In some cases, the support 750 can enable the gonioscope 700 to be used hands-free, without the practitioner holding the handle 702 or otherwise touching the gonioscope 700. The practitioner can hold the handle to position the gonioscope 700, and once positioned with the support engaged, the practitioner can release the handle 702. This can enable the practitioner to use both hands for a procedure, and can also impede unintended movement of the gonioscope 700, which can occur if the gonioscope 700 is held throughout a medical procedure. In some embodiments, the support 750 can be used even if the gonioscope 700 is being held. The support 750 can impede movement of the gonioscope 700 relative to the eye. In some embodiments, the handle 702 can be omitted.

The support 750 can be made of a different material than the gonioscopic optical element 704 and/or than the handle 702. The support 750 can be made of a more flexible material than the gonioscopic optical element 704 and/or than the handle 702. For example, the support 750 can be made of a silicone material, a hydrogel material, or any other suitable material. The support 750 can be a separately formed from the gonioscopic optical element 704 and/or the handle 702. The support 750 can be removably attachable to the gonioscope 700. The support 750 can include one or more engagement features that are configured to engage corresponding engagement features on the gonioscope 700 to attach the support 750 to the gonioscope 700.

Figure 52:
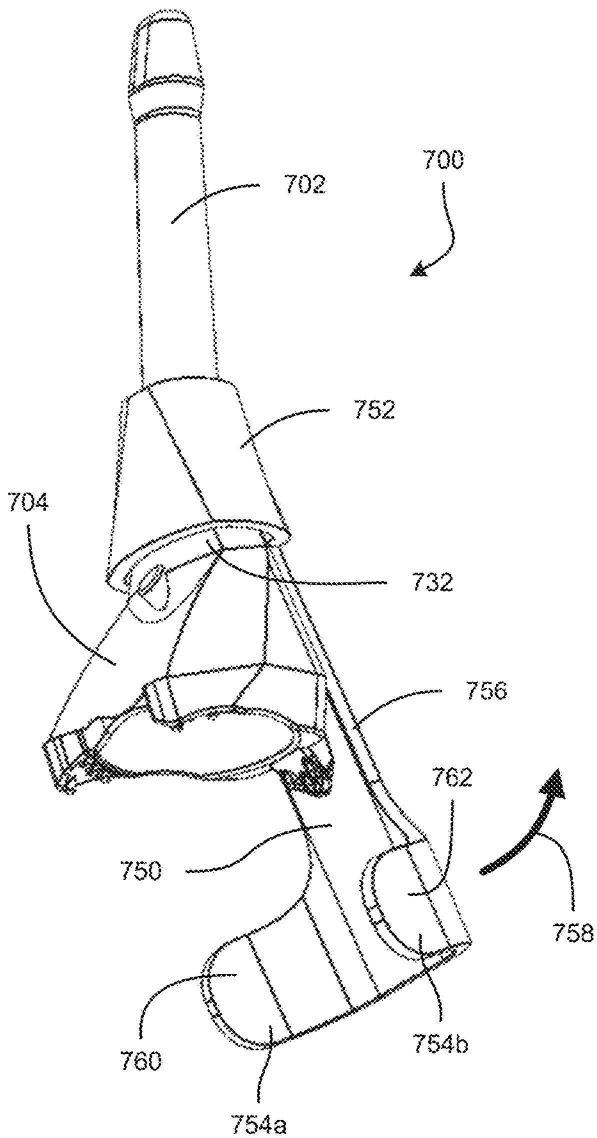
FIG. 52 is a bottom-front perspective view of an example embodiment of a support being used with a gonioscope.
Figure 53:
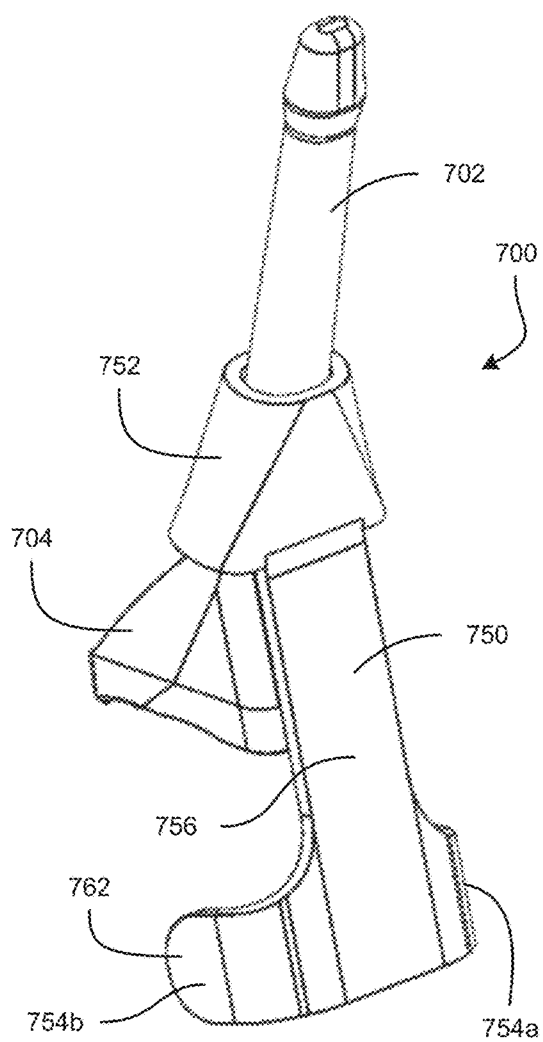
FIG. 53 is a top-rear perspective view of an example embodiment of a support being used with a gonioscope.

With reference to FIGS. 52 to 53, the support 750 can be configured to engage the handle 702 of the gonioscope 700. The support 750 can include a handle attachment 752. The handle attachment 752 can have a through hole that is configured to receive the handle 702. The handle attachment 752 can have an internal shape that generally corresponds to the outer shape of the junction area 732, so that the handle attachment 752 can seat onto the junction area 732. The internal shape of the handle attachment 752 can be tapered (e.g., having a bottom opening larger than a top opening). The junction area 732 can be tapered (e.g., having a lower area that is larger than an upper area). The taper of the handle attachment 752 can generally correspond to the taper of the junction area 732. The top of the handle 702 can be passed through the handle attachment 752, and the handle attachment 752 can slide down the handle 702 until it seat with the junction area 732, the widening handle 702, and/or the gonioscopic optical element 704. Gravity and/or friction can impede the handle attachment 752 from moving up the handle 702.

The support 750 can include one or more eye engagement structures that are configured to engage one or more corresponding portions of the eye to support the gonioscope 700. With reference to FIGS. 52 and 53, the support 750 can include a right flap 754*a* and a left flap 754*b*. The right flap 754*a* can be configured to engage a first eyelid (e.g., an upper eyelid or a lower eyelid), and the left flap 754*b* can be configured to engage a second eyelid (e.g., the lower eyelid or the upper eyelid). The flaps 754*a-b* can engage the upper or lower eyelids respectively, depending on the whether the gonioscope 700 is being used with the right or left eye, and/or depending on the orientation of the gonioscope 700. In some embodiments, a single flap can be used to engage only one eyelid. A neck portion 756 can couple the handle attachment 752 to the flaps 754*a-b*. The neck portion 756 can extend downward (e.g., distally) from a back side of the handle attachment 752. The flaps 754*a-b* can extend from the right and left sides of the distal end of the neck portion 756. The neck portion 756 can extend along the back side of the gonioscopic optical element 704. The neck portion 756 can be flexible. When in use, the neck portion 756 can flex (e.g., in the direction of arrow 758 in FIG. 52) so that flaps 754*a-b* lay against the eye. The flaps 754*a-b* can have a distal side 760 that faces towards the eye (e.g., downward) and a proximal side 762 that faces away from the eye (e.g., upward), when in use. The distal side 760 can contact the sclera of the eye. The flaps 754*a-b* can engage anatomy adjacent the eye of the subject. The flaps 754*a-b* can fit between the eye and the respective eyelids. The eyelid can press down on the flap 754*a* or 754*b* to hold the support 750 against the eye. The proximal surface 762 can include texture, such as bumps, recesses, protrusions, ridges, cleats, and the like, to engage the underside of the eyelid. The distal surface 760 can include texture, such as, recesses, protrusions, ridges, cleats, and the like, to engage the tissue of the eye (e.g., the sclera). The support 750 can press the gonioscope against the eye, which can cause the retention elements 744 to engage the eye tissue (e.g., the sclera). Thus the support 750 and the retention elements 744 can work together to hold the gonioscope 700 onto the eye.

With reference to FIGS. 54 and 55, the support 750 can be configured to engage an arm 746 of the gonioscope 700. The gonioscope 700 can have an arm 746 extending from a back side of the gonioscopic optical element 704. The arm 746 can have one or more retention elements 744, as discussed herein. The support 750 can include an arm attachment 764. The arm attachment 764 can have a recess configured to receive the arm 746 therein. The arm 746 can be inserted into the recess to couple the support 750 to the gonioscope 700. Friction can hold the arm 746 in the recess during use. The retention elements 744 can engage the material of the support 750 to facilitate the coupling. The support 750 of FIGS. 54 and 55 can have flaps 754*a-b* similar to the embodiment of FIGS. 52 and 53.

With reference to FIGS. 56 and 57, the support 750 can engage a corner of the eye (e.g., at or near the punctum). The support 750 can have a flap 766, with a distal surface 768, and a proximal surface 770. The flap 766 can be flexible. When in use, the flap 766 can flex back and upward (e.g., similar to the flexible neck 756 discussed in connection with FIG. 52). The flap 766 can fit between the eye and the anatomy adjacent the eye. For example, the flap 766 can slide under one or both of the upper eyelid and the lower eyelid. The flap 766 can fit between the eye and the canthus, the puntum, or other structure adjacent the eye. The flap 766 can have a distal side 768 that faces towards the eye (e.g., downward) and a proximal side 770 that faces away from the eye (e.g., upward), when in use. The distal side 768 can contact the sclera of the eye. The proximal surface 770 can include texture, such as bumps, recesses, protrusions, ridges, cleats, and the like, to engage the underside of the structure adjacent the eye. The distal surface 768 can include texture, such as, recesses, protrusions, ridges, cleats, and the like, to engage the tissue of the eye (e.g., the sclera). FIGS. 56 and 57 show the support 750 attached using an arm attachment 764, although any suitable type of attachment can be used.

Figure 58:
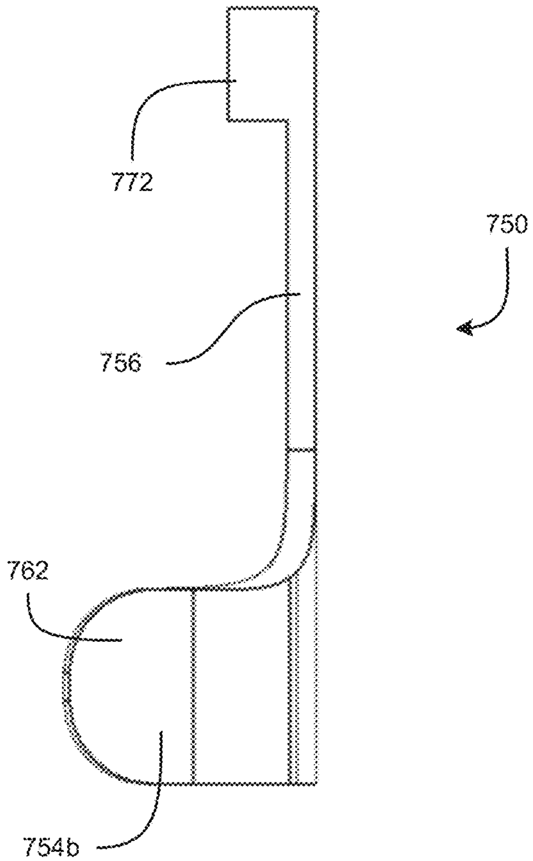
FIG. 58 is a side view of an example embodiment of a support for use with a gonioscope.
Figure 59:
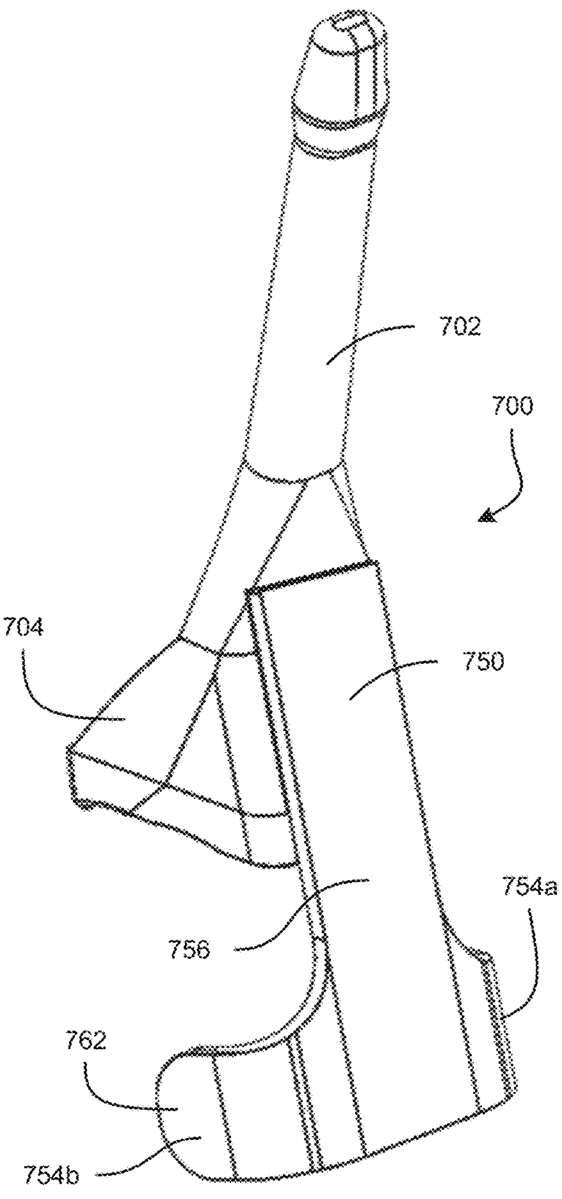
FIG. 59 is a top-rear perspective view of an example embodiment of a support being used with a gonioscope.

With reference to FIGS. 58 and 59, in some embodiments, the support 750 can engage the recess 715. The support 750 can have a protrusion 772 that is shaped to press fit into the recess 715. The protrusion 772 can have a shape that generally conforms to the shape of the recess 715 (e.g., a cylinder). In some cases, the protrusion 772 can be slightly larger than the recess and can be flexible so that the protrusion deforms (e.g., compresses) when it is inserted into the recess 715. The recess 715 can be deeper than the protrusion 772, so that when the protrusion 772 is fully inserted into the recess 715 there is still an air gap between the protrusion 772 and the base surface 717 (e.g., to facilitate TIR as discussed herein). The support 750 can have a neck 758, which can be flexible as discussed herein. The support 750 of FIGS. 54 and 55 can have flaps 754*a-b* similar to the embodiment of FIGS. 52 and 53.

Figure 59A:
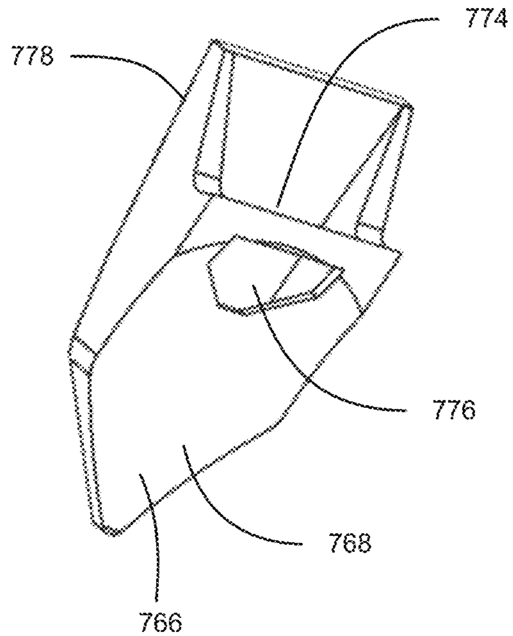
FIG. 59A is a perspective view of an example embodiment of a support for use with a gonioscope.
Figure 59B:
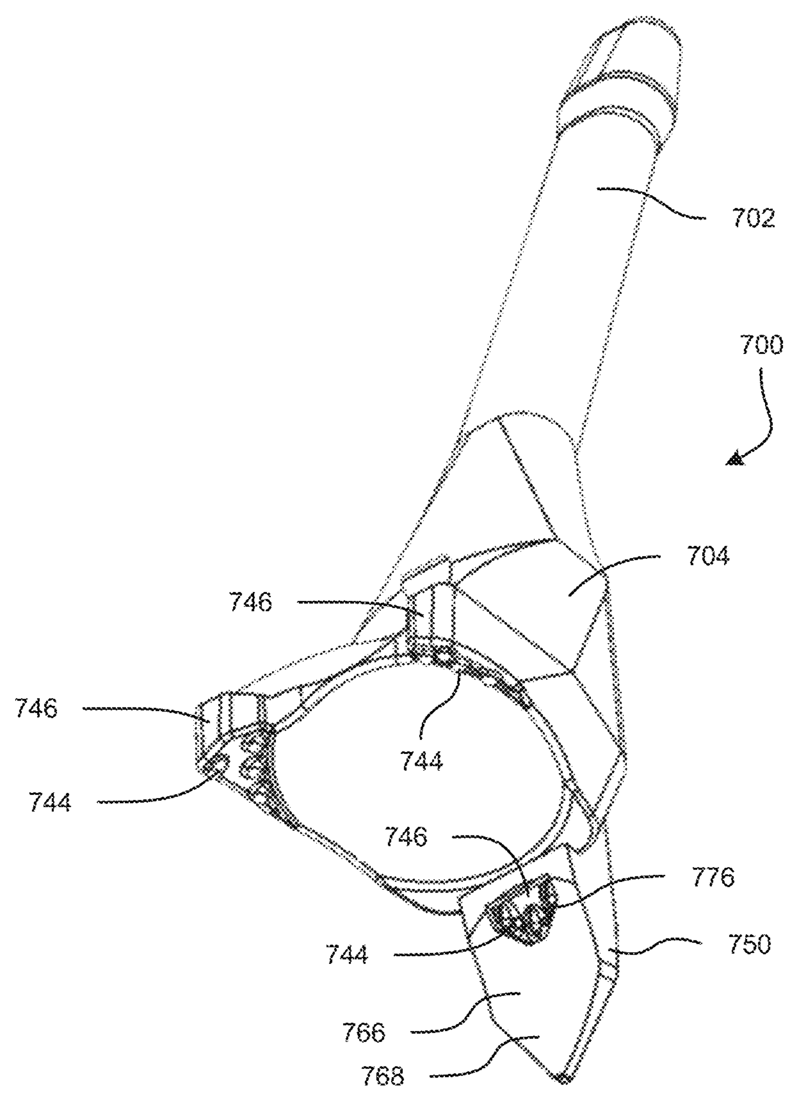
FIG. 59B is a bottom-front perspective view of the support coupled to a gonioscope.
Figure 59C:
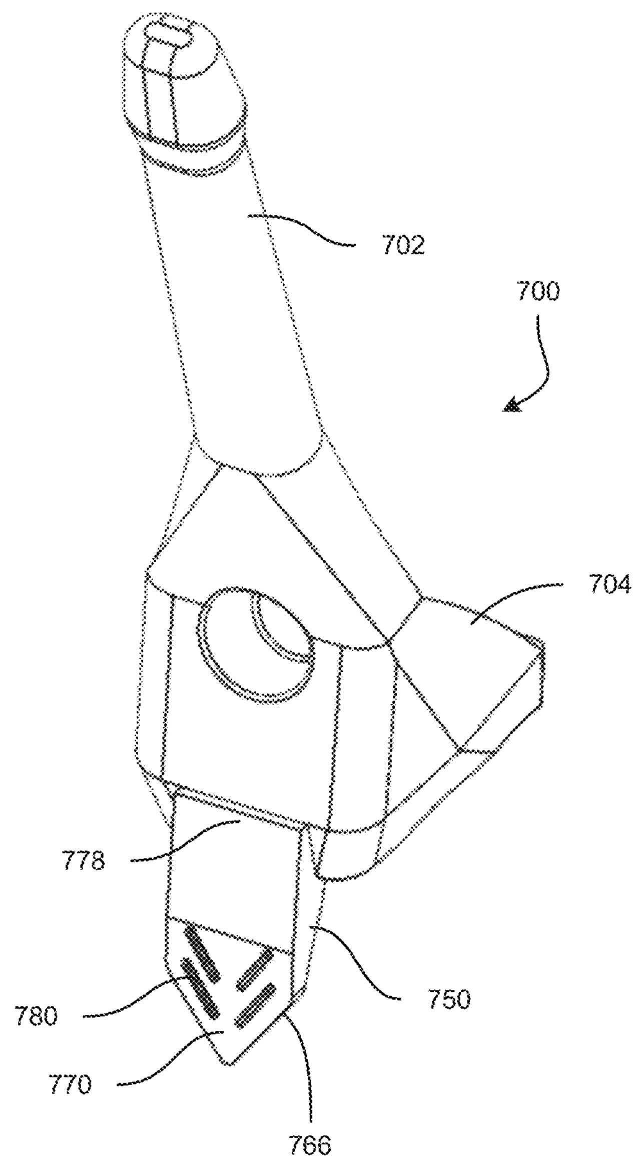
FIG. 59C is a top-rear perspective view of the support coupled to the gonioscope.

FIG. 59A is a perspective view of an example embodiment of a support 750 for use with a gonioscope. FIG. 59B is a bottom-front perspective view of the support 750 coupled to a gonioscope 700. FIG. 59C is a top-rear perspective view of the support 750 coupled to the gonioscope 700. The support 750 of FIG. 59A can be similar to the embodiment of FIGS. 56 and 57, although features of any of the supports disclosed herein can be used combined or interchanged. The support 750 can include a recess 774, which can be configured to receive an arm 746 of the gonioscope 700, such as the back arm that extends from the back side of the gonioscopic optical element 704. The inner surface of the recess 744 can be generally sized and shaped to correspond to the outer surface of the arm 746. The support 750 can have an opening 776 configured to align with one or more retention elements 744 on the arm 746 when the arm 746 is inserted into the recess 774. The one or more retention elements 744 can extend into or through the opening 776. The engagement between the one or more retention elements 744 and the opening 776 can hold the support 750 onto the arm 746. Also, when placed on the eye, the opening 776 can permit the retention elements 744 to engage the eye (e.g. the sclera) as described herein.

The support 750 can include a back wall 778 that is configured to extend up a portion of the back side of the gonioscope 700 when the support 750 is attached thereto (as can be seen in FIG. 59C). The support 750 can engage a corner of the eye. The support 750 can have a flap 766, with a distal surface 768, and a proximal surface 770. The flap 766 can be flexible. When in use, the flap 766 can flex back and upward. The flap 766 can fit between the eye and the anatomy adjacent the eye. The flap 766 can fit between the eye and the canthus, the puntum, or other structure adjacent the eye. The flap 766 can have a tapered or pointed end to facilitate the flap 766 engaging the corner of the eye. The flap 766 can have a distal side 768 that faces towards the eye (e.g., downward) and a proximal side 770 that faces away from the eye (e.g., upward), when in use. The distal side 768 can contact the sclera of the eye. The proximal surface 770 can include texture 780, such as bumps, recesses, protrusions, ridges, cleats, and the like, to engage the underside of the structure adjacent the eye. The distal surface 768 can include texture, such as, recesses, protrusions, ridges, cleats, and the like, to engage the tissue of the eye (e.g., the sclera).

FIG. 59D is a bottom-front perspective view of another example embodiment of a support 750, shown coupled to a gonioscope 700. FIG. 59E is a top-rear perspective few of the support 750 coupled to the gonioscope 700. The support 750 can attach to an arm 746 of the gonioscope 700, similar to the discussion regarding FIGS. 59A-C, although any suitable attachment mechanism or manner can be used. The support 750 can include a recess 774, which can be configured to receive an arm 746 of the gonioscope 700. The support 750 can have an opening 776 configured to align with one or more retention elements 744 on the arm 746 when the arm 746 is inserted into the recess 774. The support 750 can include a back wall 778 that is configured to extend up a portion of the back side of the gonioscope 700 when the support 750 is attached thereto.

The support 750 can include flaps or wings, such as a right wing or flap 754*a* and a left wing or flap 754*b*, a shown in FIGS. 59D and 59E. The right flap 754*a* can be configured to engage a first eyelid (e.g., an upper eyelid or a lower eyelid), and the left flap 754*b* can be configured to engage a second eyelid (e.g., the lower eyelid or the upper eyelid). The flaps 754*a-b* can engage the upper or lower eyelids respectively, depending on the whether the gonioscope 700 is being used with the right or left eye, and/or depending on the orientation of the gonioscope 700. In some embodiments, a single flap can be used to engage only one eyelid. The support 750 can have a neck portion 756 that can be flexible. When in use, the neck portion 756 can flex (e.g., rearward and/or upward) so that flaps 754*a-b* lay against the eye. Either or both of the flaps 754*a-b* can have a distal side 760 that faces towards the eye (e.g., downward) and a proximal side 762 that faces away from the eye (e.g., upward), when in use. The distal side 760 can contact the sclera of the eye. The flaps 754*a-b* can engage anatomy adjacent the eye of the subject. The flaps 754*a-b* can fit between the eye and the respective eyelids. The eyelid can press down on the flap 754*a* or 754*b* to hold the support 750 against the eye. The proximal surface 762 can include texture 780, such as bumps, recesses, protrusions, ridges, cleats, and the like, to engage the underside of the eyelid. The distal surface 760 can include texture (not shown), such as, recesses, protrusions, ridges, cleats, and the like, to engage the tissue of the eye (e.g., the sclera).

The attachment mechanisms and other features of the supports 750 of FIGS. 52 to 59E can be interchanged and/or combined. For example, a support 750 can include a handle attachment 752 (e.g., similar to FIG. 52) and an arm attachment 764 (e.g., similar to FIG. 54). A support 750 can have a handle attachment 752 and a protrusion 772 for engaging a recess 715 (e.g., similar to FIGS. 58 and 59). A support 750 can have an arm attachment 764 and a protrusion 772 for engaging a recess 715. A support 750 can have a handle attachment 752, an arm attachment 764, and a protrusion 772 for engaging a recess 715. Any suitable attachment mechanism can be used to couple the support 750 to the gonioscope 700. The support 750 can be adhered to the gonioscope 700, over molded onto the gonioscope 700, secured to the gonioscope 700 by a separate fastener, sonically welded, etc. The supports 750 disclosed herein can be used with any gonioscope embodiment disclosed herein. Any suitable structure can be used to engage the anatomy of the subject to provide support for the gonioscope 700.

Any of the gonioscopes disclosed herein can include retention elements for impeding movement of the gonioscope relative to the eye. The gonioscope 700 can have retention elements 744, which can be an integral part of the gonioscope 700. The retention elements 744 can be integrally formed with the gonioscopic optical element 704 and/or the handle 702. The retention elements 744 can be made of the same material as the gonioscopic optical element 704 and/or the handle 702. The gonioscope 700 can include a plurality of retention elements 744 coupled to the gonioscopic optical element 704 and configured to engage an eye to retain the gonioscope 700 relative to the eye, similar to the other retention element embodiments disclosed herein. The plurality of retention elements 744 can be stationary relative to the gonioscopic optical element 704. Any of the various types of retention elements 744 disclosed herein can be used for the gonioscope 700, or any of the other gonioscopes disclosed herein. For example, the gonioscope 700 can include one or more arms 746 with one or more retention elements 744 on distal portions of the arms 746. In some embodiments, the arms 746 can extend from the gonioscopic optical element 704. The arms 746 can extend distally, and in some cases can extend distally past the distal surface 706 of the gonioscopic optical element 704. The arms 746 can extend radially outward. The retention elements 744 can be configured to engage the sclera of the eye and can be configured to not contact the cornea. The retention elements 744 can be configured to restrain movement of the eye relative to the gonioscope 700. The retention elements 744 can be configured to orient the gonioscopic optical element 704 relative to the eye to facilitate viewing into the eye.

The retention elements 744 can be located on the distal side of the gonioscope 700. For example, the retention elements 744 can be adjacent to the distal surface 706. The retention elements 744 can be configured to contact certain portions of the patient's eye, while avoiding contact with other portions. For example, the retention elements 744 can be configured to contact the sclera and/or conjunctival tissue, while avoiding contact with the cornea. The retention elements 744 can be configured to contact the sclera of the eye when the gonioscope 700 is positioned for viewing an anterior chamber of the eye. The retention elements 744 can be configured to not contact the cornea of the eye when the gonioscope 700 is positioned for viewing an anterior chamber of the eye. The retention elements 744 can comprise atraumatic structures. The retention elements 744 can comprise a multi-point contact structure with multiple contact points configured to be distributed around the eye, such as on the area surrounding the cornea. The retention elements 744 can have minimal contact surface area, in some cases.

The retention elements 744 and/or the arms 746 can be made of the same material as the gonioscopic optical element 704, and can be integrally formed therewith. In some embodiments, the gonioscopic optical element 704 and the retention elements 744 can comprise different materials. For example, the gonioscopic optical element 704 can comprise a glass or plastic material, while the retention elements 744 can comprise a textile, cloth, or fabric material. Various other materials can be used for the retention elements 744, in some implementations, such as metal or ceramic materials. The user can place the gonioscope 700 on a subject's eye 100. The retention elements 744 can engage the eye to retain the gonioscope 700 relative to the eye.

The retention elements 744 can be disposed on a generally circular path. The retention elements 744 can be disposed on a generally circular path that can have a circumference larger than the circumference of the cornea, such that the retention elements 744 do not contact the cornea during clinical use. The outer circumference of the retention elements 744 can avoid contacting the lid speculum. By way of example, the retention elements 744 can be disposed on a generally circular path that has a diameter that is at least about 10 mm, at least about 11 mm, at least about 12 mm, at least about 13 mm, at least about 14 mm, or at least about 15 mm, or any value or ranges therebetween, although values outside these ranges can be used in some implementations. In some embodiments, the retention elements 744 can be disposed on a generally circular path that has a diameter that is less than or equal to about 20 mm, less than or equal to about 15 mm, less than or equal to about 14 mm, less than or equal to about 13 mm, or less than or equal to about 12 mm, or any values or ranges therebetween, although values outside these ranges can be used in some implementations.

The retention elements 744 can be positioned to be distributed around the gonioscope across a circumferential angle of at least about 220 degrees, at least about 230 degrees, at least about 250 degrees, at least about 270 degrees, at least about 290 degrees, or more. For example, the one or more arms 746 can be positioned to distribute the retention elements 744 around the gonioscope 700 across the circumferential angle. In some embodiments, the retention elements 744 can be positioned to be distributed around the gonioscope 744 across a circumferential angle of less than or equal to about 320 degrees, less than or equal to about 310 degrees, less than or equal to about 290 degrees, less than or equal to about 270 degrees, less than or equal to about 250 degrees, or less. In some embodiments, the retention elements 744 can be positioned to be distributed around the gonioscope across a circumferential angle of about 270 degrees. The retention elements 744 can be positioned to be distributed around the gonioscope such that each gap between adjacent retention elements has a circumferential angle that is less than or equal to about 145 degrees, less than or equal to about 135 degrees, less than or equal to about 120 degrees, less than or equal to about 105 degrees, less than or equal to about 90 degrees, less than or equal to about 75 degrees, less than or equal to about 60 degrees, or less. The retention elements 744 can be positioned to be distributed around the gonioscope such that at least one of the gaps between adjacent retention elements has a circumferential angle that is at least about 60 degrees, at least about 75 degrees, at least about 90 degrees, at least about 105 degrees, at least about 120 degrees, or more. The retention elements 744 can be distributed to restrain movement of the gonioscope 700 relative to the eye in various different directions.

The plurality of retention elements 744 can be configured to engage the eye without causing trauma to the eye. The retention elements 744 can be atraumatic, and can comprise an atraumatic shape. The atraumatic retention elements 744 can have a shape that is sufficiently blunt that the retention elements 744 do not pierce or cause other trauma to the eye when pressed against the eye (e.g., against the sclera) during clinical use, while also restraining movement between the eye and the gonioscope 700. For example, the atraumatic retention elements 744 can include protrusions that can be pressed against the tissue of the eye (e.g., the sclera) to deform the tissue of the eye without piercing into the tissue of the eye. The retention element structures that are configured to engage the eye can have a minimum radius of curvature of about 0.002 inches or more, of about 0.003 inches or more, of about 0.004 inches or more, of about 0.005 inches or more, of about 0.007 inches or more, of about 0.009 inches or more, of about 0.01 inches or more, or of about 0,012 inches or more. The retention element structures that are configured to engage the eye can have at least a portion with a radius of curvature that is less than or equal to about 0.02 inches, less than or equal to about 0.015 inches, less than or equal to about 0.012 inches, less than or equal to about 0.01 inches, less than or equal to about 0.009 inches, less than or equal to about 0.008 inches, less than or equal to about 0.007 inches, less than or equal to about 0.006 inches, or less than or equal to about 0.0057 inches. Values outside these ranges can be used for the radii of curvature on the retention elements, in some implementations.

The retention elements 744 shown and described herein can have various different shapes. The retention elements 744 can include generally V-shaped retention elements. In some embodiments, retention elements having different shapes can be used on one gonioscope. The retention elements 744 can be one or more ridges (e.g., parallel or V-shaped), one or more cleats, etc. The retention elements 744 can have a generally frustoconical shape. Various different numbers of retention elements 744. For example, each of the arms 746 (or any other suitable location on the gonioscope 700) can have one, two, three, four, five, six, eight, ten, fifteen, twenty retention elements 744, or more or any range bounded by any of the values listed above.

Intraoperative eye movement of a patient can be reduced or restrained by the patient. In some embodiments, a gonioscope can include a fixation point or feature that is visible to the patient. For example, a practitioner can instruct a patient to gaze at a certain fixation point to restrain eye movement. A gonio scope optical element can be configured to produce an optical fixation point. The optical fixation point can be located in the optical path of a patient. Optical fixation points can be used to help a patient orient their eye to align with the gonioscopic optical element and/or a microscope. The fixation point can be used with the gonioscopes described herein during procedures and treatments such as, for example, glaucoma surgery (e.g., minimally invasive glaucoma surgery (MIGS), laser trabeculoplasty (e.g., SLT/ALT), fundus laser, vitrectomy laser, and suture lysis optics where ocular retention and eye/lens stabilization would be beneficial. The fixation point can be actively illuminated (e.g., by an LED) or passively illuminated (e.g., with light emitted from a microscope light or ambient light). Multiple fixation points differentiated via color and/or shape may allow a user, such as a physician or other medical practitioner, to further refine the patient's eye orientation. An optical fixation point can be used to orient the eye of the patient. Multiple optical fixation points can be used to further help orient the eye to the gonioscopic optical element.

FIGS. 60A to 60J are schematic drawings of different views of some example embodiments of a optical fixation point used with a gonioscopic optical element, which can be applied to any of the embodiments disclosed herein. The gonioscopic optical element 928 can comprise a proximal surface 928A and a distal surface 928B. In some embodiments, the gonioscopic optical element 928 can include a thick side 928C, and a thin side 928D. The optical fixation point 960 can be configured to be visible to the subject when the gonioscope is positioned on the eye. The optical fixation point 960 can be located on the thick side 928C of the gonioscopic optical element 928. The location of the optical fixation point 960 can be configured to provide a desired viewing angle (e.g., for a medical practitioner to use in examining and/or operating on the patient's eye). For example, the location of the optical fixation point 960 can be such that when a patient looks directly at the optical fixation point 960, the medical practitioner can view a desired structure of the inside of the eye (e.g., the anterior chamber angle) through the proximal surface of the gonioscopic optical element 928.

Figure 60A:
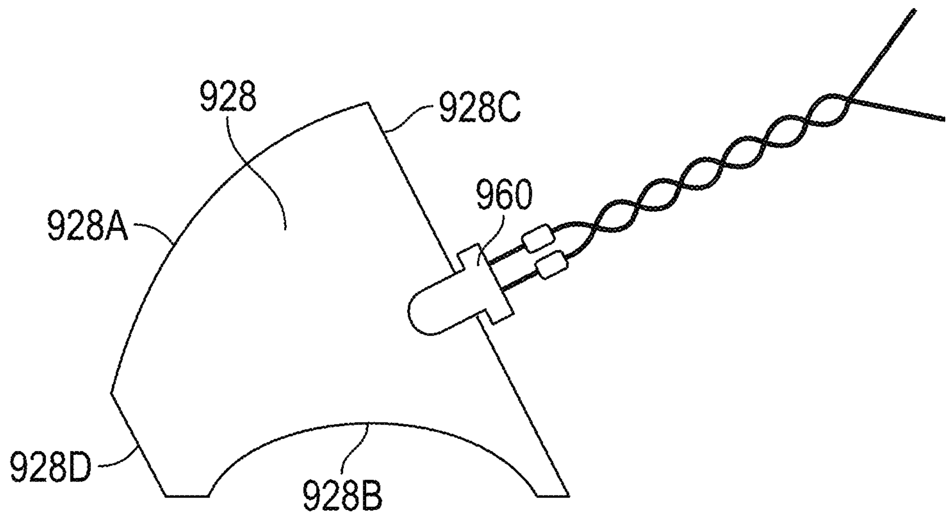
FIGS. 60A and 60B are schematic side views of different example embodiments of a gonioscopic optical element having at least one fixation point.

As shown in FIG. 60A, the optical fixation point 960 can be implemented using a light source. For example, the optical fixation point 960 can made using a light emitting diode (LED), although other types of light sources can also be used. The gonioscope can include a power source, such as a battery, which can be contained in or on the handle of the gonioscope, or any other suitable location. The power source can provide electrical power to one or more light sources to provide one or more fixation elements. The optical fixation point 960 can be actively illuminated. In some embodiments, the gonioscopic optical element 928 can include a recess (e.g., on the thick side 928C, as shown in FIG. 9A), and the light source can be at least partially disposed in the recess.

Figure 60B:
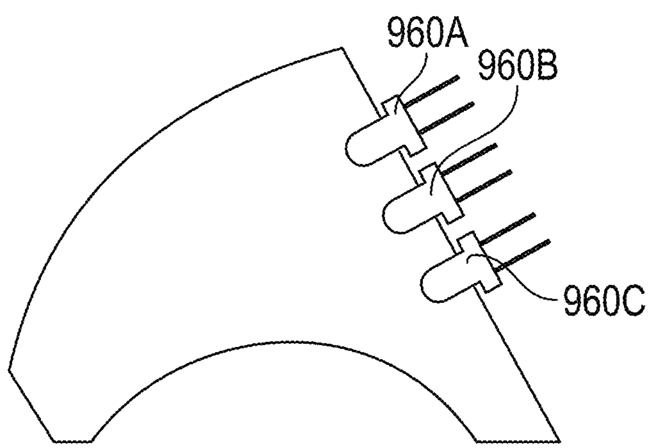
Figure 60C:
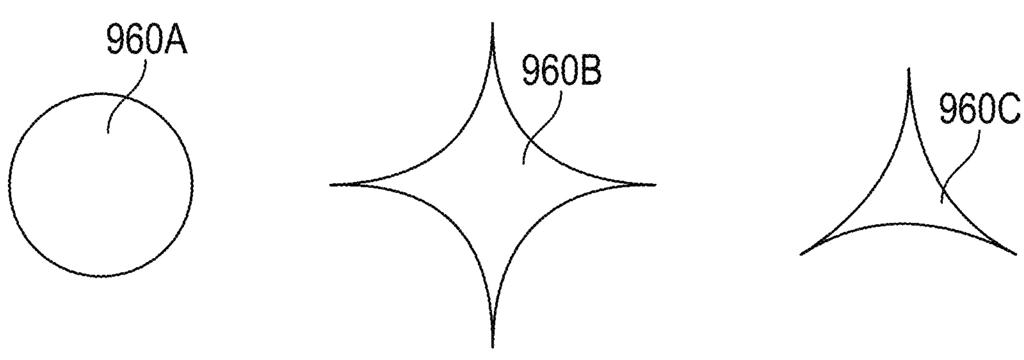
FIG. 60C is a schematic drawing of different example embodiments of multiple gonioscopic fixation points.

As shown in FIG. 60B, an optical fixation point can include multiple fixation points 960A, 960B, 960C. In one embodiment, the multiple fixation points can comprise a first fixation point 960A, a second fixation point 960B, and a third fixation point 960C. The multiple fixation points 960A-C can be made using different light sources, similar to the description of the fixation point 960 in connection with FIG. 60A. The multiple fixation points 960A, 960B, 960C can be aligned along a linear path, although other special arrangements can be used depending on the desired orientation of the gonioscope relative to the eye. For example, when the eye is focused on a first fixation point 960A, the gonioscopic optical element 928 can be oriented relative to the eye to facilitate viewing a first structure or area in the eye, and when the eye is focused on the second fixation point 960B, the gonioscopic optical element 928 can be oriented relative to the eye to facilitate viewing a second structure or area in the eye. A third fixation point 960C can similarly be used to facilitate viewing a third structure or area in the eye, and additional fixation points can be used to facilitate viewing still additional structures or areas in the eye. The multiple fixation points 960A, 960B, 960C can comprise different appearances and different locations. For example, as shown in FIG. 60C, the first point 960A can comprise a circular shape, the second point 960B can comprise a star-shape, and the third point 960C can comprise a triangular shape, although various different shapes and other appearances can be used. In some embodiments, the different fixation points can have different colors. The multiple fixation points 960A, 960B, 960C can comprise one or more fixation points configured to be selectively illuminated. In some embodiments, the gonioscope can include one or more user input elements (e.g., one or more buttons or switches) configured to receive input from the user for controlling the selective illumination of the multiple fixation points 960A-C. For example, a user can illuminate a first fixation point 960A, while the one or more additional fixation point 960B and 960C are not illuminated. By this manner the user can direct the subject's vision to the illuminated fixation point 960A to facilitate proper orientation of the eye.

Figure 60D:
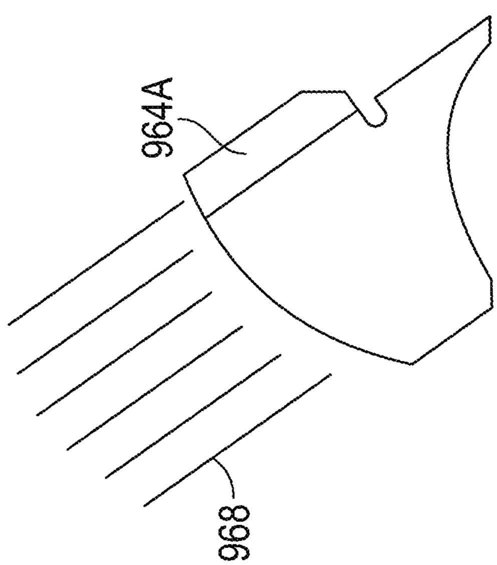
FIGS. 60D to 60F are schematic drawings of side views of different example embodiments of gonioscopic optical elements that include light pipes.
Figure 60E:
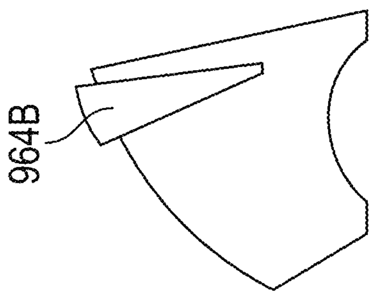
Figure 60F:
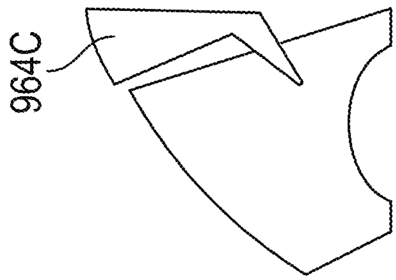
Figure 60G:
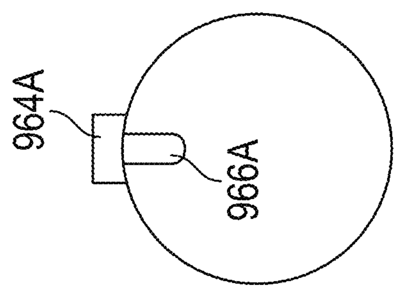
FIGS. 60G to 60I are schematic drawings of bottom views of different example embodiments of gonioscopic optical elements that include light pipes.
Figure 60H:
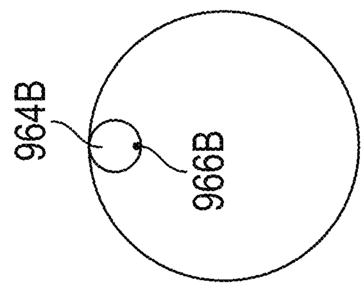
Figure 60I:
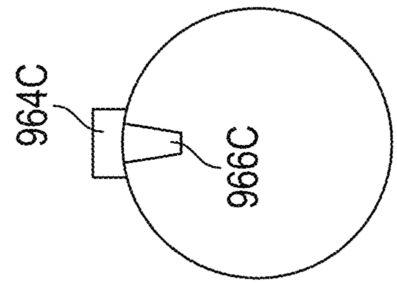

The optical fixation point can comprise a light pipe, in some embodiments. FIGS. 60D to 60F schematically show side views of different example embodiments of gonioscopic optical elements that include light pipes. FIGS. 60G to 60I schematically show bottom views of different example embodiments of gonioscopic optical elements that include light pipes. The gonioscopic light pipes 964A, 964B, 964C can be configured to receive a light from the microscope 968 or other suitable light source (e.g., ambient light). The gonioscopic light pipes 964A, 964B, 964C can be configured to redirect light from the microscope 968 to the patient's eye, to be visible to the patient as a fixation feature. In some embodiments, the receiving end of the light pipe that receives light (e.g., light 968 from the microscope) can be larger than an exit end. The light pipe can be tapered from the receiving end to the exit end, for example to produce a small, bright fixation point 966A, 966B, and 966C for the patient to view. The optical fixation point can comprise a light pipe, in some embodiments. FIGS. 60D and 60E schematically show side and bottom views of different example embodiments of gonioscopic optical elements that include light pipes. The gonioscopic light pipes 964A, 964B, 964C can be configured to receive a light from the microscope 968 or other suitable light source (e.g., ambient light). The gonioscopic light pipes 964A, 964B, 964C can be configured to redirect light from the microscope 968 to the patient's eye, to be visible to the patient as a fixation feature. In some embodiments, the receiving end of the light pipe that receives light (e.g., light 968 from the microscope) can be larger than an exit end. The light pipe can be tapered from the receiving end to the exit end, for example to produce a small, bright fixation point 966A, 966B, and 966C for the patient to view.

In some embodiments, the light pipe 964B can be disposed at least partially inside the gonioscopic optical element. For example, the gonioscopic optical element can be overmolded around the light pipe 964B, or the light pipe can be inserted into a recess that is formed in the gonioscopic optical element. In some embodiments, the light receiving end of the light pipe can be exposed (e.g., on the proximal end of the gonioscopic optical element) to receive light into the light pipe 964B. A majority of the light pipe 964B can be disposed inside the gonioscopic optical element.

The light pipes 964A, 964B, 964C can be disposed partially or completely outside the gonioscopic optical element. The light receiving end of the light pipe 964B can be outside the gonioscopic optical element. The light pipe 964A can be outside the gonioscopic optical element and disposed directly adjacent and in contact with the gonioscopic optical element (e.g., on the thick side of the gonioscopic optical element). The light pipe 964C can be disposed outside and spaced apart from the gonioscopic optical element (e.g., on the thick side of the gonioscopic optical element). An air gap can be disposed between the gonioscopic optical element and the light pipe 964C, and the air gap can facilitate the propagation of light in the light pipe by total internal reflection. In some embodiments, a majority of the light pipe can be disposed outside the gonioscopic optical element, and in some cases a portion of the light pipe 964C (e.g., the light exit portion) can extend into the gonioscopic optical element (e.g., into a recess formed therein). In some embodiments, the light exit portion of the light pipe 964A can be disposed outside the gonioscopic optical element, and a feature (e.g., a recess) on the gonioscopic optical element can be configured to receive light emitted from the light exit portion to direct the light to the eye to provide the fixation point 966A. The light pipe 964A and 964B can be generally linear, or the light pipe 964 can include one or more turns to direct the light to form the fixation point 966A-C. In some embodiments, the material of the light pipe 964A-C can have a higher refractive index than the material of the gonioscopic optical element, to facilitate propagation of light in the light pipe by total internal reflection. The gonioscopic optical element can be configured to act as a cladding material on at least a portion of the outside of the light pipe 964A-C. In some embodiments, a reflective coating can be disposed on the outside of the light pipe 964A-C. The reflective coating can facilitate the propagation of light and/or can provide a separation from the main gonioscopic optical element 928.

Figure 60J:
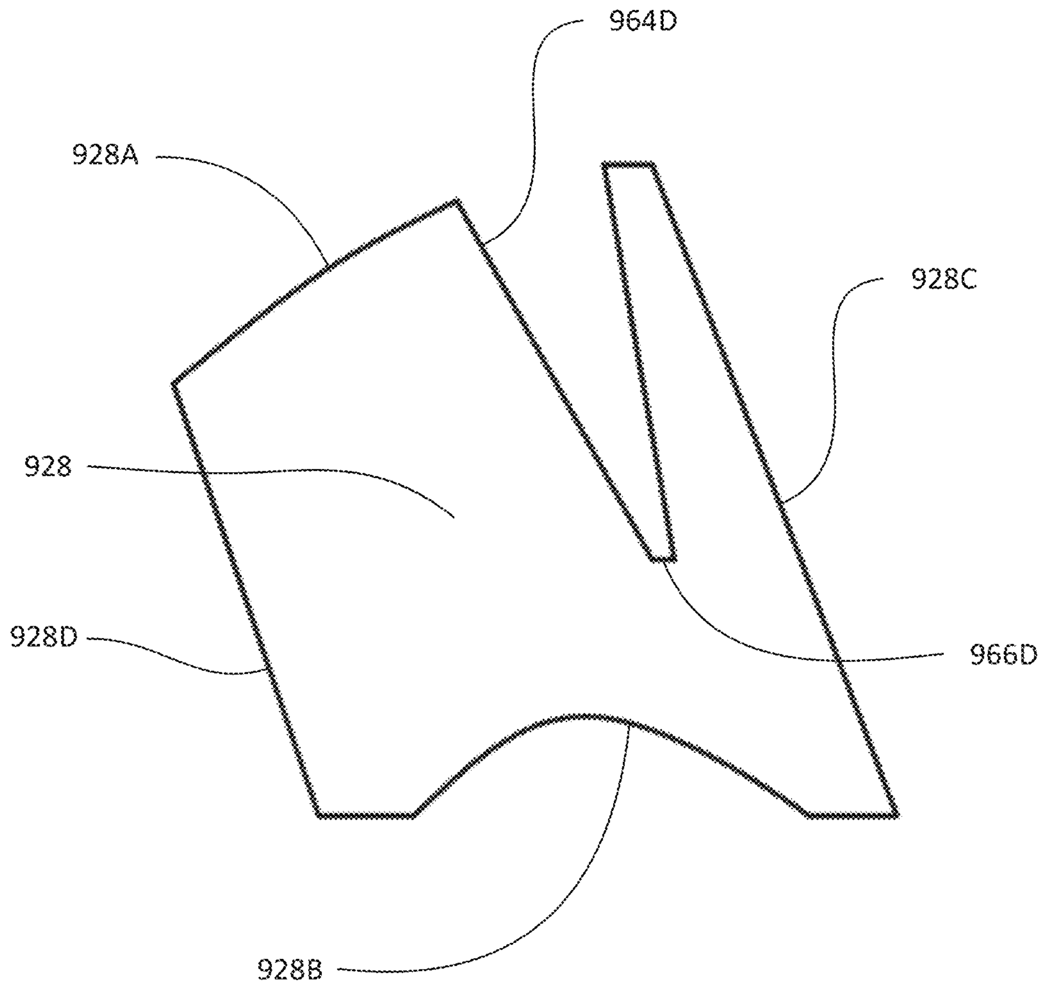
FIG. 60J is a schematic drawing of a side view of an example embodiment of a gonioscopic optical element.

With reference to FIG. 60J, in some embodiments, the gonioscopic optical element 928 can include a light guide 964D that is formed by one or more mirrored or reflective surfaces. The gonioscopic optical element 928 can include a recess (e.g., extending from the proximal surface 928A into the body of the gonioscopic optical element 928). One or more surfaces of the recess can be reflective to guide light along the recess (e.g., to create a fixation point 966D). In some embodiments, the sides of the recess can have a metallic coating or other reflective material thereon, and a bottom portion of the recess does not include the reflective material such that the light is reflected off the sides of the recess until the light reaches the bottom portion of the recess, where the light exits the recess and enters the material of the gonioscopic optical element 928 to be visible to a patient as an optical fixation point 966D. In some cases, the recess can be filled with a higher index material than the surrounding material and light can be reflected by total internal reflection. The light can propagate from the bottom portion of the recess, through the material of the gonioscopic optical element, to the distal surface 928B, in order to be visible to the eye of the patient. In some embodiments, the recess can be tapered having a larger width at the top and a narrower width at the bottom portion, such that the light guided down along the recess can be concentrated at the bottom portion of the recess. The recess can have a generally conical shape (e.g., a conical or frastoconical shape). The recess can have a generally circular, round, or oval cross-sectional shape, or a generally squared, rectangular, or polygonal cross-sectional shape.

Many variations are possible. For example, in some embodiments, the fixation point 960, 1060 can be a colored dot, an ink dot, a colored object, etc., which can be suspended inside the gonioscopic optical element or disposed on an outside surface of the gonioscopic optical element. The various embodiments disclosed regarding gonioscopes that include one or more fixation points can be used together with the embodiments disclosed herein with regards to the retention elements. For example, a gonioscope having one or more fixation points as shown or discussed in connection with any of the embodiments disclosed herein.

Unless the context clearly requires otherwise, throughout the description and the claims, the words "comprise," "comprising," "include," "including," and the like are to be construed in an inclusive sense, as opposed to an exclusive or exhaustive sense, such as in the sense of "including, but not limited to." The words "coupled" or "connected", as generally used herein, refer to two or more elements that can be either directly connected, or connected by way of one or more intermediate elements. Additionally, the words "herein," "above," "below," and words of similar import, when used in this application, shall refer to this application as a whole and not to any particular portions of this application. Where the context permits, words in the Detailed Description using the singular or plural number can also include the plural or singular number, respectively. The words "or" in reference to a list of two or more items, is intended to cover all of the following interpretations of the word: any of the items in the list, all of the items in the list, and any combination of the items in the list. The words "and/or" is also intended to cover all of the following interpretations of the word: any of the items in the list, all of the items in the list, and any combination of the items in the list. The term "based on," as generally used herein, encompasses the following interpretations of the term: solely based on or based at least partly on. All numerical values provided herein are intended to include similar values within a measurement error.

Moreover, conditional language used herein, such as, among others, "can," "could," "might," "may," "e.g.," "for example," "such as" and the like, unless specifically stated otherwise, or otherwise understood within the context as used, is generally intended to convey that certain embodiments include, while other embodiments do not include, certain features, elements and/or states.

The various features and processes described above may be used independently of one another, or may be combined in various ways. All possible combinations and subcombinations are intended to fall within the scope of this disclosure. In addition, certain method or process elements may be omitted in some implementations. The methods and processes described herein are also not limited to any particular sequence, and any blocks or states relating thereto can be performed in other sequences that are appropriate. For example, any described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

The teachings of the embodiments provided herein can be applied to other systems, not necessarily the systems described above. The elements and acts of the various embodiments described above can be combined to provide further embodiments.

While certain embodiments have been described, these embodiments have been presented by way of example only, and are not intended to limit the scope of the disclosure. Indeed, the novel methods and systems described herein can be embodied in a variety of other forms. Furthermore, various omissions, substitutions and changes in the form of the methods and systems described herein can be made without departing from the spirit of the disclosure. The accompanying claims and their equivalents are intended to cover some such forms or modifications as would fall within the scope and spirit of the disclosure.

The following is claimed:

1. A gonioscope comprising:

a gonioscopic optical element comprising:

a bottom side having a contact surface that is concave and configured to contact a surface of an eye of a subject;

a front side wherein the gonioscopic optical element is configured to receive light from structure inside the eye through the bottom side contact surface and to output the light through the front side to form an image of the structure inside the eye; and a back side, wherein the front side and the back side converge towards a junction; and a handle extending upward from the junction.

2. The gonioscope of claim 1, wherein the handle is ambidextrous and extends upward along a center plane that divides the gonioscopic optical element into a right side and a left side.

3. The gonioscope of claim 1, wherein the handle and the gonioscopic optical element are integrally formed of the same material.

4. The gonioscope of claim 1, wherein the front side has a biconic shape.

5. The gonioscope of claim 1, wherein the gonioscopic optical element provides magnification between about 1.1× and 1.5×.

6. The gonioscope of claim 1, wherein the gonioscopic optical element provides magnification between about 1.2× and 1.3×.

7. The gonioscope of claim 1, wherein the front side comprises:

a viewing portion that is configured to receive light from structure inside the eye through the bottom side contact surface and to output the light through the viewing portion to form the image of the structure inside the eye; and a light diffusing portion configured to diffuse light that passes through the light diffusing portion so that at least a portion of the diffused light illuminates the structure inside the eye.

8. The gonioscope of claim 1, wherein the handle has a substantially elliptical cross-sectional shape with a major axis that is longer than a minor axis.

9. The gonioscope of claim 1, wherein the handle comprises:

a first part that narrows in an upward direction from a relatively wide lower portion to a relatively narrow upper portion;

a second part above the first part, wherein the second part widens in an upward direction from a relatively narrow lower portion to a relatively wide upper portion; and a third part above the second part, wherein the third part narrows in an upward direction from a relatively wide lower portion to a relatively narrow upper portion.

10. The gonioscope of claim 1, comprising one or more retention elements configured to engage tissue of the eye to retain the gonioscope in position on the eye.

11. The gonioscope of claim 10, wherein the one or more retention elements are positioned on one or more arms that extend from the gonioscopic optical element.

12. The gonioscope of claim 1, comprising a recess on the back side of the gonioscope, wherein the recess includes a surface configured to reflect light that entered the gonioscopic optical element through the front side, so that the reflected light is directed through the bottom side of the gonioscopic element to provide an optical fixation point.

13. The gonioscope of claim 12, wherein the surface of the recess is configured to reflect the light by total internal reflection.

14. The gonioscope of claim 1, comprising one or more guide markings that are visible in the image of the structure inside the eye.

15. The gonioscope of claim 1, wherein the handle extends upward from an uppermost portion of the gonioscopic optical element.

16. The gonioscope of claim 1, wherein the handle is positioned outside a viewing surface of the front side of the gonioscopic optical element.

17. A gonioscope comprising:

a gonioscopic optical element made of transparent material and comprising:

a distal contact surface that is concave and configured to contact a surface of an eye of a subject; and a proximal surface, wherein the gonioscopic optical element is configured to receive light from structure inside the eye through the distal contact surface and to output the light through the proximal surface to form an image of the structure inside the eye; and a handle coupled to the gonioscopic optical element, wherein the handle and the gonioscopic optical element are integrally formed as one piece of the same material.

18. The gonioscope of claim 17, wherein the handle is ambidextrous and extends upward along a center plane that divides the gonioscopic optical element into a right side and a left side.

19. The gonioscope of claim 17, wherein the proximal surface has a biconic shape.

20. The gonioscope of claim 17, wherein the gonioscopic optical element provides magnification between about 1.1× and 1.5×.

21. The gonioscope of claim 17, wherein the gonioscopic optical element provides magnification between about 1.2× and 1.3×.

22. The gonioscope of claim 17, wherein the proximal surface comprises:

a viewing portion that is configured to receive light from structure inside the eye through the distal contact surface and to output the light through the viewing portion to form the image of the structure inside the eye; and a light diffusing portion to diffuse light that passes through the light diffusing portion so that at least a portion of the diffused light illuminates the structure inside the eye.

23. The gonioscope of claim 17, wherein the handle has a substantially elliptical cross-sectional shape with a major axis that is longer than a minor axis.

24. The gonioscope of claim 17, wherein the handle comprises:

a first part that narrows in an upward direction from a relatively wide lower portion to a relatively narrow upper portion;

a second part above the first part, wherein the second part widens in an upward direction from a relatively narrow lower portion to a relatively wide upper portion; and a third part above the second part, wherein the third part narrows in an upward direction from a relatively wide lower portion to a relatively narrow upper portion.

25. The gonioscope of claim 17, comprising one or more retention elements configured to engage tissue of the eye to retain the gonioscope in position on the eye.

26. The gonioscope of claim 25, wherein the one or more retention elements are positioned on one or more arms that extend from the gonioscopic optical element.

27. The gonioscope of claim 17, comprising a recess on a back side of the gonioscope, wherein the recess includes a surface configured to reflect light that entered the gonioscopic optical element through the proximal surface, so that the reflected light is directed through the distal surface of the gonioscopic element to provide an optical fixation point.

28. The gonioscope of claim 27, wherein the surface of the recess is configured to reflect the light by total internal reflection.

29. The gonioscope of claim 17, comprising one or more guide markings that are visible in the image of the structure inside the eye.

30. The gonioscope of claim 17, wherein the gonioscopic optical element and the handle are made from a material that is less flexible than silicone.

31. A gonioscope comprising:

a gonioscopic optical element made of transparent material and comprising:

a distal contact surface that is concave and configured to contact a surface of an eye of a subject; and a proximal surface, wherein the gonioscopic optical element is configured to receive light from structure inside the eye through the distal contact surface and to output the light through the proximal surface to form an image of the structure inside the eye; and a handle coupled to the gonioscopic optical element, wherein the handle comprises:

a first part that narrows in an upward direction from a relatively wide lower portion to a relatively narrow upper portion;

a second part above the first part, wherein the second part widens in an upward direction from a relatively narrow lower portion to a relatively wide upper portion; and a third part above the second part, wherein the third part narrows in an upward direction from a relatively wide lower portion to a relatively narrow upper portion.

32. A gonioscope comprising:

a gonioscopic optical element made of transparent material and comprising:

a distal contact surface that is concave and configured to contact a surface of an eye of a subject; and a proximal surface, wherein the proximal surface comprises:

a viewing portion that is configured to receive light from structure inside the eye through the distal contact surface and to output the light through the viewing portion of the proximal surface to form an image of the structure inside the eye; and a light diffusing portion configured to diffuse light that passes through the light diffusing portion so that at least a portion of the diffused light illuminates the structure inside the eye; and a handle coupled to the gonioscopic optical element.

33. The gonioscope of claim 32, wherein the light diffusing portion is positioned above the viewing portion.

* * * * *